(12) United States Patent
Kim et al.

(10) Patent No.: US 9,018,011 B2
(45) Date of Patent: Apr. 28, 2015

(54) GAMMA SATELLITE INSULATOR SEQUENCES AND THEIR USE IN PREVENTING GENE SILENCING

(75) Inventors: Jung-Hyun Kim, Rockville, MD (US); Vladimir L. Larionov, Potomac, MD (US); Tom Ebersole, Brownsville, TX (US)

(73) Assignee: The United States as represented by the Secretary of the Department of Health and Human Services, Washington, DC (US)

( * ) Notice: Subject to any disclaimer, the term of this patent is extended or adjusted under 35 U.S.C. 154(b) by 724 days.

(21) Appl. No.: 12/527,122

(22) PCT Filed: Feb. 15, 2008

(86) PCT No.: PCT/US2008/054170
§ 371 (c)(1),
(2), (4) Date: Aug. 13, 2009

(87) PCT Pub. No.: WO2008/101216
PCT Pub. Date: Aug. 21, 2008

(65) Prior Publication Data
US 2010/0022006 A1 Jan. 28, 2010

Related U.S. Application Data

(60) Provisional application No. 60/890,176, filed on Feb. 15, 2007.

(51) Int. Cl.
C12N 15/85 (2006.01)
C12N 15/87 (2006.01)

(52) U.S. Cl.
CPC ............ *C12N 15/85* (2013.01); *C12N 2830/46* (2013.01)

(58) Field of Classification Search
USPC ................................................ 435/455, 463
See application file for complete search history.

(56) References Cited

U.S. PATENT DOCUMENTS

| | | | |
|---|---|---|---|
| 5,972,643 A | 10/1999 | Lobanenkov et al. | |
| 6,524,851 B1 | 2/2003 | Ellis | |
| 2002/0106789 A1 * | 8/2002 | Antoniou et al. | 435/320.1 |

OTHER PUBLICATIONS

Allen et al., Tandemly repeated transgenes of the human minisatellite MS32 (D1S8), with novel mouse gamma satellite integration, Nucleic Acids Res. 22(15):2976-81, 1994.*
Koipally et al., Unconventional potentiation of gene expression by Ikaros, J Biol Chem. 277(15):13007-15, 2002.*
Brown et al., "Association of Transcriptionally Silent Genes with Ikaros Complexes at Centromeric Heterochromatin," *Cell*, 91(6):845-854, 1997.
Filippova et al., "Boundaries between Chromosomal Domains of X Inactivation and Escape Bind CTCF and Lack CpG Methylation during Early Development," *Developmental Cell*, 8(1):31-42, 2005.
Gaszner and Felsenfeld, "Insulators: exploiting transcriptional and epigenetic mechanisms," *Nature Reviews Genetics*, 7(9):703-710, 2006.
Kim et al., "Human gamma-satellite DNA maintains open chromatin structure and protects a transgene from epigenetic silencing," *Genome Res.*, 19(4): 533-544, 2009 (and supplemental material).
Bell and Felsenfeld, "Methylation of a CTCF-dependent boundary controls imprinted expression of the Igf2 gene," *Nature*, 405(6785):482-485 (2000).
Bell et al, "The protein CTCF is required for the enhancer blocking activity of vertebrate insulators," *Cell*, 98(3):387-396 (1999).
Black et al, "Centromere identity maintained by nucleosomes assembled with histone H3 containing the CENP-A targeting domain," *Mol. Cell* 25(2):309-322 (2007).
Burke et al., "CTCF binding and higher order chromatin structure of the H19 locus are maintained in mitotic chromatin," *The EMBO Journal*, 24(18):3291-3300 (2005).
Chen et al., "Silencing of episomal transgene expression by plasmid bacterial DNA elements in vivo," *Gene Therapy*, 11(10):856-864 (2004).
Chung et al. "A 5' element of the chicken beta-globin domain serves as an insulator in human erythroid cells and protects against position effect in *Drosophila*," *Cell*, 74(3):505-514 (1993).
Cobb et al., "Targeting of Ikaros to pericentromeric heterochromatin by direct DNA binding," *Genes and Development*, 14:2146-2160 (2000).
Filippova et al., "An exceptionally conserved transcriptional repressor, CTCF, employs different combinations of zinc fingers to bind diverged promoter sequences of avian and mammalian c-myc oncogenes," *Mol Cell Biol.*, 16(6):2802-2813 (1996).
Frazar et al., "Variegated Expression from the Murine Band 3 (AEI) Promoter in Transgenic Mice Is Associated with mRNA Transcript Initiation at Upstream Start Sites and Can Be Suppressed by the Addition of the Chicken β-Globin 5' HS4 Insulator Element," *Molecular and Cellular Biology*, 23(14):4753-4763 (2003).
GenBank Accession No. X68546, "*H.sapiens* gamma satellite DNA (sub-clone 50E4)," GI:193675, Oct. 18, 1999, 2 pages.
Gosden et al., "The location of four human satellite DNAs on human chromosomes," *Exp. Cell Res.*, 92:148-158 (1975).
Gurel et al., "Recruitment of Ikaros to Pericentromeric Heterochromatin is Regulated by Phosphorylation," *The Journal of Biological Chemistry*, pp. 1-19 (2008).
Jakobsson, et al., "Dynamics of transgene expression in a neural stem cell line transduced with lentiviral vectors incorporating the cHS4 insulator," *Exp Cell Res.*, 298(2):611-623 (2004).
Kanduri et al., "Functional association of CTCF with the insulator upstream of the H19 gene is parent of origin-specific and methylation-sensitive," *Curr Biol.*, 10:853-856 (2000).
Kim et al., "Analysis of the vertebrate insulator protein CTCF-binding sites in the human genome," *Cell*, 128(6):1231-1245 (2007).
Kurukuti et al., "CTCF binding at the *H19* imprinting control region mediates maternally inherited higher-order chromatin conformation to restrict enhancer access to *Igh2*," *PNAS*, 103(28):10684-10689 (2006).
Lee et al., "Distribution of gamma satellite DNA on the human X and Y chromosomes suggests that it is not required for mitotic centromere function," *Chromosoma*, 109(6):381-389 (2000).
Lee et al., "Human centromeric DNAs," *Hum. Genet.*, 100(3-4):291-304 (1997).
Lee et al., "Human gamma X satellite DNA: an X chromosome specific centromeric DNA sequence," *Chromosoma*, 104(2):103-112 (1995).

(Continued)

*Primary Examiner* — Marcia S Noble
(74) *Attorney, Agent, or Firm* — Klarquist Sparkman, LLP

(57) ABSTRACT

Regulatory elements, specifically insulators and transgene constructs containing insulator nucleic acid sequences, are disclosed herein. Methods of using insulators and transgene constructs including insulators to inhibit, delay, or prevent gene silencing are also disclosed herein.

14 Claims, 33 Drawing Sheets

(56) References Cited

OTHER PUBLICATIONS

Lewis et al., "Genomic Imprinting: CTCF Protects the Boundaries," *Current Biology*, 14:R284-R286 (2004).

Lin et al., "Isolation and identification of a novel tandemly repeated DNA sequence in the centromeric region of human chromosome 8," *Chromosoma*, 102:333-339 (1993).

Ling et al., "CTCF mediates interchromosomal colocalization between Igf2/H19 and Wsb1/Nf1," *Science*, 312(5771):269-272 (2006).

Lobanenkov et al., "A novel sequence-specific DNA binding protein which interacts with three regularly spaced direct repeats of the CCCTC-motif in the 5'-flanking sequence of the chicken c-myc gene," *Oncogene*, 5(12):1743-1753 (1990) (Abstract only).

Lutz et al., "Thyroid hormone-regulated enhancer blocking: cooperation of CTCF and thyroid hormone receptor," *EMBO J*, 22:1579-1587 (2003).

Ma et al., "High-Level Sustained Transgene Expression in Human Embryonic Stem Cells Using Lentiviral Vectors," *Stem Cells*, 21:111-117 (2003).

Meyne et al., "Chromosome localization and orientation of the simple sequence repeat of human satellite I DNA," *Chromosoma*, 103(2):99-103 (1994).

Mukhopadhyay et al., "The Binding Sites for the Chromatin Insulator Protein CTCF Map to DNA Methylation-Free Domains Genome-Wide," *Genome Research*, 14:1594-1602 (2004).

Mutskov et al., "The barrier function of an insulator couples high histone acetylation levels with specific protection of promoter DNA from methylation," *Genes & Development*, 16:1540-1554 (2002).

Ohlsson et al., "CTCF is a uniquely versatile transcription regulator linked to epigenetics and disease," *Trends Genet.*, 17(9):520-527 (2001).

Rincon-Arano et al., "Sustained heterologous transgene expression in mammalian and avian cell lines," *Methods Mol. Biol.*, 267:435-450 (2004).

Schueler and Sullivan, "Structural and functional dynamics of human centromeric chromatin," *Ann Rev Genomics Hum Genet* 7:301-313 (2006).

Schueler et al, "Genomic and genetic definition of a functional human centromere," *Science*, 294(5540):109-115 (2001).

Schueler et al., "Progressive proximal expansion of the primate X chromosome centromere," *Proc Natl Acad Sci U S A.*, 102(30):10563-10568 (2005).

Song et al., "Deviation of islet autoreactivity to cryptic epitopes protects NOD mice from diabetes," *Eur J Immunol.*, 33(2):546-555 (2003).

Suzuki et al., "Plasmid DNA sequences present in conventional herpes simplex virus amplicon vectors cause rapid transgene silencing by forming inactive chromatin," *J. Virol.*, 80(7):3293-3300 (2006).

Vissel and Choo, "Mouse major (gamma) satellite DNA is highly conserved and organized into extremely long tandem arrays: implications for recombination between nonhomologous chromosomes," *Genomics*, 5(3):407-414 (1989).

West et al., "Insulators: many functions, may mechanisms," *Genes & Development*, 16:271-288 (2002).

Yusufzai and Felsenfeld, "The 5'-HS4 chicken beta-globin insulator is a CTCF-dependent nuclear matrix-associated element," *Proc. Natl. Acad. Sci. USA*, 101(23):8620-8624 (2004).

Zhao et al., "Organizing the genome: enhancers and insulators," *Biochem. Cell Biol.*, 83:516-524 (2005).

* cited by examiner

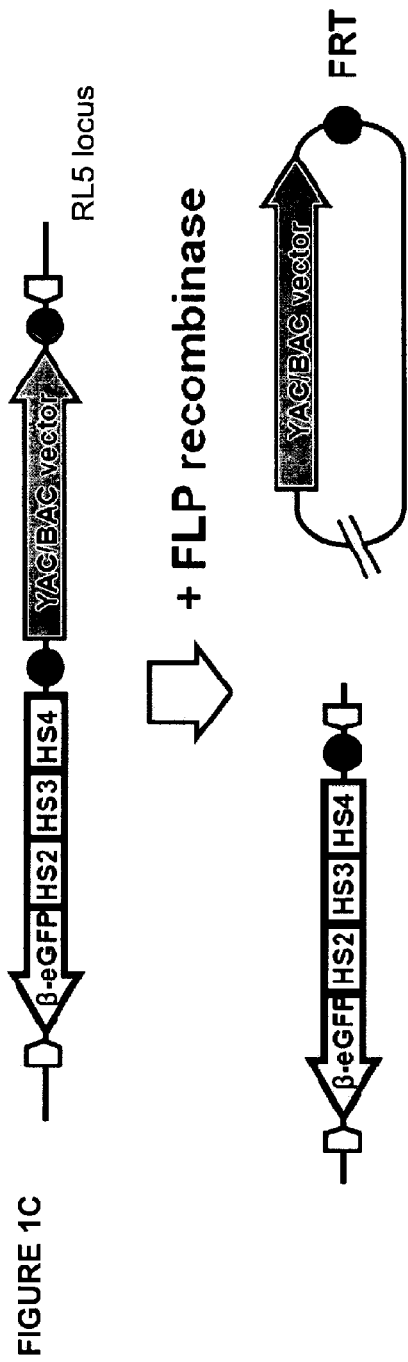
FIGURE 1C
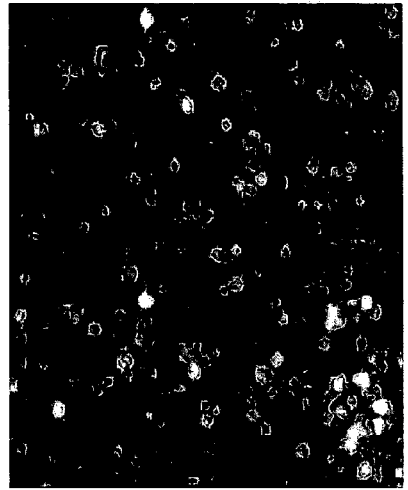
After excision
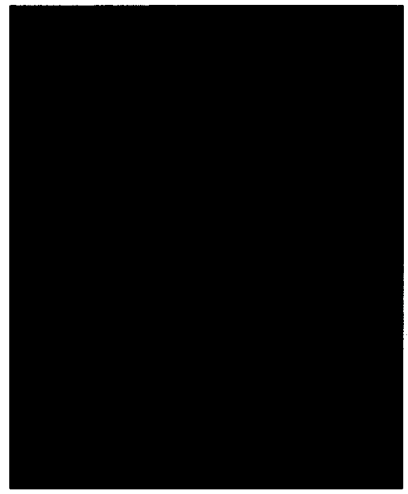
Before excision
FIGURE 1D

FIGURE 2C

| Repeat | Size of monomer (in bp) | Unit for amplification | Size of arrays (in kb) |
|---|---|---|---|
| *Mouse* | | | |
| Major satellite | 234 | 3 mer | 10, 20 |
| *Human* | | | |
| α21-1 alphoid | 171 | 11 mer | 10, 18, 35 |
| Gamma 8 | 220 | 8 mer | 3, 9, 24 |

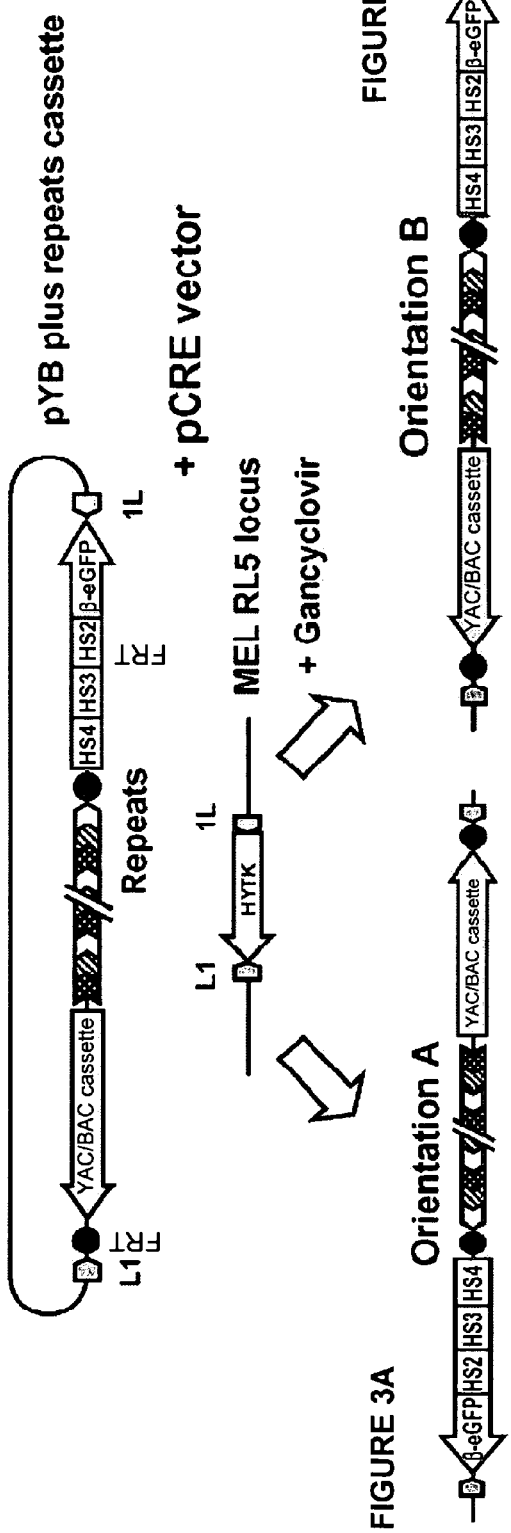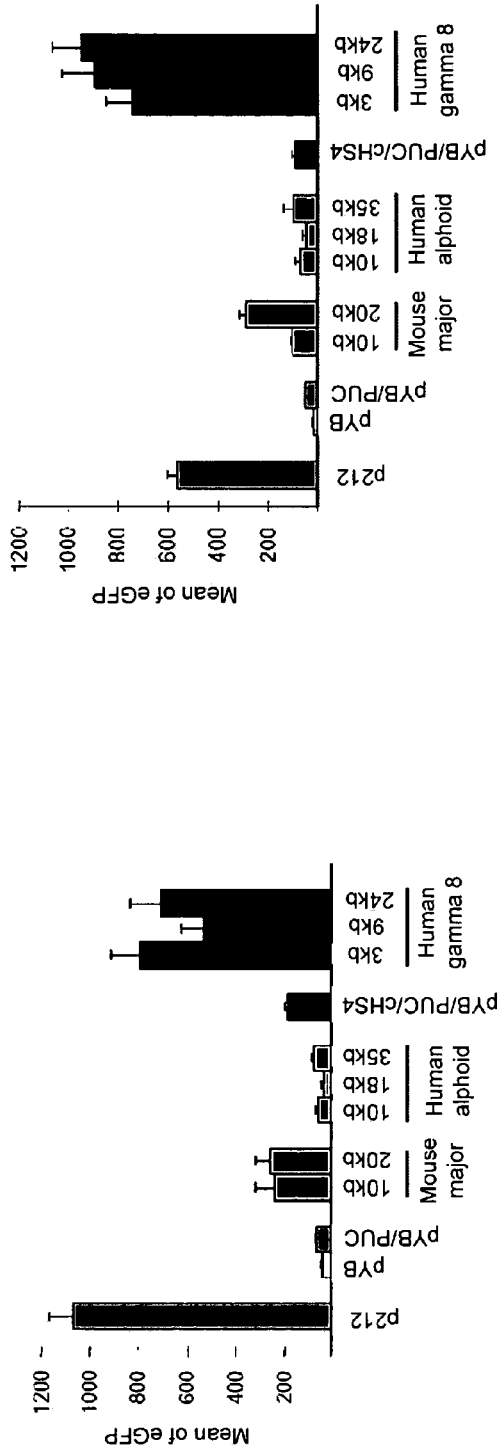
FIGURE 3A
FIGURE 3B

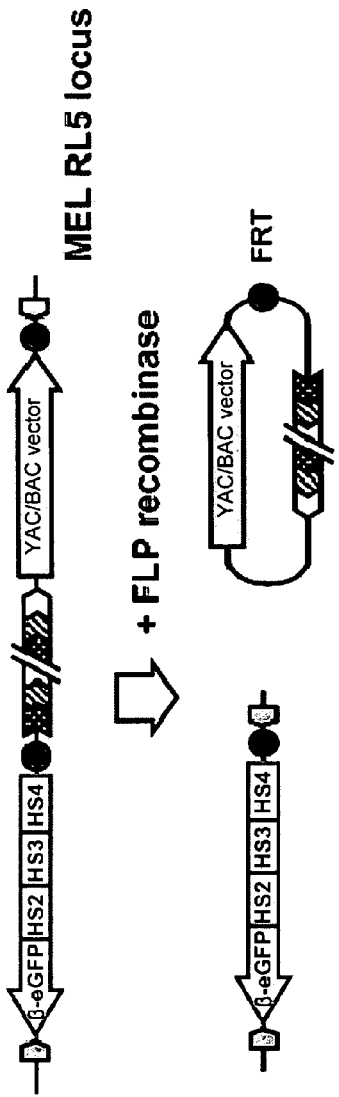
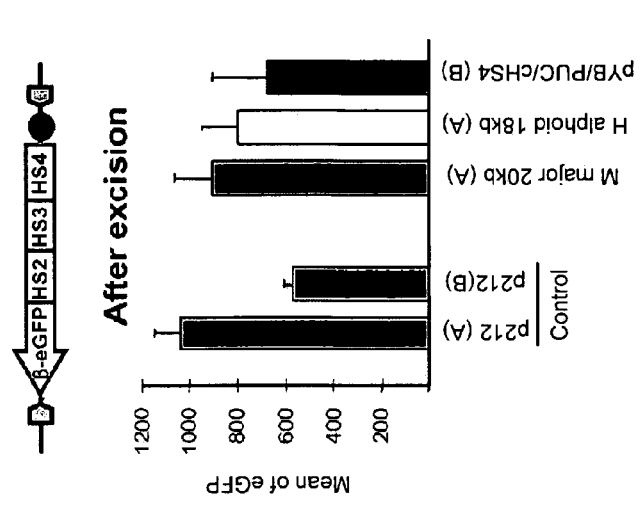
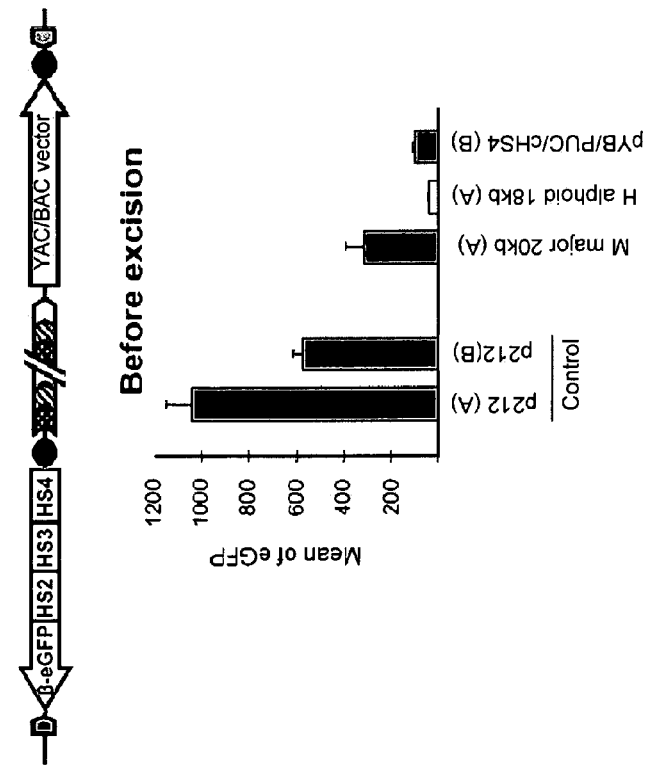
FIGURE 3C
FIGURE 3D

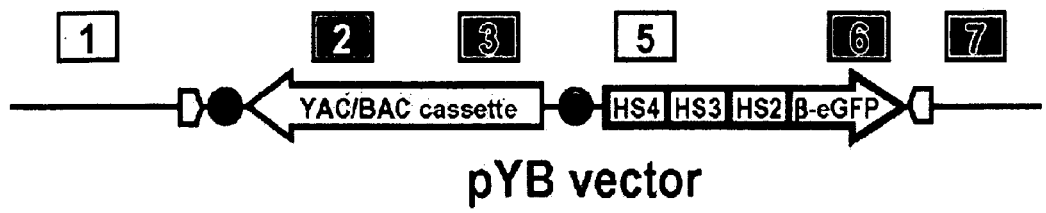
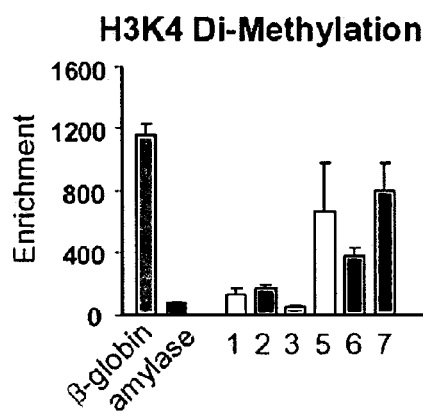 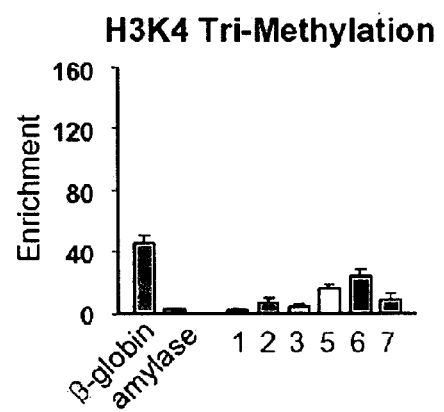
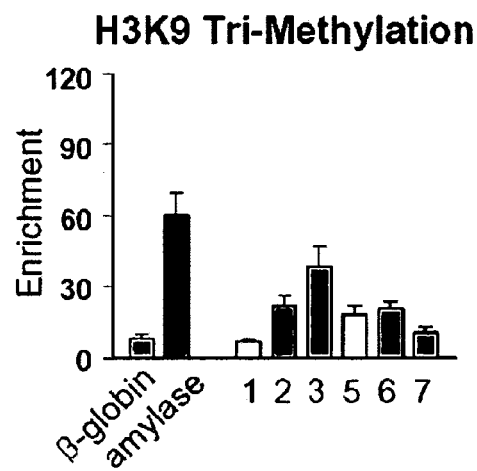
FIGURE 4B

FIGURE 4C
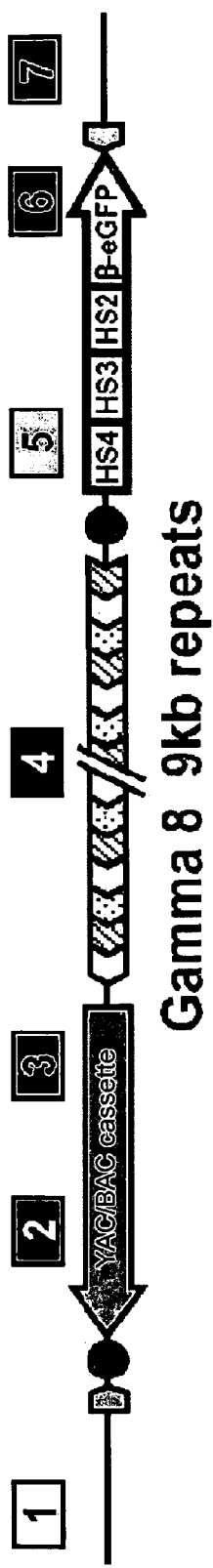
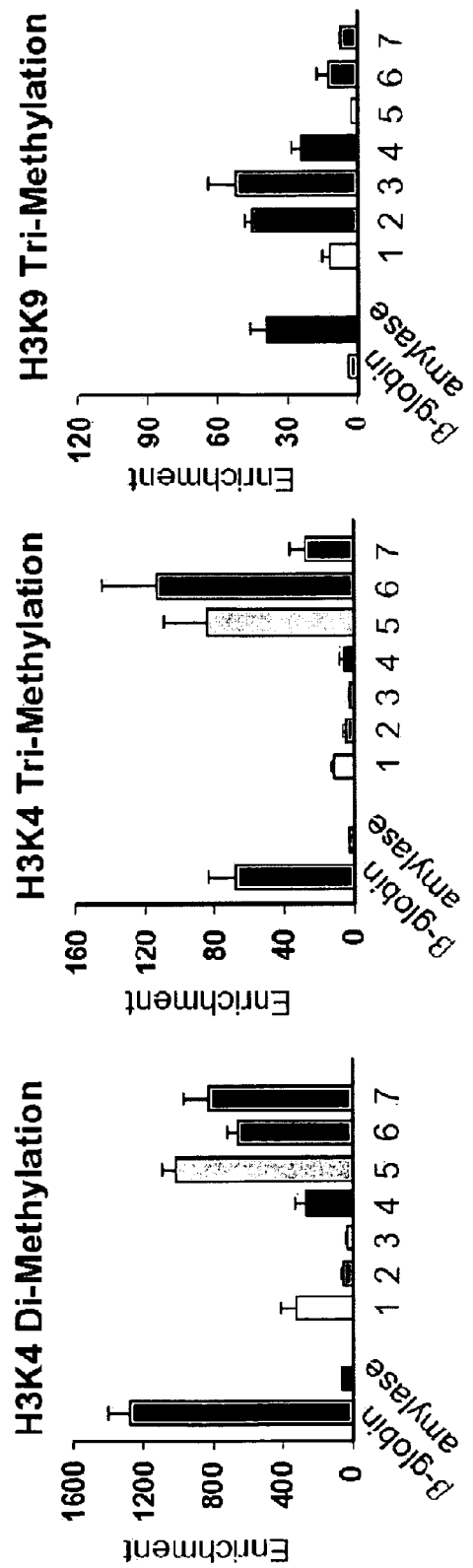

FIGURE 4D
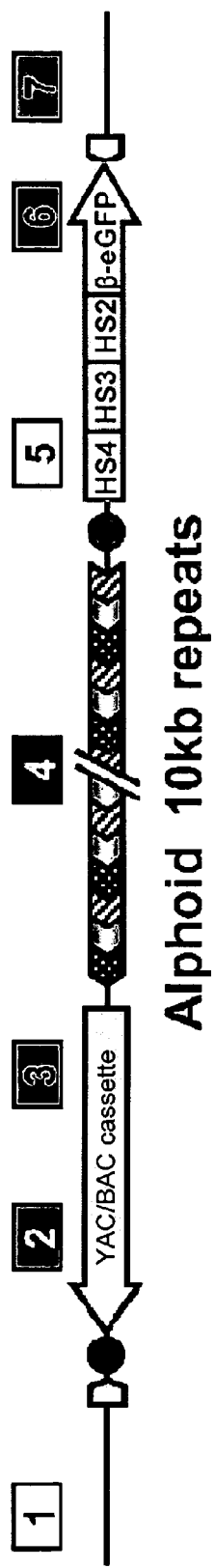
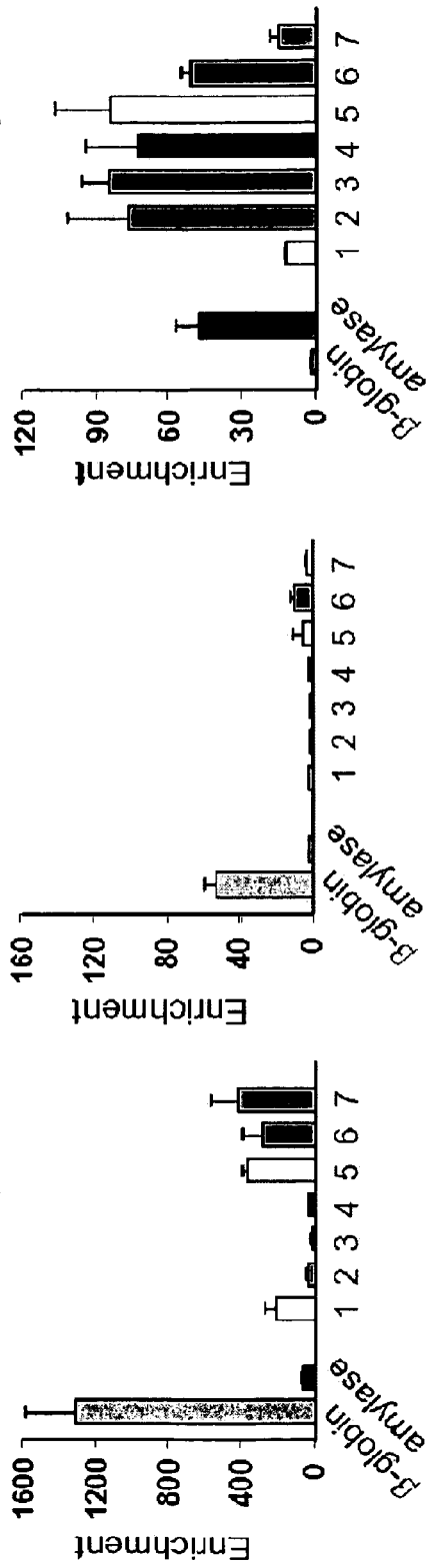

Figure 5A
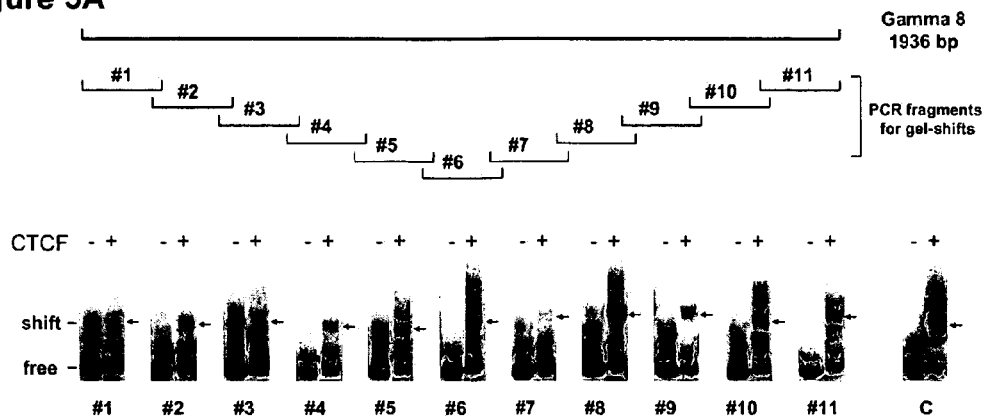
Figure 5C
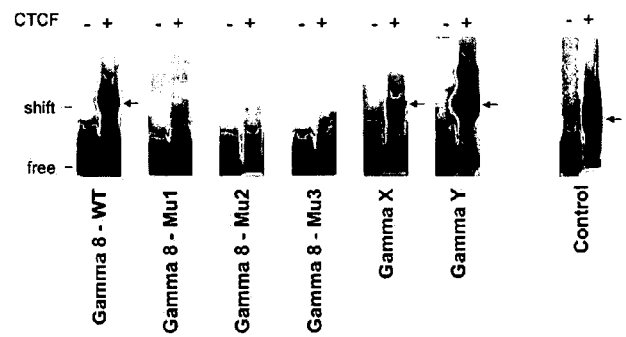
Figure 5D
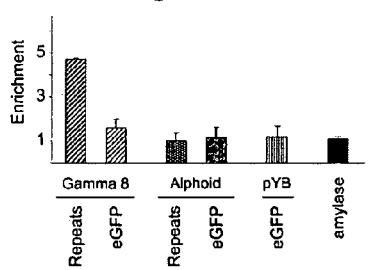
Figure 5E
Figure 5F
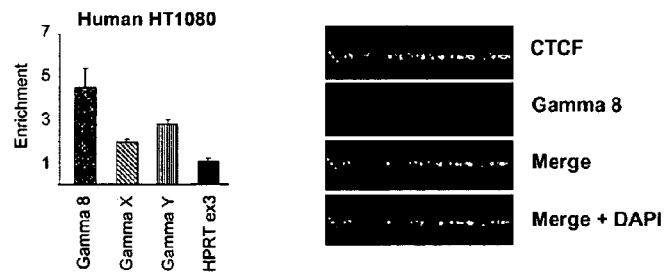

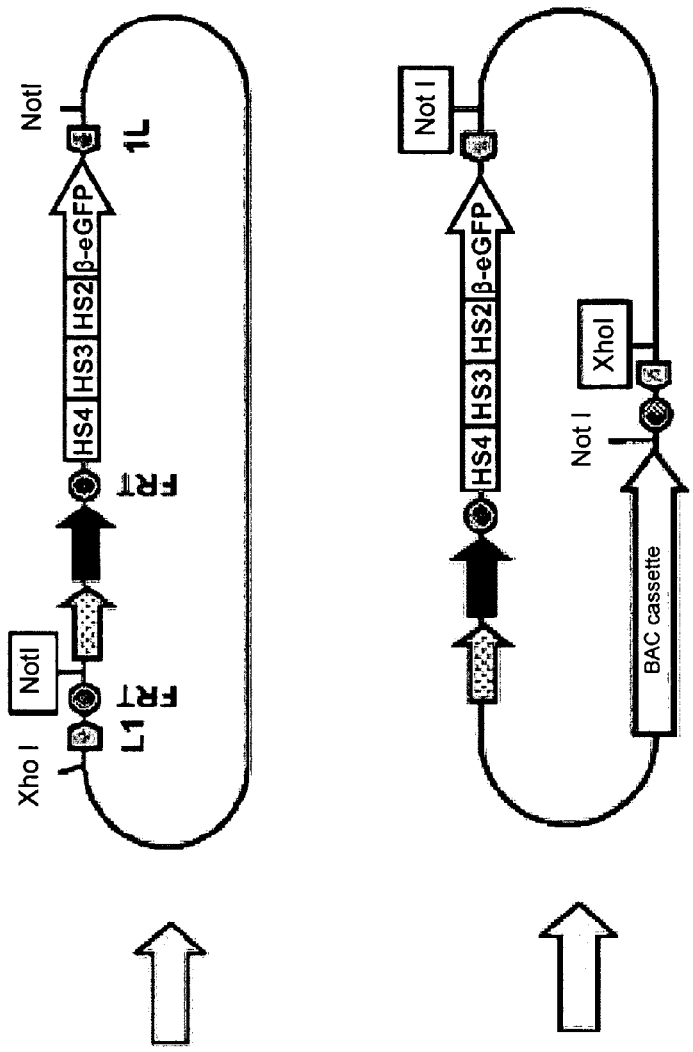
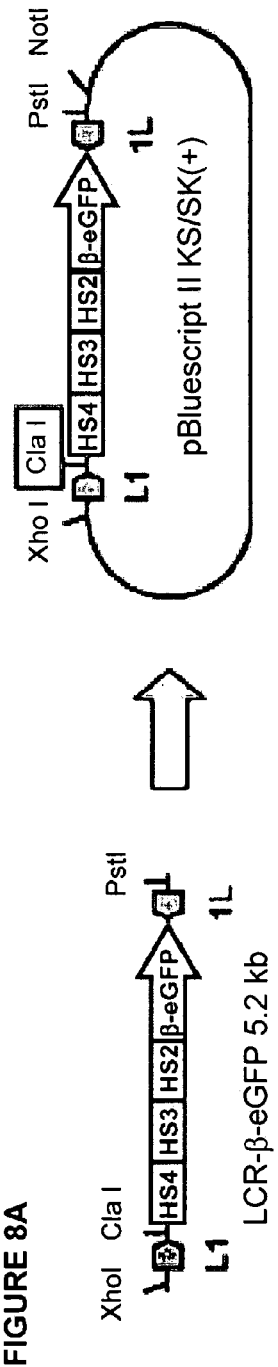
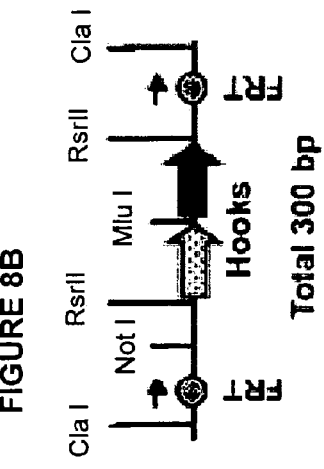
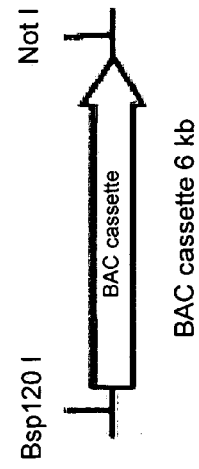
FIGURE 8A
FIGURE 8B
FIGURE 8C

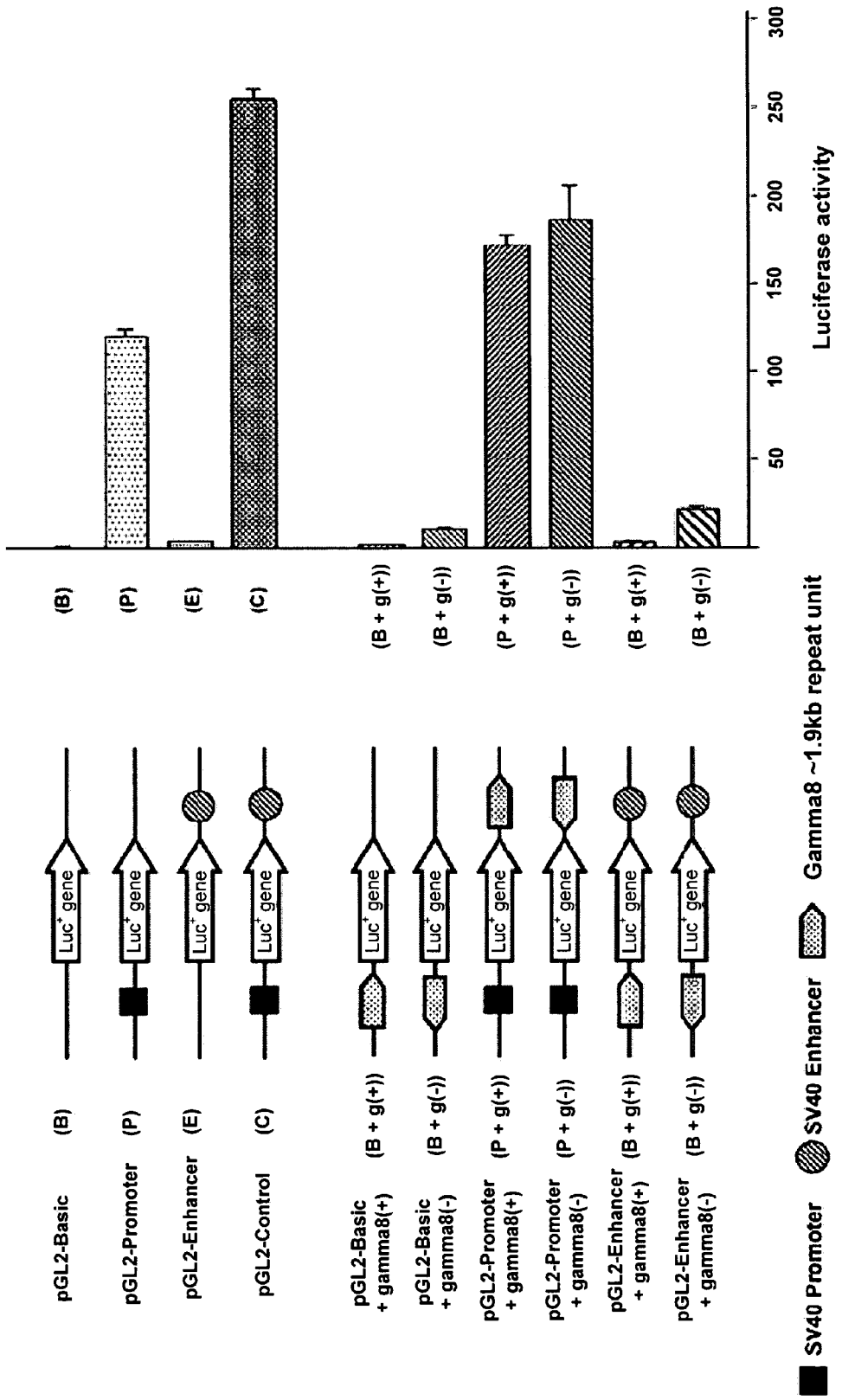

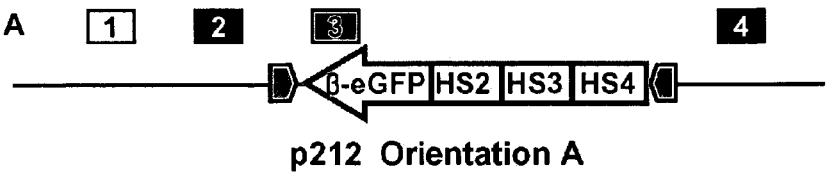
FIGURE 11A  p212 Orientation A
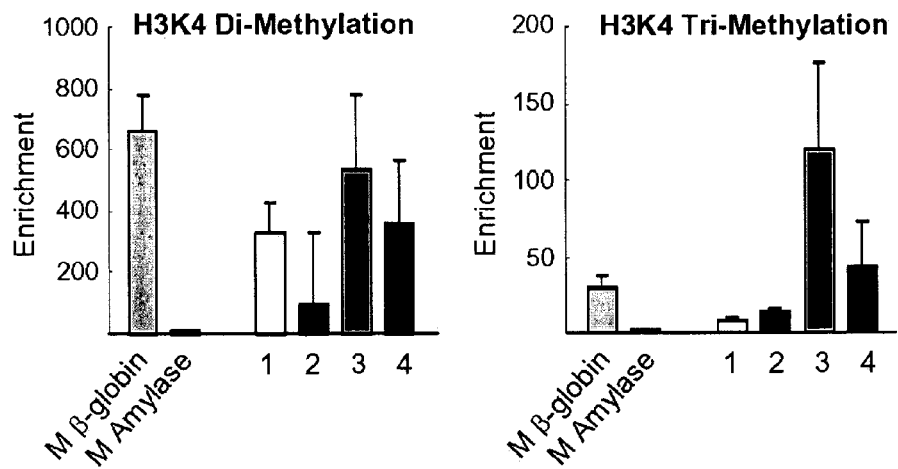
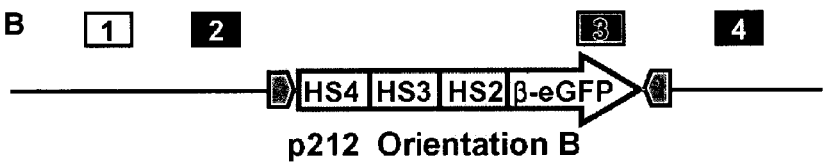
FIGURE 11B  p212 Orientation B
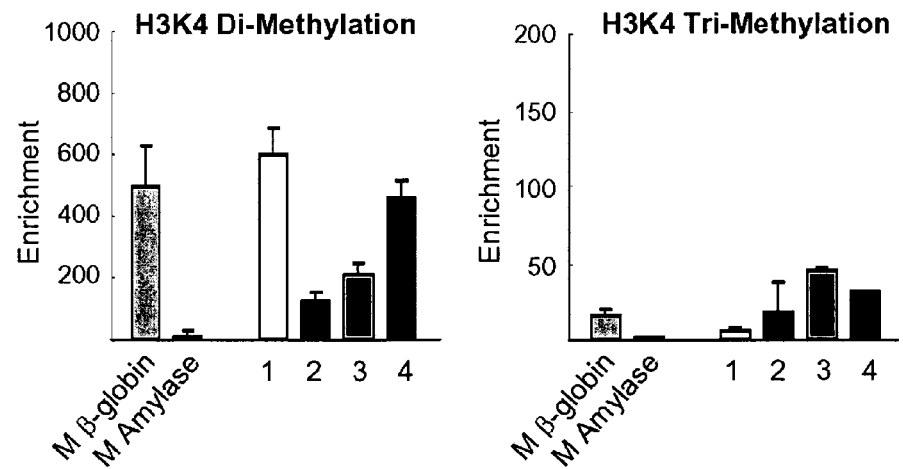

FIGURE 12A

```
1.  CGAAAATGGGGCCACATGGTGGCGGCTTGGGTGGGGCGGCCAAAGACCCCAGGGTGACCTTTGAGG    SEQ ID NO:135
2.  CGGAAAAGGGGCCTGCAGTGTGGCCGTCGACAGGGGACTCAGGGGAAGTTGAAA              SEQ ID NO:136
3.  AGAGAATGAGGTGGTGGCCCGGCATGGGGTGGGCAGCCCAGGGACTCACGGACACTTTGAGG      SEQ ID NO:137
4.  CAAAAACAAGGCCGCCGGCAGTGGGCCAGGGCCCAGGGACTCAGGGGACTCAGGGTGAAATTGTGG  SEQ ID NO:138
5.  CAAAAACAGTGCCGCCAGTGTGGCCTGTGGGCCGATCGTAGGGACTCAGGGGAGACGTTGAGG     SEQ ID NO:139
6.  AGACAACAGGGCGGCCTGGATGGCATGGCTGGCACCCAGGGAAACCCAGGGAGACATTGAGG      SEQ ID NO:140
7.  TGAAAACAGGGACAGGGCAGGAGCCAGGGCCCGCAGCCCAGGGACTATGGTGGACATTGTGG      SEQ ID NO:141
8.  CGAAAATGGGGCCACTGGGTGGCCCTGAAGAGAGCCAAAGGGACTCAGGGTGACACTGAGG       SEQ ID NO:142
```

Consensus: 5' <u>CA</u>/<u>T</u><u>GGGTGG</u>CN<u>TGG</u>NC 3' (SEQ ID NO:1)

FIGURE 12B

WT-8:  CGAAAATGGGGCCACTGGGTGGCCCTGAAC<u>G</u>AGCCAAAGGGACTCAGGGTGACACT    SEQ ID NO:143

Mu1-8: CGAAAATGGGGCCACTAAATGGTCTCGAACGAGCCAAAGGGACTCAGGGTGACACT    SEQ ID NO:144

Mu2-8: CGAAAATGGGGCCACTGAGTGGTTTGAATGAGCCAAAGGGACTCAGGGTGACACT     SEQ ID NO:145

Mu3-8: CGAAAATGGGGTCATTAGGTGGTCTGAATGAGCCAAAGGGACTCAGGGTGACACT     SEQ ID NO:146

```
GSATII   1    A  C TGC  G    A - - G    A GC  GGC  A    T   T   CAT GG   C
GSATX    1    G  C GCC  A    GGGG  - T CC - GGA  G    T   C   T CA GG   G
GSAT     1    C  G C-T  T    GGGC  - CTC - AAA  G    A   C   T GGA G   G

GSATII   49   A  TGCC  CG   GG  C  A - GG  C    C  AG  C   - - - - - - - - - AAG     C         G
GSATX    49   T  CCTC  CT   CT  C  A - TG  C    C  A - C   - - - - - - - - G AAA     C         A
GSAT     48   T  CCTC  GT   CT  T  G GGA  A    C  CC  A   AAGCGAAAAC GGG     C         G

GSATII   88   AA  C - - - -  - - - - - - - - - -  - - - - - - - - - -  - - - - - - TGA  AA          GG
GSATX    88   AA  T - CCC  CA GGG GACAG   GGACAGGACG   CC AGG C  TTC  AG          GG
GSAT     98   GT  C GTGT  GC GGG CC - GC   A - - - - - - - - -  - G AAC  CAG  - -          CA

GSATII   108  C          CCT  GTGTTGT GGA    GG AAA CAC   AA            - G AG  - - - -
GSATX    137  T          GG - - - - CCGGGG    A - - AAA - -   C            - G CA  AGAG
GSAT     135  T          GG - - - - - - - - - C    GG - AGGG GAG    A            AC TC GGG -

GSATII   153  - - - - - - - - - G    GT  C   CC   AG  GC AAA   C G - C       CA GC   G SEQ ID NO:147
GSATX    175  G - AGGGTGG    GT    T   - -   CC  AG  TCA   C GG   T       GGGA   G SEQ ID NO:148
GSAT     173  - AATGGTGG    AG  T    - -   AA  AGC CCT   C CC A       AGAA  GG SEQ ID NO:149
```

FIGURE 13B

Mean identity between sequences [%]

| Indentity | seq1 | seq2 |
|---|---|---|
| seq1 | | ungapped |
| seq2 | gapped | |

| | GSATII | GSATX | GSAT |
|---|---|---|---|
| GSATII | | 68.79 | 53.8 |
| GSATX | 50.85 | | 63.45 |
| GSAT | 39.32 | 52.74 | |

Proportions of insertions and deletions (indels) in pairwise alignments [%]

| Indels | seq1 | seq2 |
|---|---|---|
| seq1 | | indels |
| seq2 | | |

| | GSATII | GSATX | GSAT |
|---|---|---|---|
| GSATII | | 26.07 | 26.92 |
| GSATX | | | 16.88 |
| GSAT | | | |

FIGURE 15

```
     1                                                          60
1 ATTCACGTCCTAAAGTGTGTATTCTCATTTCCGTAATTTCAGTTTTCTCACCATATT
2 TTTCACGTCCTAAAGTGTGTATTCTCATTTCCGTGATTTCAGTTTTCTCACCATATT
3 TTTCACGTCCTAAAGTGTGTATTCTCATTTCCGTGATTTCAGTTTTCTCGCCATATT 61                                                         120
1 CCAGGTCCTTCAGTGGGCATTTCTCATTTTTCACGTTTTTAGTGATTCGTCATTTTTC
2 CCAGGTCCTTCGGTGTGCATTTCTCATTTTTCACGTTTATTAGTGATTCGTCATTTTTC
3 CCAGGTCCTTCAGTGTGCATTTCTCATTTTTCACGTTTTTTAGTGATTCGTCATTTTTC 121                                                         180
1 AAGTCGTCAAGTGGATGTTTCTCATTTTCCATGATTTTCAGTTTTCTTGCCATATTCCAC
2 AAGTCGTCAAGTGGATGTTTCTCATTTTCCATGATTTTCCGGTTTTCTTGCCATATTCCAC
3 AAGTCGTCCAGTGGATGTTTCTCATTTTCCATGATTTTCAGTTTTCTTGCCATATTCCAC 181                                            236
1 GTCCTACAGTGGACATTTCTAAATTTCCACCTTTTTCAGTTTTCCTTTCTCCCATA  SEQ ID NO:150
2 GTCCTACAGTGGACATTTCTAAATTTCCACCTTTTTCAGTTTTCCT--CGCCATA   SEQ ID NO:151
3 GTCCTACAGTGGACATTTCTAAATTTCCACCTTTTTCAGTTTTCCT--CGCCAGA   SEQ ID NO:152
```

GAMMA SATELLITE INSULATOR SEQUENCES AND THEIR USE IN PREVENTING GENE SILENCING

CROSS REFERENCE TO RELATED APPLICATIONS

This is the U.S. National Stage of International Application No. PCT/US2008/054170, filed Feb. 15, 2008, which was published in English under PCT Article 21(2), which in turn claims the benefit of U.S. Provisional Application No. 60/890,176, filed Feb. 15, 2007. Both applications are hereby incorporated by reference in their entirety.

FIELD OF THE DISCLOSURE

This disclosure relates to the field of regulatory elements, specifically to insulators and transgene constructs containing insulator nucleic acid sequences. It also relates to the use of such insulator and transgene constructs to inhibit, delay, or prevent gene silencing.

BACKGROUND

The centromere is a specialized chromosomal locus that ensures proper segregation of chromosomes during mitotic and meiotic cell divisions. Centromeres are typically composed of large arrays of unrelated tandemly repeated DNAs encompassing several megabase regions that are poorly conserved between species (Lee et al., *Hum. Genet.*, 100:291-304, 1997; Guenatri et al., *J. Cell Biol.*, 166:493-505, 2004; Jiang et al., *Trends Plant. Sci.*, 8:570-575, 2003).

In mouse, two types of repetitive DNA sequences are associated with centromeres. These are the major satellite repeats (approximately 6 megabase arrays of 234 bp per repeat unit) and minor satellite repeats (approximately 600 kb arrays of 120 bp per repeat unit) (Choo, *The Centromere*, Oxford University Press, Oxford, N.Y., Tokyo. 1997) that are distinct from human centromeric repeats. It has been shown that major satellite sequences are located in the pericentromeric region, forming clusters associated with heterochromatin protein 1 alpha, whereas minor satellite sequences coincide with the centric constriction of the centromere and is associated with centromere-specific proteins that are conserved from yeast to mammals (Vissel and Choo, *Genomics*, 5:407-414, 1989; Choo, *The Centromere*, Oxford University Press, Oxford, N.Y., Tokyo. 1997).

The centromeres of human chromosomes are characterized by several megabases (Mb) of alpha-satellite DNA (also known as alphoid DNA), which is composed of a tandem array of a 171 bp repeat unit. Alpha-satellite DNA is the only human centromeric DNA capable of de novo kinetochore formation. A number of groups have shown that alpha-satellite DNA cloned from human chromosomes or generated in vitro supports formation of Human Artificial Chromosomes (HACs) when introduced into cultured cells (Harrington et al., *Nat. Genet.*, 15:345-355, 1997; Ikeno et al., *Nat. Biotechnol.*, 16:431-439, 1998; Willard, *Science*, 290:1308-1309, 2000; Grimes et al., *Mol. Ther.* 5:798-805, 2002; Ohzeki et al., *J. Cell. Biol.*, 159:765-775, 2002; Kouprina et al., *Nucleic Acids Res.*, 31: 922-934, 2003; Basu and Willard, *Trends Mol. Med.*, 11:251-258, 2005; Ebersole et al., *Nuc. Acids Res.*, 33:e130, 2005).

A number of non-alphoid DNA repeats have been also identified in the pericentromeric regions of human chromosomes that flank alpha-satellite DNA arrays. For example, the classical satellites I, II, and III were detected in centromeric regions of human chromosomes 3, 4, 9, 13, 14, 15, 21, and 22 (Gosden et al., *Exp Cell Res.*, 92:148-158, 1975; Vissel et al., *Cytogenet. Cell Genet.*, 61:81-86, 1992; Meyne et al., *Chromosoma*, 103:99-103, 1994). A subset of beta-satellite DNA has been detected in the centromeric region of human chromosome 9 (Waye and Willard, *Proc Natl Acad Sci USA.*, 86:6250-6254, 1989). The centromeric regions of the human acrocentric chromosomes harbor a sn5 satellite DNA (Johnson et al., *Hum Mol Genet.*, 1:741-747, 1992) and gamma-satellite DNA has also been identified in the pericentromeric regions of human chromosomes 8, X, and Y (Lin et al., *Chromosoma*, 102:333-339, 1993; Lee et al., *Chromosoma*, 104:103-112, 1995; Lee et al., *Chromosoma*, 109:381-389, 2000). Gamma-satellite DNA is a tandem array of 220 bp, GC-rich repeating DNA monomers, usually forming 10-200 kb clusters flanked by alpha satellite DNA.

Despite the diversity in size and sequence of centromeric and pericentromeric DNA, the overall architecture and composition of centromeric chromatin is similar in different species. One hallmark of all functional centromeres is the presence of the H3 variant, CENP-A (Sullivan and Karpen, *Nat Struct Mol Biol* 11:1076-1083, 2004; Schueler and Sullivan, *Ann Rev Genomics Hum Genet* 7:301-313, 2006; Lam et al, *Proc Natl Acad Sci USA* 103:4186-4191, 2006; Black et al, *Mol Cell* 25:309-322, 2007). CENP-A is associated with the centromere/kinetochore, the large protein/DNA complex which attaches to spindle microtubes during mitosis and which includes highly homogeneous alpha-satellite DNA in human and minor satellite DNA in mouse. CENP-A nucleosomes represent open chromatin domains in the centromere core. In contrast, flanking pericentromeric DNA consisting of both highly diverged alphoid DNA and non-alphoid DNAs is assembled into heterochromatin lacking CENP-A (Schueler et al, *Science* 294: 109-115 2001; Schueler and Sullivan, 2006; Black et al, 2007).

SUMMARY

Disclosed herein is an analysis of the effect of different centromeric DNA repeats on expression of transgenes targeted into a predetermined chromosomal site. It was surprisingly revealed that the blocks of human gamma-satellite DNA from a pericentromeric region prevent epigenetic transgene silencing. Moreover, gamma-satellite arrays are shown to contain clusters of recognition sites for the transcription factor CTCF that are not sensitive to CpG methylation. Thus, the blocks of pericentromeric gamma-satellite DNAs described herein include insulator nucleic acid sequences, such as CTCT-binding sequences and Ikaros protein-binding sequences, involved in maintenance of mosaic chromatin structure of the human centromere and protection of chromosomal arms from centromeric heterochromatin spreading.

Based on these discoveries, there are now enabled transgene constructs comprising a coding nucleic acid sequence to be expressed in a cell and an insulator nucleic acid sequence, which insulator sequence is derived from gamma satellite DNA. In specific contemplated embodiments, the insulator nucleic acid sequence, which can be operably linked to the transgene, integrates into a chromosomal site. Also provided herein are methods of inhibiting or delaying gene silencing in a cell.

The foregoing and other features and advantages will become more apparent from the following detailed description of several embodiments, which proceeds with reference to the accompanying figures.

BRIEF DESCRIPTION OF THE FIGURES

FIG. 1 illustrates the experimental system used in this study. FIG. 1C is a schematic representation of the re-activation of eGFP transgene expression after excision of silencing vector DNA. FLP recombinase excision of the eGFP transgene from the YAC/BAC vector sequence between the FRT sites in the pYB cassette. FIG. 1D is a digital image of high density MEL cells transfected with silenced eGFP (before excision of the vector backbone sequence) or reactivated eGFP (after excision). After excision, the level of eGFP expression was similar to that of the p212 insert.

FIG. 2 is a schematic drawing of the construction of synthetic DNA arrays for RMCE cassettes. FIG. 2C is a table summarizing synthetic arrays used for the analysis.

FIG. 3 is a series of graphs demonstrating the level of eGFP expression in RL5 cells carrying different transgene cassettes. FIGS. 3A and 3B demonstrate Cre recombinase-mediated cassette exchange (RCME) used to exchange the L1-HYTK-1L cassette at the RL5 locus (chromosome 4) in the MEL cells by pYB cassette containing different repeats. After RMCE, transgenes insert in orientations A or B. eGFP expression was measured in RL5 cells carrying the indicated cassettes in the indicated orientation. Each bar represents measurements of 3-6 independent clones. FIGS. 3C and 3D demonstrate eGFP transgene expression before and after FLP-mediated excision of the vector backbone and repeat sequences. Each bar represents an individual clone. p212 inserts are controls.

FIG. 4 is a series of graphs demonstrating the ChIP analysis of H3K4me2, H3K4me3 and H3K9me3 chromatin in transgene cassettes in RL5 cells. FIG. 4B demonstrates RL5 cells with pYB cassette. Position of the primers: 1—centromeric side of RL5 locus; 2—YAC vector backbone; 3—BAC vector backbone; 5-5' end of the locus control region; 6-eGFP coding region; 7—telomeric side of RL5 locus. FIG. 4C demonstrates RL5 cells with a transgene cassette carrying a 9 kb gamma-satellite DNA. FIG. 4D demonstrates RL5 cells with a transgene cassette carrying a 10 kb human alphoid DNA. Primers for two control loci, the murine β-major globin locus and the murine amylase locus, are presented in Table 7. Position of the primers for cassettes with alpha-(FIG. 4C) and gamma-satellite (FIG. 4D) DNAs: 1 centromeric side of RL5 locus; 2—YAC vector backbone; 3—BAC vector backbone; 4-gamma- or alpha-satellite arrays; 5-5' end of the locus control region; 6—eGFP coding region; 7—telomeric side of RL5 locus.

FIG. 5 is a series of digital images and graphs demonstrating in vitro and in vivo interaction of CTCF with human gamma-satellite DNA. FIG. 5A is a schematic representation of eleven overlapping 8 mer fragments of the human gamma-satellite 8 DNA used in EMSA. EMSA was carried out with either control lysate (−) or lysate containing the in vitro translated 11 ZF DNA binding domain of CTCF protein (+). C; Positive (c-myc promoter) control of the EMSA reaction. FIG. 5C illustrates in vitro interaction of CTCF with mutated forms of gamma-satellite 8 DNA, Mu1, Mu2 and Mu3, with substitution of contact guanines to adenines and with gamma-satellite DNA repeats from chromosomes X and Y. The control is a fragment of the c-myc promoter. FIG. 5D is a graph representing ChIP-real time PCR analysis of gamma-satellite, alpha-satellite, and pYB DNA arrays targeted into the mouse RL5 locus. ChIP analysis was performed three times; averages are shown with standard deviation bars. FIG. 5E is a graph of ChIP-real time PCR analysis of gamma-satellite DNA arrays in human HT1080 cells. Bar graphs show relative enrichment (>1). FIG. 5F is a digital image of the optical mapping on extended chromatin fibers. Extended chromatin fibers were separately stained for CTCF (green), gamma 8 (red), and DAPI (4',6-diamidino-2-phenylindole; blue). Merging the CTCF and gamma 8 images identified areas on the chromatin fibers (yellow) that overlapped between CTCF and gamma 8, showing that CTCF occupies a fraction of the gamma-satellite 8 array.

FIG. 7 is a schematic representation of the physical mapping of the RL5 locus and a scheme of targeting of amplified repeats into the RL5 locus. eGFP transgene expression at the RL5 locus.

FIG. 8 is a schematic representation of the construction of the pYB cassette. FIG. 8A is a schematic drawing of the pYB vector, which was constructed as follows: 5.2 kb XhoI/PstI fragment from the p212 vector containing the human beta-globin LCR 234/promoter driving the eGFP reporter gene (LCR 234-eGFP) was cloned into the pBluescriptII KS vector (Invitrogen). This fragment has two inverted LoxP511 sites (L1 and 1L). FIG. 8B is a schematic drawing of the 'hook' cassette which contains two FRT recognition sites and a MluI internal restriction site. A 300 bp ClaI/ClaI PCR fragment was cloned into the ClaI digested vector from FIG. 8A. The 'Hook' cassette was inserted upstream of LCR 234-eGFP. FIG. 8C is a schematic representation of a 6 kb BAC cassette was inserted into the NotI site of the vector constructed in FIG. 8B.

FIG. 9 is a schematic representation of the eGFP transgene expression at the RL4 locus.

FIG. 10 is a schematic representation of promoter and enhancer activity of gamma-satellite 8 DNA in NIH3T3 cells. The approximately 1.9 kb gamma-satellite 8 DNA fragment was linked to a firefly luciferase reporter gene in a pGL2-basic, promoter, or enhancer vector, and transfected into NIH3T3 cells with the *Renilla* luciferase gene in phRL-CMV as an internal standard. The schematic structures of the vectors are shown in the left panel and the luciferase activities are shown in the right panel. Values are means±SD of three individual experiments in triplicates. Comparison of different constructs did not reveal significant enhancer or promoter activities. Note that in one orientation (−), gamma-satellite DNA exhibits a slight promoter activity. However it cannot explain anti-silencing effect because gamma-satellite arrays have a different orientation (+) in the targeting constructs.

FIG. 11 is a schematic representation of a ChIP assay of chromatin isolated from RL5 cells with the p212 cassette. In FIG. 11A, the p212 cassette is in orientation A. Chromatin was isolated with antibodies against histone H3 lysine 4 Di-methylation and H3 lysine 4 Tri-methylation and analyzed by real time PCR as described in Example 1, below. Position of the primers (as illustrated in the schematic drawing at the top of FIG. 11A): 1—centromeric side of RL5 locus; 2-centromeric side of RL5 locus and HYTK vector backbone region; 3—eGFP coding region; 4—telomeric side of RL5 locus. In FIG. 11B, the p212 cassette is in orientation B. Primers for two control loci, murine β-major globin locus and murine amylase locus, are presented in Table 7. Positions of the primers are as for FIG. 11A, as illustrated in the diagram at the top of FIG. 11A and FIG. 11B.

FIG. 12 is schematic representation of gamma-satellite 8 monomers used for EMSA analysis. FIG. 12A is an alignment of eight monomers forming a repetitive structure in amplified gamma-satellite DNA. Eight full size monomers within an approximately 2 kb repetitive structure are each approximately 220 bp in length and are designated monomer 1 through monomer 8. Only a part of each 220 bp monomer is shown; a full-size sequence of these monomers is available from GenBank Accession No. X68546. Contact "G" (or "C"—for anti-sense strand) nucleotides identified by methylation interference in monomer 8 are boxed in the alignment and are underlined in a consensus sequence of the region. FIG. 12B is a schematic representation of mutations of contact guanine residues in monomer 8 resulting in the lack of in vitro CTCF binding. Positions of mutated nucleotides in sequence variants Mu1, Mu2, and Mu3 are marked in bold. Contact "G" (or "C"—for anti-sense strand) nucleotides are underlined in the wildtype (WT-8) sequence Only a 55 bp core sequence of 100 bp fragments used for EMSA is shown. FIG. 12C is an alignment of eight monomers within a 1.9 kb gamma-satellite array exhibiting an anti-silencing activity.

FIG. 13 is a schematic drawing of an alignment of GSAT, GSATX, GSATII consensus sequences. FIG. 13A demonstrates the consensus sequences that were reconstructed based on comparison of gamma-satellite monomers (FIG. 12). A 15 bp region (positions 95-109 for GSAT consensus) corresponds to the CTCF binding core identified by methylation interference (FIG. 12). The region is conserved between three gamma-satellite subfamilies. FIG. 13B demonstrates the mean identity between gamma-satellite families and the proportions of insertions and deletions (indels) in pairwise alignments (%).

FIG. 14 is a schematic representation of data related to gamma 8 repeats, which help to escape from position effect.

FIG. 15 is an alignment of the mouse major satellite 3 mer used for construction of synthetic arrays. Alignment of three monomers forming a repetitive structure in amplified mouse major satellite DNA is shown. Monomer 1, 2 and 3 are 98% identical and 97% homologous to mouse gamma-satellite DNA, clone 6A (not shown) (GI:193675) described by Vissel and Choo (*Genomics*, 5:407-414, 1989).

FIG. 16 is a schematic and graphic representation of an analysis of gamma-satellite DNA.

SEQUENCE LISTING

Figure 1A:
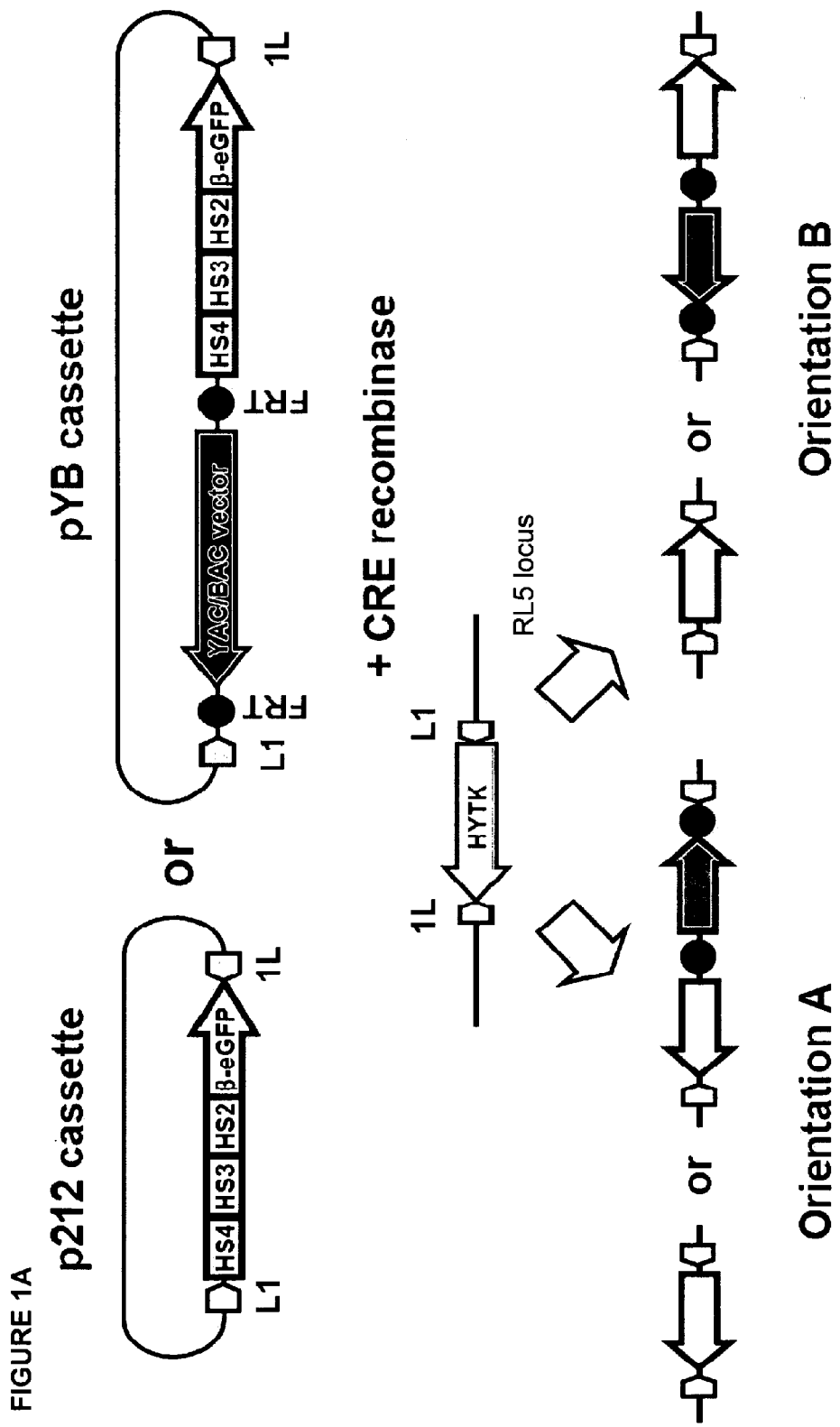
FIG. 1A is a schematic drawing of the Cre recombinase-mediated cassette exchange (RMCE) technique used for the precise replacement of the L1-HYTK-1L cassette at the RL5 locus (chromosome 4) in MEL cells by the p212 (Feng et al., *Mol. Cell. Biol.* 21:298-309, 2001) or pYB cassettes. Both cassettes have the human β globin LCR 234-β-eGFP (enhanced green fluorescent protein) transgene construct and two inverted Lox P sites (L1 and 1L). These sites flank the eGFP transgene in p212. In the pYB cassette, both eGFP and the YAC/BAC vector backbone sequence are exchanged into the target site. The pYB cassette has two recognition sites for FLP recombinase (FRT). After RMCE, transgenes insert in orientations A or B.

The disclosed nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NO: 1 is the consensus nucleic acid CTCF-binding sequence 5'CA/TGGGTGGCNTGGNC 3'.

SEQ ID NOs: 2-134 and 153-163 are primers.

SEQ ID NOs: 135-142 are nucleic acid sequences of gamma satellite 8 monomers. (FIG. 12A).

SEQ ID NOs: 143-146 are nucleic acid sequences of core sequences including mutations of contact guanine residues. (FIG. 12B).

SEQ ID NOs: 147-149 are the consensus nucleic acid sequences of GSAT, GSATX, and GSATII gamma-satellite subfamilies. (FIG. 13A).

SEQ ID NOs: 150-152 are the nucleic acid sequences of three monomers forming repetitive structure in amplified mouse major satellite DNA. (FIG. 15).

Figure 12C:
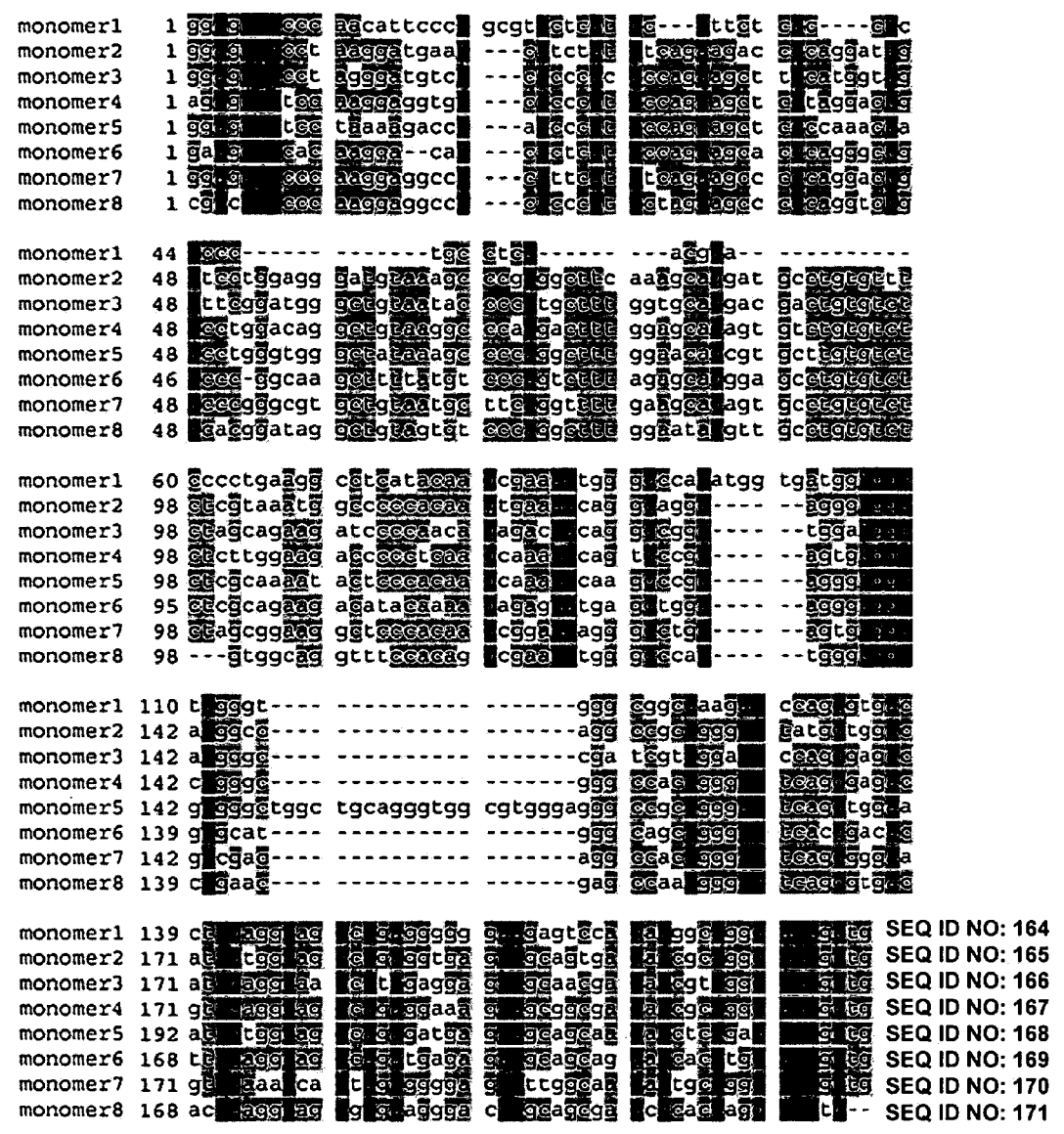

SEQ ID NOs: 164-171 are nucleic acid sequences of eight monomers within a 1.9 kb gamma-satellite array exhibiting an anti-silencing activity (FIG. 12C)

DETAILED DESCRIPTION

I. General Overview

Disclosed herein are transgene constructs and methods of inhibiting gene silencing in a cell. More specifically, provided herein is a construct that includes a coding nucleic acid sequence to be expressed in a cell and a gamma-satellite nucleic acid sequence, wherein the construct integrates into a chromosomal site, thereby inhibiting silencing of the coding nucleic acid sequence.

In one embodiment of the transgene construct, the coding nucleic acid sequence encodes a therapeutic product. In another embodiment, the transgene construct includes an adenoviral or a retroviral sequence. In some embodiments, the transgene construct includes human gamma-satellite DNA from a human chromosome. In particular embodiments, the human gamma-satellite DNA is from chromosome 1, chromosome 8, chromosome 12, chromosome 13, chromosome 21, chromosome 22, chromosome X, or chromosome Y. In one specific non-limiting example, the human gamma-satellite DNA comprises a CTCF binding sequence.

The CTCF binding sequence can include the nucleic acid sequence set forth as SEQ ID NO: 1. In another particular embodiment, the human gamma-satellite DNA comprises an Ikaros protein binding sequence.

Provided herein are methods of inhibiting silencing of a gene in a cell. The methods include introducing into a cell a transgene construct that includes a coding nucleic acid sequence to be expressed in a cell and a gamma-satellite nucleic acid sequence. The cell can be a mammalian cell, for example a human cell.

Also provided herein is an improved method of expressing a coding nucleic acid sequence in a cell using a construct that includes a coding nucleic acid sequence to be expressed in a cell and a gamma-satellite nucleic acid sequence, wherein the improvement includes introducing into the cell a gamma-satellite nucleic acid sequence into a cell and wherein the gamma-satellite nucleic acid sequence integrates into a chromosomal site, thereby inhibiting silencing of the coding nucleic acid sequence.

In particular embodiments of the methods, the transgene construct is introduced into the cell by homologous recombination, recombinase-mediated cassette exchange, microinjection, or a combination of two or more thereof.

II. Abbreviations

AAV adeno-associated vector
Ad adenoviral vector
ADA adenosine deaminase
bp base pairs
CTCF CCCTC-binding factor
eGFP enhanced green fluorescent protein
EMSA electrophoretic mobility shift assay
FACS fluorescence activated cell sort
FRT FLP recombinase
Gpt guanine phosphoribosyl transferase
HAC human artificial chromosome
hisD histidinol dehydrogenase
HIV human immunodeficiency virus
kb kilobase
LCR locus control region
LTR long terminal repeat
Mb megabase
MDR1 multidrug resistance-1
MEL murine erythroleukemia
MuLV murine leukemia virus
PBS phosphate buffered saline
PCR polymerase chain reaction
PNA peptide nucleic acid
RCA rolling circle amplification
RMCE recombinase-mediated cassette exchange
siRNA small inhibitory RNA
SIV simian immunodeficiency virus
UTR untranslatable region
VEGF Vascular Endothelial Growth Factor
YAC yeast artificial chromosome

III. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells.

Cell cycle: An ordered set of events, culminating in cell growth and division into two daughter cells. Non-dividing cells are not considered to be in the cell cycle. The phases of the cell cycle are G1-S-G2-M. The G1 phase represents "GAP 1." The S phase represents "Synthesis." This is the stage when DNA replication occurs. Expressed genes replicate early (first half of S phase) whereas silent genes replicate later. The G2 phase represents "GAP 2." The M phase represents "mitosis", and is when nuclear (chromosomes separate) and cytoplasmic (cytokinesis) division occur.

Centromere: A specialized chromosomal locus that ensures a proper segregation of chromosomes during mitotic and meiotic cell divisions. Centromeres are the dense, specialized portion of a chromosome to which the spindle attaches during mitosis and where the two sister chromatids are joined to one another. Centromeres are typically composed of large arrays of unrelated, tandemly repeated 171 bp alpha-satellite DNA monomers that span for several megabase regions that are poorly conserved between species (Lee et al., *Hum. Genet.*, 100:291-304, 1997; Guenatri et al., *J. Cell Biol.*, 166:493-505, 2004; Jiang et al., *Trends Plant. Sci.*, 8:570-575, 2003).

Centromeric DNA: DNA that comprises the centromere. Of all known human centromeric DNA sequences, alpha-satellite DNA (or alphoid DNA) is the most predominant. A number of non-alphoid DNA repeats have been also identified in the centromeric regions of human chromosomes that flank alpha-satellite DNA arrays. Generally non-alphoid DNA repeats form 10-200 kb clusters that reside within a monomeric type of alpha-satellite DNA arrays located distal to the centromere core.

A subset of beta-satellite DNA has been detected in the centromeric region of human chromosome 9 (Waye and Willard, *Proc Natl Acad Sci USA.*, 86:6250-6254, 1989). The centromeric regions of the human acrocentric chromosomes harbor a sn5 satellite DNA (Johnson et al., *Hum Mol Genet.*, 1:741-747, 1992). Added to this list of repetitive centromeric DNA sequences, gamma-satellite DNA was identified in the centromeric regions of human chromosomes 8, X, and Y (Lin et al., *Chromosoma*, 102:333-339, 1993; Lee et al., *Chromosoma*, 104:103-112, 1995; Lee et al., *Chromosoma*, 109:381-389, 2000). Gamma-satellite DNA was found to consist of 220 bp, GC-rich, tandemly repetitive DNA monomers. There are three families of gamma-satellite DNA in the human genome: GSAT, GSATII, and GSATX. An approximately 200 kb block of gamma-satellite DNA is physically linked with an alpha-satellite array and located at 8q11.1 (Lin et al., *Chromosoma*, 102:333-339, 1993).

Coding nucleic acid sequence: A nucleic acid sequence that encodes a functional molecule. The nucleic acid can encode a protein, such as a therapeutic polypeptide, or a functional nucleic acid sequence, such as an antisense sequence. When transferred to a host cell, such as in gene therapy, a coding nucleic acid sequence can alter the function of the host cell.

CTCF protein: A highly conserved, ubiquitously expressed 11-zinc finger DNA-binding protein (Lobanenkov et al., *Oncogene*, 5:1743-1753, 1990; Filippova et al., *Mol Cell Biol.*, 16:2802-2813, 1996). Via different sets of zinc fingers, CTCF is able to bind divergent CTCF-target sites that mediate multiple activities, including enhancer blocking activity and interchromosomal associations (Ohlsson et al., *Trends Genet.*, 17:520-527, 2001; Ling et al., *Science*, 312:269-272, 2006). Also known as the CCCTC-binding factor, where C is cytosine and T is thymine.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

DNA replication: The use of existing DNA as a template for the synthesis of new DNA strands. In humans and other eukaryotes, replication occurs in the cell nucleus. In mammalian chromosomes, DNA replication begins at multiple initiation regions with an average spacing of 50-150 kb apart, these define replicons. Replication begins at some replication origins earlier in S phase than at others, but the process is completed by the end of S phase.

Euchromatin (euchromatic): Chromosomal material that is genetically active and stains lightly with basic dyes.

Gene therapy (also referred to as Gene transfer): Introduction of a heterologous nucleic acid molecule (transgene) into one or more recipient cells, wherein expression of the heterologous nucleic acid in the recipient cell affects the cell's function and results in a therapeutic effect in a subject. For example, the heterologous nucleic acid molecule may encode a protein that affects a function of the recipient cell. In another example, the heterologous nucleic acid molecule may encode an anti-sense or small inhibitory RNA (siRNA) nucleic acid that is complementary to a nucleic acid molecule present in the recipient cell, and thereby affect a function of the corresponding native nucleic acid molecule. In still other examples, the heterologous nucleic acid may encode a ribozyme or deoxyribozyme, which are capable of cleaving nucleic acid molecules present in the recipient cell. The heterologous nucleic acid may be integrated into a chromosomal site. A chromosomal site can be within the genome of a somatic cell or of a germ cell of an organism, such as a multicellular organism or more particularly a subject (which is thereby rendered transgenic). A chromosomal site can also be within a non-natural chromosome, for example a human artificial chromosome, that is introduced into a cell.

There are generally two types of gene therapy: (1) somatic cell therapy, in which cells other than germ cells are genetically altered, and (2) germ line therapy, in which a replacement gene is integrated into the genome of a subject's gametes or their precursors, or into a non-natural chromosome (for example, an artificial chromosome) that is introduced into the gametes or their precursors, resulting in expression of the new gene in the subject's offspring and subsequent generations. The fundamental difference between germ line gene therapy and somatic cell gene therapy is that germ line gene therapy affects the genetic content of subsequent generations.

Gene therapy can be broadly split in to two categories: ex vivo and in vivo. Recombination-based approaches in vivo are especially uncommon, because for most DNA constructs recombination is a very low probability event. In ex vivo approaches, cells are removed from the subject's body and incubated with vectors that contain inserted copies of the genes. Most gene-therapy vectors are based on viruses, which have evolved a mechanism to encapsulate and deliver their genes to human cells in a pathogenic manner. However, viruses cause problems such as toxicity, immune and inflammatory responses, and gene control and targeting issues. Alternatives to using viruses to deliver genes into cells are being explored, such as directly introducing DNA into cells by microinjection and the development of human artificial chromosomes (HACs) that, when introduced into human cells, would exist autonomously along side the standard 46 chromosomes.

After introduction of the transgene(s), the cells are transplanted back in to the patient where they replicate and produce functional descendants for the life of the patient. In the in vivo approach, the vectors must deliver the genes to enough cells for results to be achieved and they have to remain undetected by the body's immune system.

Genomic DNA: The DNA found within a cell and containing an organism's genome, which is passed on to its offspring as information for continued replication and/or propagation and/or survival of the organism. The term can be used to distinguish between other types of DNA, such as DNA found within plasmids, non-natural chromosomes, or organelles.

Heterochromatin (heterochromatic): Tightly coiled (condensed) chromosomal material that stains deeply during interphase and is genetically inactive. Chromosomal material that becomes genetically inactive and/or condensed undergoes heterochromatinization.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference.

The following is an exemplary set of hybridization conditions and is not limiting:

| Very High Stringency (detects sequences that share at least 90% identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |

| High Stringency (detects sequences that share at least 80% identity) | |
|---|---|
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |

| Low Stringency (detects sequences that share at least 50% identity) | |
|---|---|
| Hybridization: | 6x SSC at RT to 55° C. for 16-20 hours |
| Wash at least twice: | 2x-3x SSC at RT to 55° C. for 20-30 minutes each. |

Ikaros protein: A C2H2 zinc finger protein with expression that is restricted to hematopoietic cells and the pituitary gland. Experiments in knock-out mice established Ikaros as a protein essential for immune response and for normal hematopoiesis of the lymphoid, myeloid, and erythroid lineages (Dijon et al., *Blood* 111: 1138-1146, 2008; Thompson et al., *Immunity* 26(3):335-44, 2007).

Insulator: A cis-acting regulatory sequence that prevents the extension of a heterochromatic region into a euchromatic region when placed at the junction between the two. An insulator acts as a barrier to prevent the advance of nearby condensed chromatin, which has the potential to silence expression of a nearby gene. Insulators are also known as boundary elements. An insulator can also act as an enhancer blocker if situated between an enhancer and a promoter. Such insulators prevent a distal enhancer from activating expression of an adjacent gene, while leaving the enhancer free to stimulate expression of adjacent (unblocked) genes. Insulators control gene expression by protecting genes from inappropriate signals in their environment and by preventing inappropriate interactions between adjacent chromatin domains. One type of insulator establishes domains that separate enhancers and promoters to block their interaction. A second type of insulator creates a barrier against the spread of heterochromatin.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of nucleotides joined by native phosphodiester bonds, between about 4 and about 500 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include PNA molecules.

Particular oligonucleotides and oligonucleotide analogs include linear sequences up to about 300 nucleotides in length, for example a sequence (such as DNA or RNA) that is at least 6 bases, for example at least 8, 10, 15, 20, 25, 30, 35, 40, 45, 50, 100 or even 200 or more bases long, or from about 6 to about 50 bases, for example about 10-25 bases, such as 12, 15, 20, or 25 bases.

Specifically contemplated herein are oligonucleotides that contain one or more modified nucleotides, for instance modified by phosphorylation or the presence of a labeling or other identification molecule (such as, for instance, biotin or another binding agent). By way of example, phosphorylation at the end of oligonucleotides (or pairs of oligonucleotides, hybridized to one another) can facilitate ligation of the oligonucleotide to a blunted end of a nucleic acid molecule.

Operably Linked: A first nucleic acid sequence is operably linked with a second nucleic acid sequence when the first nucleic acid sequence is placed in a functional relationship, or in cis, with the second nucleic acid sequence. Operably linked sequences are in proximity to each other. For instance, an insulator is operably linked to a coding sequence if the insulator affects the transcription or expression of the coding sequence or transgene. An insulator can be operably linked to more than one element and/or nucleic acid sequence, such as a promoter and a coding sequence (or transgene). By way of example, these elements might be right next to (adjacent to) each other. Alternatively, an enhancer element (such as an insulator, a replicator, or a promoter) and a coding sequence might be a large distance away from each other, for instance even greater than 250 kb apart. Other distances include 0.5, 1, 5, 10, 20, 50, 100, 200 kb. Generally, operably linked DNA sequences are contiguous and, where necessary to join two protein-coding regions, in the same reading frame.

Pericentromeric DNA: DNA repeat sequence in the region surrounding the centromere (in the pericentromere). Forms heterochromatin. In contrast to the centromeric region, DNA repeats in the pericentromeric region are diverged.

Probes and Primers: Nucleic acid probes and primers can be readily prepared based on the nucleic acid molecules provided herein, or isolated from libraries generated using the provided methods. It is also appropriate to generate probes and primers based on fragments or portions of these nucleic acid molecules. Also appropriate are probes and primers specific for the reverse complement of these sequences, as well as probes and primers to 5' or 3' regions.

A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (*In Molecular Cloning: A Laboratory Manual*, CSHL, New York, 1989) and Ausubel et al. (In *Current Protocols in Molecular Biology*, John Wiley & Sons, New York, 1998).

Primers are short nucleic acid molecules, for instance DNA oligonucleotides 10 nucleotides or more in length. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand. Optionally, the primer then can be extended along the target DNA strand by a DNA polymerase enzyme. Primer pairs can be used for amplification of a nucleic acid sequence, e.g., by the polymerase chain reaction (PCR) or other in vitro nucleic-acid amplification methods known in the art.

Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs (for instance, for use with polymerase chain reaction amplification) can be derived from a known sequence, for example, by using computer programs intended for that purpose such as Primer (Version 0.5, ©1991, Whitehead Institute for Biomedical Research, Cambridge, Mass.).

One of ordinary skill in the art will appreciate that the specificity of a particular probe or primer increases with its length. Thus, for example, a molecule comprising 30 consecutive nucleotides of a target protein encoding nucleotide will anneal to a target sequence, such as another homolog of the original target protein, with a higher specificity than a corresponding primer of only 15 nucleotides. Thus, in order to obtain greater binding specificity, probes and primers can be selected that comprise at least 20, 23, 25, 30, 35, 40, 45, 50 or more consecutive nucleotides of a protein-encoding nucleotide sequences. These molecules may be obtained from any region of a sequence (for example, a target nucleic acid may be apportioned into halves or quarters based on sequence length, and isolated nucleic acid molecules may be derived from the first or second halves of the molecules, or any of the four quarters, etc.). A cDNA or other encoding sequence also can be divided into smaller regions, for example about eighths, sixteenths, twentieths, fiftieths, and so forth, with similar effect. Another mode of division is to select the 5' (upstream) and/or 3' (downstream) region of a gene.

Promoter: Promoters are sequences of DNA near the 5' end of a gene that act as a binding site for RNA polymerase, and from which transcription is initiated. A promoter includes necessary nucleic acid sequences near the start site of transcription, such as, in the case of a polymerase II type promoter, a TATA element. In one embodiment, a promoter includes an enhancer. In another embodiment, a promoter includes a repressor element. In particular embodiments, a chimeric promoter is created (a promoter/enhancer chimera or a promoter/repressor chimera, respectively). Enhancer and repressor elements can be located adjacent to, or distal to the promoter, and can be located as much as several thousand base pairs from the start site of transcription. Examples of promoters include, but are not limited to the β-globin promoter, SV40 promoter, the CMV enhancer-promoter, the CMV enhancer/β-actin promoter, and the tissue-specific promoters, such as probasin, and promoters that respond to specific transcription factors that are altered in malignancies, such as myc and TP53.

Other promoter sequences which can be used to construct the transgene nucleic acids and practice the methods disclosed herein include, but are not limited to: the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors, any retroviral LTR promoter such as the RSV promoter; inducible promoters, such as the MMTV promoter; the metallothionein promoter; heat shock promoters; the albumin promoter; the histone promoter; the α-actin promoter; TK promoters; B19 parvovirus promoters; the SV10 late promoter; the ApoAI promoter and combinations thereof.

In one embodiment, a promoter is a strong promoter, which promotes transcription of RNA at high levels, for example at levels such that the transcriptional activity of the promoter generally accounts for about 25% of transcriptional activity of all transcription within a cell. The strength of a promoter is often tissue-specific and thus may vary from one cell type to another. For example, CMV is a classic strong promoter because it generates high levels of transcriptional activity in many cell types. Examples of strong promoters include, but are not limited to: CMV; CMV/chicken β-actin; elongation factors 1A and 2A; SV40; RSV; and the MoLV LTR.

In another embodiment, a promoter is a tissue-specific promoter, which promotes transcription in a single cell type or narrow range of tissues. Examples of tissue-specific promoters include, but are not limited to: probasin (which promotes expression in prostate cells), an immunoglobulin promoter; a whey acidic protein promoter; a casein promoter; glial fibrillary acidic protein promoter; albumin promoter; β-globin promoter; and the MMTV promoter.

In yet another embodiment, a promoter is a hormone-responsive promoter, which promotes transcription only when exposed to a hormone. Examples of hormone-responsive promoters include, but are not limited to: probasin (which is responsive to testosterone and other androgens); MMTV promoter (which is responsive to dexamethazone, estrogen, and androgens); and the whey acidic protein promoter and casein promoter (which are responsive to estrogen).

Protein: A biological molecule expressed by a gene or recombinant or synthetic coding sequence and comprised of amino acids, with or without one or more modifications.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Regulatory Sequences or Elements: These terms refer generally to a class of DNA sequences that influence or control expression of genes. Included in the term are promoters, enhancers, locus control regions, boundary elements/insulators, silencers, Matrix attachment regions (also referred to as scaffold attachment regions), repressor, replicators, transcriptional terminators, replication origin, and meiotic recombination hotspots. Promoters are sequences of DNA near the 5' end of a gene that act as a binding site for RNA polymerase, and from which transcription is initiated. Enhancers are control elements that elevate the level of transcription from a promoter, usually independently of the enhancer's orientation or distance from the promoter. Locus control regions (LCRs) confer tissue-specific and temporally regulated expression to genes to which they are linked. LCRs function independently of their position in relation to the gene, but are copy-number dependent. It is believed that they function to open the nucleosome structure, so other factors can bind to the DNA. LCRs may also affect replication timing and origin usage. Insulators are DNA sequence elements that prevent inappropriate interactions between adjacent chromatin domains. One type of insulator establishes domains that separate enhancers and promoters to block their interaction. A second type of insulator creates a barrier against the spread of heterochromatin. Silencers and repressors are control elements that suppress gene expression; they act on a gene independently of their orientation or distance from the gene. Matrix attachment regions (MARs), also known as scaffold attachment regions, are sequences within DNA that bind to the nuclear scaffold. They can affect transcription, possibly by separating chromosomes into regulatory domains. It is believed that MARs mediate higher-order, looped structures within chromosomes. Replicators are genetic elements required for initiation of DNA replication from a particular chromosomal location (see below). Transcriptional terminators are regions within the gene vicinity that RNA polymerase is released from the template. Replication origins (also referred to as initiation regions) are regions of the genome, during DNA synthesis or replication phases of cell division, from which replication forks emanate and from where the replication process of DNA begins. Meiotic recombination hotspots are regions of the genome that recombine more frequently than the average during meiosis.

Sequence Identity: The similarity between two nucleic acid sequences, or two amino acid sequences, is expressed in terms of sequence identity. Sequence identity is frequently measured in terms of percentage identity (or similarity or homology); the higher the percentage, the more similar the two sequences are. Homologs or orthologs of a gene sequence(s) will possess a relatively high degree of sequence identity when aligned using standard methods. This homology will be more significant when the orthologous nucleic acid sequences or genes are derived from species that are more closely related (for example, human and chimpanzee sequences), compared to species more distantly related (for example, human and C. elegans sequences).

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene,* 73: 237-244, 1988; Higgins & Sharp *CABIOS* 5: 151-153, 1989; Corpet et al. *Nuc. Acids Res.* 16, 10881-90, 1988; Huang et al. *Computer Appls. in the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. When aligning short sequences (fewer than around 30 nucleic acids), the alignment can be performed using the BLAST short sequences function, set to default parameters (expect 1000, word size 7).

An alternative indication that two nucleic acid molecules are closely related is that the two molecules hybridize to each other under stringent conditions. Conditions for nucleic acid hybridization and calculation of stringencies can be found in Sambrook et al. (In *Molecular Cloning: A Laboratory Manual*, CSHL, New York, 1989) and Tijssen (*Laboratory Techniques in Biochemistry and Molecular Biology—Hybridization with Nucleic Acid Probes* Part I, Chapter 2, Elsevier, N.Y., 1993).

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

It is recognized that DNA can encode non-protein functional elements. Thus, nucleic acid sequences that do not show a high degree of sequence identity may nevertheless encode similar elements. It is understood that changes in nucleic acid sequence can produce multiple nucleic acid molecules having substantially the same function.

Silencing: Conversion of an actively expressed gene, or construct, to a non-expressed gene, or construct, which occurs without a change in the primary DNA sequence. Transcriptional silencing refers to the inhibition of transcription of a gene, for example a coding nucleic acid sequence. Post-transcriptional silencing refers to silencing at the RNA level and which results in the inhibition of translation, for example by small inhibitory RNAs (siRNAs). In particular embodiments, silencing is the progressive decrease of the expression of a transgene due to heterochromatinization of the transgene-containing region.

Subject: Living multi-cellular vertebrate organisms, particularly a mammal, including human and veterinary subjects, such as cows, pigs, horses, dogs, cats, birds, reptiles, mice, rats, and fish.

Transduced and Transfected: A virus or vector transduces or transfects a cell when it transfers nucleic acid into the cell. A cell is "transfected" by a nucleic acid transduced into the cell when the DNA becomes stably replicated by the cell, either by incorporation (integration) of the nucleic acid into the cellular genome, or by episomal replication.

Transgene Construct: A nucleic acid sequence from one organism introduced into the cell of another. The transgene construct can be integrated into a chromosomal site. A chromosomal site can be within the genome of a somatic cell or of a germ cell of an organism (which is thereby rendered transgenic). A chromosomal site can also be within a non-natural chromosome, for example a human artificial chromosome, that is introduced into a cell. A transgene construct generally includes at least a coding nucleic acid sequence (a sequence encoding a transgene), but can also include regulatory elements, such as promoter, insulator, enhancer, or replicator nucleic acid sequences. A transgene can be a sequence encoding a polypeptide of interest (for example, a therapeutic polypeptide), an antisense RNA, or a small inhibitory RNA (siRNA).

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

IV. Insulator Sequences that Prevent Gene Silencing

Provided herein are insulator sequences in the pericentromeric region of human chromosomes that act as strong insulators in order to inhibit gene silencing over extended periods of time. Thus, transgenes, when operably linked to one of the disclosed insulators, exhibit persistent and stable gene expression over the long term, when compared to constructs containing previously known insulator sequences, or in the absence of an insulator sequence.

In one embodiment, an insulator sequence is pericentromeric-gamma satellite DNA of a chromosome. In particular embodiments, the gamma satellite DNA is from any chromosome, for example, chromosome 1, chromosome 8, chromosome 12, chromosome 13, chromosome 21, chromosome 22, the X chromosome, or the Y chromosome. In some embodiments, gamma satellite DNA is referred to as a heterochromatin arresting repeat element. The gamma satellite DNA can be from any species, for example from human, monkey, pig, sheep, goat, chicken, frog, mouse, hamster, or rat. In other embodiments, the insulator sequence is found on a nucleic acid sequence of about 60 base pairs (bp), 80 bp, 100 bp, 250 bp, 500 bp, 750 bp, 1 kilobase (kb), 1.5 kb, 3 kb, 7 kb, 9 kb, 18 kb, 20 kb, 24 kb, 35 kb, 45 kb, or longer. The insulator sequence can be in segments, arrays, or DNA repeats of pericentromeric gamma satellite DNA. For example, the insulator sequence can be on any number of copies of a monomer of gamma-satellite DNA, such as a monomer of 50, 100, 200, 400, or 600 bp in length. In one embodiment, the monomer is approximately 220 bp in length. The insulator sequence can be included within 1, 2, 3, 4, 5, 6, 7, 8, 9, 10, 20, 50, 75, 100 or more copies of the monomer.

In a particular embodiment, the disclosed gamma satellite insulator sequence includes a CTCF binding site. In another particular embodiment, the gamma satellite insulator sequence is a consensus sequence which includes a CTCF binding sequence. In one specific non-limiting example, the consensus sequence is as follows: 5' C<u>A</u>/TGGGTGG C<u>N</u>TGGNC 3' (SEQ ID NO: 1), where the nucleic acid residue at position 2 of the consensus sequence either can be an adenine or a thymine and the nucleic acid residue at positions 10 and 14 either can be adenine, cytosine, guanine, or thymine (the contact nucleotides are bold and underlined). This consensus sequence was generated using sequences from eight gamma satellite DNA monomers from chromosome 8, which were shown to bind the CTCF protein in vitro. In another particular embodiment, the disclosed gamma satellite insulator sequence includes an Ikaros protein recognition or binding site (Cobb et al., *Genes & Dev.*, 14:2146-2160, 2000).

Variant insulator sequences are also envisioned and may be produced by standard DNA mutagenesis techniques, including without limitation M13 primer mutagenesis. Variant insulator sequences may have one or more point mutations, deletions, truncations, or additions. Details of these techniques are provided in Sambrook et al., *Molecular Cloning: A Laboratory Manual*, New York: Cold Spring Harbor Laboratory Press, 1989, Ch. 15. By the use of molecular engineering techniques well known in the art, variants may be created that differ from the insulator nucleic acid sequences disclosed. Also comprehended by this disclosure are DNA molecules and nucleotide sequences that are derivatives of those specifically described herein, and which differ from those disclosed by the deletion, addition, or substitution of nucleotides, while retaining (i) the ability to act as a barrier to prevent the advance of nearby condensed chromatin which has the potential to silence expression of the gene, or (ii) the ability to bind CTCF or Ikaros protein. Gamma satellite DNA that does not express enhancer blocking activity or does not act as a barrier insulator because it does not flank both 5' and 3' ends of the transgene in order to prevent silencing epigenetic silencing, is referred to herein as a heterochromatin arresting repeat element. Also disclosed are closely related nucleic acid molecules that share at least 80%, at least 85%, at least 90%, at least 95%, at least 96%, at least 97%, at least 98%, or at least 99% nucleotide sequence identity with the insulator nucleic acid sequences described herein. Alternatively, related nucleic acid molecules can have no more than about 3, 5, 10, or 20 nucleic acid changes compared to the disclosed insulator sequences. When the variant insulator sequences include DNA repeats, the related nucleic acid molecules can have larger numbers of nucleic acid changes, for example, no more than about 50, 75, 100, 200, 300, 400, or 500 nucleic acid changes, compared to DNA repeats including the disclosed insulator sequences.

Nucleic acid molecules that are derived from the insulator sequences include molecules that hybridize under stringent conditions to the disclosed insulator nucleic acid sequences, or fragments thereof. Useful hybridization conditions are described above. Methods are provided herein for determining the function of variants or derivatives of the disclosed insulator sequences. The disclosed methods, such as the method described in Example 1, demonstrate the function of the insulator sequences, and variants and derivatives thereof.

V. Methods of Inhibiting Gene Silencing

Successful gene therapy strategies require persistent and stable transgene expression in a specific target cell lineage. However, the expression of integrated transgenes is subject to the epigenetic effects of surrounding chromatin. Such position effects can lead to transgene silencing or expression variegation, which is often associated with changes in the chromatin structure of transgenes. Thus, gene silencing is a major impediment in gene therapy and a need exists for developing methods of inhibiting gene silencing. Disclosed herein are methods of preventing, delaying, or inhibiting gene silencing in a cell using the disclosed insulator sequences or, in some embodiments, a heterochromatin arresting repeat element.

The disclosed insulator nucleic acid sequence, when operably linked to another nucleic acid sequence, such as a coding nucleic acid sequence, is capable of preventing, delaying, or inhibiting the silencing of the nucleic acid sequence (transgene). In addition, the disclosed insulator sequence regulates transcription of an operably linked nucleic acid sequence for extended periods of time.

The disclosed methods include introducing into a cell of interest a transgene construct which includes the disclosed insulator nucleic acid sequence (which in one embodiment comprises the 5' CA/TGGGTGGCNTGGNC 3' consensus sequence; contact nucleotides are bold and underlined; SEQ ID NO: 1) operably linked with (in the proximity of) a coding nucleic acid sequence to be expressed in the cell. Such a construct, when incorporated (integrated) into a chromosomal site, will delay or prevent silencing of expression of the transgene. In some embodiments, such a construct is integrated into a host genome. In other embodiments, such a construct is integrated into a non-natural chromosome, for example a human artificial chromosome (International Application Nos. PCT/US02/10990 and PCT/US2006/013362), that is introduced into the cell. In particular embodiments, an insulator nucleic acid sequence is introduced in the proximity of a silenced coding sequence (e.g., integrated into proximal or adjacent sequence), thereby inhibiting or reversing silencing and allowing for expression of the coding sequence. The insulator sequence can be introduced into a chromosomal site simultaneously with the transgene sequence or following the integration of the transgene sequence. The sequences can be integrated randomly into a chromosomal site or can be specifically targeted to a chromosomal site using integration sites, for example a Lox-P site.

Silencing of a coding sequence, gene, or transgene, can be inhibited, delayed, or prevented by the disclosed methods and compositions. Thus, disclosed methods and compositions extend the length of time that a gene or transgene is expressed. For example, the disclosed methods and compositions can delay or inhibit the initiation of silencing of a gene or transgene. The duration of the anti-silencing effect of the insulator sequence can be for at least about 1 month, about 3 months, about 6 months, about 1 year, about 2 years, about 5 years, about 10 years, or for the life of the subject. In other embodiments, the level of expression of the gene or transgene is increased when using the disclosed methods and compositions, compared to methods and compositions lacking the disclosed insulator nucleic acid sequence. Under any of the above conditions, the level or duration of expression the gene or transgene construct in the proximity of an insulator sequence is increased, compared to expression levels and duration of expression in the absence of an insulator sequence.

In one particular embodiment, the introduction (integration) of the disclosed insulator sequence in the proximity of a silenced gene or transgene construct inhibits silencing 100% and expression of the gene or transgene construct is increased by 100%, compared to the same gene or transgene construct in the absence of a disclosed insulator sequence. In other embodiments, the introduction of a disclosed insulator sequence in the proximity of a silenced (or silence-prone) gene or transgene construct inhibits silencing at least 99%, at least 95%, at least 90%, at least 85%, at least 80%, at least 75%, at least 65%, at least 55%, at least 50%, or at least 45%, such that expression of the gene, or transgene construct, is increased by at least 99%, at least 95%, at least 90%, at least 85%, at least 80%, at least 75%, at least 65%, at least 55%, at least 50%, or at least 45%, respectively. In other embodiments, the introduction (integration) of a transgene construct containing the disclosed insulator sequence and a coding nucleic acid sequence prevents or delays silencing of the coding nucleic acid sequence by 100%. In further embodiments, the introduction of a transgene construct containing the disclosed insulator sequence and a coding nucleic acid sequence prevents or delays silencing of coding nucleic acid sequence by at least 99%, at least 95%, at least 90%, at least 85%, at least 80%, at least 75% at least 65%, at least 55%, at least 50%, or at least 45%, compared to the same transgene construct in the absence of the insulator sequence.

Examples of the disclosed methods use insulator sequences that include all or any portion of any insulator nucleic acid from any species, for example, human, monkey, goat, pig, sheep, chicken, frog, mouse, rat, or hamster.

VII. Transgenes and Transgene Constructs

The disclosure provides for transgene constructs where a disclosed insulator sequence or, in some embodiments, a heterochromatin arresting repeat element, and a coding nucleic acid sequence (a sequence that encodes a transgene) are placed in any orientation with respect to each other, for example, either downstream (for instance, 3') or upstream (for instance, 5') of each other. In one embodiment, at least one disclosed insulator sequence is located downstream (for instance, 3') of the coding nucleic acid sequence. In other embodiments, at least one disclosed insulator is located upstream (for instance, 5') of the coding nucleic acid sequence.

The insulator sequence and coding nucleic acid sequence may be separated by any number of nucleotides as long as the prevention, delay, or inhibition of silencing of the coding nucleic acid sequence described herein is observed. For example, there may be at least about 2, at least about 5, at least about 10, at least about 20, at least about 50, at least about 75, at least about 100, at least about 250, at least about 500, at least about 1000, at least about 2000 nucleotides separating the insulator sequence and the coding sequence. In other embodiments, there may be at least about 3, 5, 7, 10, 12, 15, 20, 25, 50, 75, 100, 200, 500, 1000, or more kilobases (kb) separating the insulator sequence and the coding sequence. Conventional transgene constructs can include up to 15 kb of DNA sequences, but longer sequences (hundreds of kb) can be inserted in mammalian cells via the use of viral vectors, such as adenoviruses, or by creating artificial human chromosomes. In some embodiments, insertions of long sequences are necessary.

Other sequences can be included in the transgene construct. For example, any regulatory element or sequence encoding a selectable marker can be included in the transgene construct. In one embodiment, the transgene construct includes a promoter sequence. In other embodiments, the transgene construct includes a selectable marker sequence, or both a promoter and a selectable marker sequence.

Nucleic acid sequences encoding any one of a variety of selectable markers can be included in the transgene construct. For example, a sequence encoding a selectable marker which confers a selectable phenotype such as drug resistance, nutritional auxotrophy, resistance to a cytotoxic agent or expression of a surface protein, can be used. Selectable marker genes which can be used include green fluorescent protein (GFP), neomycin, guanine phosphoribosyl transferase (gpt), DHFR, adenosine deaminase (ADA), blasticidin, kanamycin, hygromycin, multidrug resistance-1 (MDR1), and histidinol dehydrogenase (hisD). The selectable phenotype conferred makes it possible to identify and isolate the cells containing the transgene. Selectable markers can be divided into two categories: positive selectable and negative selectable. In positive selection, cells expressing the positive selectable marker are capable of surviving treatment with a selective agent (such as neomycin, gpt, DHFR, ADA, hygromycin, MDR1 and hisD) or can be separated from cells that do not express the selectable marker (GFP). In negative selection, cells expressing the negative selectable marker are destroyed in the presence of the selective agent (for example, thymidine kinase, gpt).

A variety of promoters can be included in the transgene construct. Examples of promoters include, but are not limited to the SV40 promoter, the CMV enhancer-promoter, the CMV enhancer/β-actin promoter, and the tissue-specific promoters β-globin and probasin. Other promoter sequences which can be used to when designing the transgene construct and practice the methods disclosed herein include, but are not limited to: the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors, any retroviral LTR promoter such as the RSV promoter; inducible promoters, such as the MMTV promoter; the metallothionein promoter; heat shock promoters; the albumin promoter; the histone promoter; the α-actin promoter; TK promoters; B19 parvovirus promoters; the SV10 late promoter; the ApoAI promoter and combinations thereof.

The disclosed transgene constructs contain at least one insulator sequence, which can be operably linked with other elements. The elements may be additional cis-acting elements, for example sequences including AT-rich sequences, matrix attachment sites, CpG islands, transcription initiators, transcription terminators, a start codon (for instance, ATG) preceding a protein-encoding nucleic acid sequence, splicing signal for introns, maintenance of the correct reading frame of that nucleic acid sequence to permit proper translation of mRNA, and stop codons. Generally, auxiliary expression control sequences will include the minimal sequence sufficient to support transcription.

In certain embodiments, a transgene construct includes a nucleic acid sequence (transgene; coding nucleic acid sequence) encoding a polypeptide of interest. A transgene of interest can encode a polypeptide that affects a function of the transformed or transfected cell. The encoded polypeptides include, but are not limited to, therapeutic polypeptides. Specific, non-limiting examples of a transgenes of interest include the genes that encode α-globin, β-globin, Vascular Endothelial Growth Factor (VEGF), blood factors (such as Factors VIII and IX), insulin, BRCA1, BRCA2, BORIS (Brother Of the Regulator of Imprinted Sites), ASPM (Abnormal, spindle-like, microcephaly-associated), parkin, genes of lysosomal storage diseases (such as β-glucocerebrosidase and β-hexosaminidase A), HD (Huntington Disease), and adenosine deaminase. Other non-limiting examples of a transgene of interest include antisense RNA and siRNA (small inhibitory RNA) sequences directed against harmful sequences. Continual expression of antisense RNA and siRNA sequences directed against, for example HIV-related genes, inhibits expression of proteins encoded by the corresponding sequences. In particular embodiments, stable expression of these transgene sequences prevent HIV replication.

The encoded polypeptide can also be a marker polypeptide, which is used to identify a cell of interest. Marker polypeptides include fluorescent polypeptides, enzymes, or antigens that can be identified using conventional molecular biology procedures. For example, the polypeptide can be a fluorescent marker (for example, green fluorescent protein, *Aequorea Victoria*, or *Discosoma* DSRed), an antigenic markers (for example, human growth hormone, human insulin, human HLA antigens), a cell surface marker (for example, CD4, or any cell surface receptor), or an enzymatic marker (for example, lacZ, alkaline phosphatase). Techniques for identifying these markers in host cells include immunohistochemistry, fluorescent-activated cell sorting (FACS), and fluorescent microscopy, and are well known in the art. In other embodiments, the expression vector may include a polylinker (for instance, a multiple cloning site) to permit insertion of a nucleic acid sequence encoding a polypeptide of interest.

RNA molecules transcribed from an expression vector need not always be translated into a polypeptide to express a functional activity. Specific non-limiting examples of other molecules of interest include antisense RNA molecules complementary to an RNA of interest, ribozymes, small inhibitory RNAs, and naturally occurring or modified tRNAs.

Transgene constructs including an insulator, alone or operably linked to a coding nucleic acid sequence, can be used to transform host cells. Hosts can include isolated yeast, insect, and mammalian cells, as well as cells located in the organism.

In some embodiments the host cells are eukaryotes. Biologically functional viral and plasmid DNA vectors capable of expression and replication in a host are known in the art, and can be used to transfect cells of interest.

VII. Gene Transfer of a Transgene Construct Containing an Insulator Sequence Conventional viral and non-viral based gene transfer methods can be used to introduce the transgenes or transgene constructs disclosed above (that include an insulator nucleic acid sequence or, in some embodiments, a heterochromatin arresting repeat element, either alone or in combination with a coding nucleic acid sequence) in mammalian cells or target tissues (see for example, U.S. Pat. Nos. 6,846,676, 6,537,542, 6,933,113 and U.S. Patent Application Publication No. US20040132683). Such methods can be used to administer the disclosed constructs to cells in vitro. In one embodiment, the disclosed construct is administered for in vivo or ex vivo gene therapy uses. Non-viral vector systems to deliver the disclosed transgene constructs include DNA plasmids, naked nucleic acid, artificial chromosomes, and nucleic acid complexed with a delivery vehicle such as a liposome. Viral vector delivery systems include DNA and RNA viruses, which have either episomal or integrated genomes after delivery to the cell. The transgene construct, including the insulator sequence, can be integrated into a chromosomal site, for example the genome of a cell (for instance a somatic cell or a germ cell of an organism) or a non-natural chromosome (for instance, an artificial chromosome). Gene transfer using the transgene construct, including the insulator sequence, can be used to treat any one of a number of diseases, for example hematopoietic diseases such as hemophilia, thalassemia, sickle cell, and other hemoglobinopathies, lysosomal storage diseases, and Huntington Disease.

Methods of non-viral delivery of the disclosed transgene constructs include lipofection, microinjection, biolistics, virosomes, liposomes, immunoliposomes, polycation or lipid:nucleic acid conjugates, naked DNA, artificial virions, and agent-enhanced uptake of DNA. Lipofection is described in for example, U.S. Pat. Nos. 5,049,386, 4,946,787; and 4,897,355 and lipofection reagents are sold commercially (for example, Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art.

The use of RNA or DNA viral based systems for the delivery of the disclosed transgene constructs takes advantage of highly evolved processes for targeting a virus to specific cells in the body and trafficking the viral payload to the nucleus. Viral vectors can be administered directly to the subject (in vivo) or they can be used to treat cells in vitro and the modified cells are then administered to a subject (ex vivo). Conventional viral based gene transfer systems for the delivery of a nucleic acid construct encoding an insulator, either alone or in combination with a transgene, include retroviral, lentiviral, adenoviral, adeno-associated, and herpes simplex virus vectors. Viral vectors are currently the most efficient and versatile method of gene transfer in target cells and tissues. Integration into a chromosomal site, for example in a host genome or in a non-natural chromosome, is possible with the retrovirus, lentivirus, and adeno-associated virus gene transfer methods. Additionally, high transduction efficiencies have been observed in many different cell types and target tissues.

The sequence of a retrovirus can be altered by incorporating foreign envelope proteins, thereby expanding the potential population of target cells. Lentiviral vectors are members of a class of retroviral vector that is able to transduce or infect non-dividing cells and typically produce high viral titers. Selection of a retroviral gene transfer system would therefore depend on the type of target tissue. Retroviral vectors are comprised of cis-acting long terminal repeats (LTRs) with packaging capacity for up to 6-10 kb of foreign sequence. The minimum cis-acting LTRs are sufficient for replication and packaging of the vectors, which are then used to integrate the therapeutic transgene into the target cell. Widely used retroviral vectors include those based upon murine leukemia virus (MuLV), gibbon ape leukemia virus (GaLV), Simian Immunodeficiency virus (SIV), human immunodeficiency virus (HIV), and combinations thereof. Construction of recombinant lentiviral vectors is well known to those of skill in the art (Zufferey et al., *J. Virol.,* 72:9873-9880, 1998; Lois et al., *Science,* 295, 868-872, 2002).

In other embodiments, an adenoviral based system is used. Adenoviral based vectors are capable of very high transduction efficiency in many cell types and do not require cell division. This vector can be produced in large quantities in a relatively simple system. Adeno-associated virus ("AAV") vectors are also used to transduce cells with target nucleic acids, for example, in the in vitro production of nucleic acids and peptides, and for in vivo and ex vivo gene therapy procedures. Construction of recombinant AAV vectors is well known to those of skill in the art (Flotte et al. *Proc. Natl. Acad. Sci. USA,* 90:10613-10617, 1993; Snyder et al., *Nature Med.,* 5:64-70, 1999; Chatterjee et al., *Blood,* 93:1882-1894, 1999).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system.

Replication-deficient recombinant adenoviral vectors (Ad) can be produced at high titer and they readily infect a number of different cell types. Ad vectors can transduce multiple types of tissues in vivo, including non-dividing, differentiated cells such as those found in the liver, kidney and muscle system tissues. Conventional Ad vectors have a large carrying capacity.

Packaging cells are used to form virus particles that are capable of infecting a host cell. Such cells include 293 cells, which package adenovirus, and psi.2 cells or PA317 cells, which package retrovirus. Viral vectors used in gene transfer are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line.

Transgene constructs can be delivered in vivo by administration to a subject, typically by systemic administration (for example, intravenous, intraperitoneal, intramuscular, subdermal, or intracranial infusion) or topical application, as described below. Alternatively, constructs can be delivered to cells ex vivo, such as cells explanted from a subject (for example, lymphocytes, bone marrow aspirates, tissue biopsy)

or universal donor hematopoietic stem cells, followed by re-implantation of the cells into a subject, usually after selection for cells which have incorporated the vector.

Ex vivo cell transfection for diagnostics, research, or for gene transfer (for example, via re-infusion of the transfected cells into the host organism) is well known to those of skill in the art. In one embodiment, cells are isolated from the subject, transfected with the disclosed constructs, and re-infused back into the subject. Various cell types suitable for ex vivo transfection are well known to those of skill in the art. In one embodiment, stem cells, such as embryonic stem cells, are used in ex vivo procedures for cell transfection and gene transfer. The advantage to using stem cells is that they can be differentiated into other cell types in vitro, or can be introduced into a subject where they will engraft in the bone marrow. Methods for differentiating CD34+ cells in vitro into clinically important immune cell types using cytokines such a GM-CSF, IFN-gamma and TNF-alpha are well known.

Stem cells are isolated for transduction and differentiation using known methods. For example, hematopoietic or erythroid stem cells are isolated from other bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells).

Viral vectors (for example, retroviruses, lentiviruses, adenoviruses, liposomes, etc.) containing the disclosed constructs, also can be administered directly to the organism for transduction of cells in vivo. Alternatively, naked DNA can be administered.

Viral vectors containing the disclosed transgene constructs, including insulator sequences, can be administered directly to the patient for modulation of gene expression and for therapeutic or prophylactic applications directed against, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. Administration of therapeutically effective amounts is by any of the routes normally used for introducing transgene constructs into the tissue to be treated. The vectors are administered in any suitable manner, preferably with pharmaceutically acceptable carriers. Suitable methods of administering such vectors are available and well known to those of skill in the art, and, although more than one route can be used to administer a particular composition, a particular route can often provide a more immediate and more effective reaction than another route.

VII. Pharmaceutical Compositions

The compositions, including particularly the disclosed insulator sequences or, in some embodiments, a heterochromatin arresting repeat element, can be used therapeutically in combination with a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions that are available (see, for example, *Remington's Pharmaceutical Sciences*, 17$^{th}$ ed. 1985)). These most typically would be standard carriers for administration of drugs to mammalian subjects such as humans, including solutions such as sterile water, saline, and buffered solutions at physiological pH.

The vectors including the disclosed constructs can be made into aerosol formulations (for instance, they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. An appropriate amount can be determined by one of ordinary skill in the art using only routine experimentation given the teachings herein.

Parenteral administration of the composition, if used, is generally characterized by injection. Injectable compositions can be prepared in conventional forms, either as liquid solutions or suspensions, solid forms suitable for solution of suspension in liquid prior to injection, or as emulsions. More recently approaches for parenteral administration involve use of a slow release or sustained release system such that a constant dosage can be maintained.

The materials may be in solution or suspension (for example, incorporated into microparticles, liposomes, or cells). These may be targeted to a particular cell type via antibodies, receptors, or receptor ligands. The following references provide examples of the use of such technology to target specific proteins to tumor tissue (Senter et al., *Bioconjugate Chem.*, 2:447-451, 1991; Bagshawe, Br. *J. Cancer,* 60:275-281, 1989; Bagshawe et al., *Br. J. Cancer,* 58:700-703, 1988; Senter et al., *Bioconjugate Chem.,* 4:3-9, 1993; Battelli et al., *Cancer Immunol. Immunother.,* 35:421-425, 1992; Pietersz and McKenzie, *Immunolog. Reviews,* 129:57-80, 1992; and Roffler, et al., *Biochem. Pharmacol,* 42:2062-2065, 1991). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references provide examples of the use of such technology to target specific proteins to tumor tissue (Hughes et al., *Cancer Research,* 49:6214-6220, (1989); and Litzinger and Huang, *Biochimica et Biophysica Acta,* 1104:179-187, 1992). In general, receptors useful as targets for this type of delivery are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (see, for instance, Brown and Greene, *DNA and Cell Biology* 10:6, 399-409, 1991).

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, flavor maskers, diluents, emulsifiers, dispersing aids or binders may be desirable.

The invention is illustrated by the following non-limiting Examples.

EXAMPLES

Example 1

Human Pericentromeric Gamma-Satellite DNA Binds CTCF and Protects a Transgene from Epigenetic Silencing This example describes methods comparing anti-silencing and heterochromatin maintenance potentials of centromere-associated DNA repeats. This includes in vivo construction of arrays consisting of common centromeric repeats combined with a reporter gene and targeting them into a predetermined chromosomal site in the mouse genome to quantitatively evaluate the level and stability of the transgene expression. This new approach clarifies the link between different types of centromeric DNA repeats and distinctive types of chromatin in the human centromere.

Construction of Synthetic DNA Repeats and a Vector Used for Modification of the RMCE System Construction of synthetic DNA repeats by rolling-circle amplification and recombinational cloning in yeast was previously described (Ebersole et al., *Nucleic Acids Research*, 33, e130 2005; PCT Application No. PCT/US2006/013362). The sources of DNA repeats, as well as the primers, are described in Tables 1-3. A sequence of the 3-mer of mouse major satellite DNA used for the construction of arrays is approximately 97% identical to mouse gamma satellite DNA, clone 6A (GI: 1936750) and is available from GenBank (Accession No. EF028077). Construction of the pYB targeting cassette is described in FIG. 8 and Tables 4 and 5.

TABLE 1

Size of synthetic arrays generated from different types of repeats

| Name of repeat | Number of repeats | Size of unit (in kb) | Size of array (in kb) | Fold increase |
|---|---|---|---|---|
| Mouse | | | | |
| Major satellite | 3 mer | 0.7 | 7, 10, 20, 35, 45 | x10, x14, x28, x50, x64 |
| Human | | | | |
| α21-1 alphoid | 11 mer | 1.8 | 10, 18, 35 | x5.5, x10, x19 |
| Gamma 8 | 9 mer | 1.9 | 3, 9, 15, 24 | x1.5, x5, x8, x12 |

TABLE 2

Primers used for PCR amplification of repeats

| Name | Primer sequence | Size of PCR product | Number of repeat units |
|---|---|---|---|
| Mouse major F | 5' acgtgaattctggcgaggaaaactgaaaaaggtg 3' (SEQ ID NO: 2) | 704 bp* | 3 |
| Mouse major R | 5' gccagaattcacgtcctaaagtgtgtatttctca 3' (SEQ ID NO: 3) | | |
| Gamma8 repeat F | 5' cgatgaaggcctctccgatcct 3' (SEQ ID NO: 4) | 1,962 bp* | 8 |
| Gamma8 repeat R | 5' gaaagtcctggggcttctgga 3' (SEQ ID NO: 5) | | |
| HS4 1copy F | 5' gatcactagtgagctcacggggacagcc 3 (SEQ ID NO: 6)' | 278 bp | 1 |

TABLE 2-continued

Primers used for PCR amplification of repeats

| Name | Primer sequence | Size of PCR product | Number of repeat units |
|---|---|---|---|
| HS4 1copy R | 5' gatctctagactctctttcagcctaaagct 3' (SEQ ID NO: 7) | | |
| HS4 2copy F | 5' gatcggccggccagtgtgctggaattcgccct 3' (SEQ ID NO: 8) | 572 bp | 2 |
| HS4 2copy R | 5' gatcggccggcctgtgatggatatctgcagaat 3' (SEQ ID NO: 9) | | |

*All repeats were PCR amplified from genomic DNA and sequenced. Size of fragments cloned in TA vector is shown.

TABLE 3

Thio-phosphate linked primers used for RCA amplification of repeats

| Name | | Primer sequence |
|---|---|---|
| Mouse major | MRCA F1: | 5' acttgacGA 3' (SEQ ID NO: 10) |
| | MRCA F2: | 5' tgcacactGA 3' (SEQ ID NO: 11) |
| | MRCA R2: | 5' cgccatatTC 3' (SEQ ID NO: 12) |
| Human Gamma 8 | GRCA F1: | 5' aattctgGG 3' (SEQ ID NO: 13) |
| | GRCA R1: | 5' ttaagacCC 3' (SEQ ID NO: 14) |
| | GRCA R2: | 5' cctccacAG 3' (SEQ ID NO: 15) |

Each primer was linked by Thio-phosphate through the last two oligomers.

TABLE 4

Primers used for pYB vector construction

| Name | Forward primer | Reverse primer |
|---|---|---|
| Cla Rsr alphoid | 5'gttacctatcgatatcgga ccgtctagacagaagcattct cagaaactt 3' (SEQ ID NO: 16) | 5'tgtcggatcgattacgg accgatgtgaagatattcc cgtttccaac 3' (SEQ ID NO: 24) |
| Mlu Rsr | 5'atgactacgcgtaaacact cttttttgtagaatctgcaag 3' (SEQ ID NO: 17) | 5'catggtaacgcgtctgc tctatcaaaaggaaggttc aact 3' (SEQ ID NO: 25) |
| Frt alphoid | 5'cctatactttctagagaat aggaacttctggccggcccg gaccg 3' (SEQ ID NO: 18) | 5'attctctagaaagtata ggaacttcgacgtcagcgg ccgcacggaccgatgtgaa gatattcccgtttccaac 3' (SEQ ID NO: 26) |
| Cla Frt | 5'gttactatcgatagaagtt cctatactttctagagaatag gaacttcg 3' (SEQ ID NO: 19) | 5'tgtcggatcgatagcta gcaaccgcggtgaagttcc tattctctagaaagtatag gaacttcg 3' (SEQ ID NO: 27) |
| YAC cassette | 5'cgcagcggccgcatctgtg cggtatttcacaccgc 3' (SEQ ID NO: 20) | 5'atgcgcggccgccgaaa agtgccacctgggtcc 3' (SEQ ID NO: 28) |
| BAC cassette | 5'tatgtcgacatcggatgca gcccggttaa 3' (SEQ ID NO: 21) | 5'ttgtggttgtccaaac tcatcaatg 3' (SEQ ID NO: 29) |
| Kan$^R$ gene | 5'gatcgtcgactgaaagcca cgttgtgtctc 3' (SEQ ID NO: 22) | 5'gatcgggccctcccgtc aagtcagcgtaat 3' (SEQ ID NO: 30) |

TABLE 4-continued

Primers used for pYB vector construction

| Name | Forward primer | Reverse primer |
|---|---|---|
| PUC linker | 5'gatcacgcgtactgatgca tgatccggggtt 3' (SEQ ID NO: 23) | 5'gatcacgcgtactgatg catgatccggggtt 3' (SEQ ID NO: 31) |

TABLE 5

Targeting hook sequences

| Name of hook | Hook sequence | Product size |
|---|---|---|
| Mouse major 5' | 5'gatccggaccgatggcgaggaaaactgaa aaaggtggaaaatttagaaatgtccactgta ggacgtggaatatggcaagaaaactgaaaat catggaaaatgagaaacatccacttgacgaa cgcgtgatc 3' (SEQ ID NO: 32) | 131 bp |
| Mouse major 3' | 5'gatcacgcgttgaaaaatgacgaaatcac taaaaacgtgaaaaatgagaaatgcacactg aaggacctggaatatggcgagaaaactgaaa atcacggaaaatgagaaatacacactttagg acgtgcggaccggatc 3' (SEQ ID NO: 33) | 138 bp |
| Gamma8 repeats 5' | 5'gatccggaccgactatggtggacattgtg gtcaggcagaggtgagaagacagtgagaccg cagggaatgctgggagcctcctagggatgtc tctcccaccccagaagcttaccatngtgtt tcggatgggctgtaatacccccatgctttggt acgcgtgatc 3' (SEQ ID NO: 34) | 163 bp |
| Gamma8 repeats 3' | 5'gatcacgcgtgtagagggaagaattggca agactgcagggtaatgctgcgaccctcccaa ggagagcctctcccatcctagaagcccccca ggtctgtcacggataggctgtagtgtcggac cggatc 3' (SEQ ID NO: 35) | 128 bp |
| Human alpha satellite* 5' and 3' | 5'atgcatcgataagagtgtttcaaaactgc tctatcaaaaggaatgttcaACGCGTgagtt gaatgcaaacttcacaaagaagtttctgaga atgctcgaggcatgcat 3' (SEQ ID NO: 36) | 108 bp |

Restriction sites were introduced into 5' ends of the primers to simplify cloning into pYB vector.
*Alpha satellite sequence contains a native MluI site (marked in capital). Digestion with MluI enzyme produces two hooks of ~40 bp each.

A modified Cre expression plasmid was constructed using iCre (Shimshek et al., *Genesis,* 32:19-26, 2002), a mammalian codon optimized Cre variant (R. Sprengel). An iCre PCR product with NcoI/NheI terminal sites was inserted into the NcoI/NheI sites of pCpG-lacZ (Invivogen, Quebec, Canada) resulting in replacement of LacZ. The pCpG-iCre expression plasmid, with no CpG sites in promoter or vector sequences and MAR elements flanking the iCre gene, generally gave improved efficiency in recovery of targeted recombinants in the mouse MEL/RL5 cells. The pCAGGS-FLP vector was purchased from GeneBridges (Dresden, Germany).

Cell Culture and Transformation

Mouse MEL cells carrying a counter-selectable marker, HYTK, flanked by inverted lox-P sites in the predefined chromosomal sites were grown in DMEM (Invitrogen 11965) with 10% FBS (Hyclone) at 37° C. in 7.5% $CO_2$. The cells were maintained in 700 µg/ml Hygromycin B (Invitrogen). Electroporation was performed as follows: the pYB reporter gene construct including the eGFP transgene (100 µg) and the iCre expression plasmid (50 µg) in approximately 100 µl TE were added to approximately $5 \times 10^6$ cells in 700 µl of PBS in a 0.4 cm gap cuvette and then co-electroporated at 0.3 kV, 960 µF into MEL cells. Selection for loss of the HYTK gene with 10 µM Gancyclovir was begun approximately 48 hours post electroporation. Gancyclovir resistant clones were expanded and tested for targeted recombination by PCR (Table 6). Clones were the subject of FACS analysis and southern blotting for further analysis of genomic organization as appropriate.

TABLE 6

Primers used for cloning of the RL5 locus and determination of orientation of the insert

| Name | Primer sequence |
|---|---|
| DW-ACP 1* | 5' ACP-aggtc 3' |
| DW-ACP 2* | 5' ACP-tggtc 3' |
| DW-ACP 3* | 5' ACP-gggtc 3' |
| DW-ACP 4* | 5' ACP-cggtc 3' |
| DW-ACPN* | 5' ACPN-ggtc 3' |
| Uni-primer* | 5' tcacagaagatgccaagcga 3' (SEQ ID NO: 42) |
| 5'HyTk TSP 1 | 5' gggtaccgagctcgaattcact 3' (SEQ ID NO: 43) |
| 5'HyTk TSP 2 | 5' gccgtcgttttacaacgtcgtgac 3' (SEQ ID NO: 44) |
| 5'HyTk TSP3 | 5' gggaaaaccctggcgttacccaact 3' (SEQ ID NO: 45) |
| 3'HyTk TSP 1 | 5' gttatccgctcacaattccaca 3' (SEQ ID NO: 46) |
| 3'HyTk TSP 2 | 5' ccacacaacatacgagccggaagc 3' (SEQ ID NO: 47) |
| 3'HyTk TSP 3 | 5' cctggggtgcctaatgagtgagc 3' (SEQ ID NO: 48) |
| 3'HyTk TSP 4 | 5' cgttttccataggctccgcc 3' (SEQ ID NO: 49) |
| 3'HyTk TSP 5 | 5' cggtaagacacgacttatcgcca 3' (SEQ ID NO: 50) |
| 3'HyTk TSP 6 | 5' cacagcagtaaaaccctaacta 3' (SEQ ID NO: 51) |
| RL5 Tel 1 | 5' tggaggccctctccactca 3' (SEQ ID NO: 52) |

TABLE 6-continued

Primers used for cloning of the RL5 locus and determination of orientation of the insert

| Name | Primer sequence |
|---|---|
| RL5 Cen 1 | 5' gtgaagaccaggcatggaggct 3' (SEQ ID NO: 53) |
| RL5 Cen 2 | 5' aagctctccccactggtttgctc 3' (SEQ ID NO: 54) |
| RL5 Cen 3 | 5' catgagcctgtggggagatgtcc 3' (SEQ ID NO: 55) |
| RL5 Cen 4 | 5' gtctcactctgtagtgcagaaca 3' (SEQ ID NO: 56) |
| RL5 Cen 5 | 5' catggtcatactttccctagct 3' (SEQ ID NO: 57) |
| RLS Cen 6 | 5' cacagcagtaaaaccctaacta 3' (SEQ ID NO: 58) |
| seq 1 | 5' aacggagtaacctcggtgtg 3' (SEQ ID NO: 59) |
| seq 2 | 5' agctgctgagtgggagagag 3' (SEQ ID NO: 60) |
| seq 3 | 5' gctgtacaagtaaagcggcc 3' (SEQ ID NO: 61) |
| seq 4 | 5' caagacgtttcccgttgaat 3' (SEQ ID NO: 62) |
| D1 | 5' aacgccagggttttcccagtcacg 3' (SEQ ID NO: 63) |
| D2 | 5' gggcagtgagcgcaacgcaatta 3' (SEQ ID NO: 64) |
| D3 | 5' ggcggtaatgttggacatgagcgaat 3' (SEQ ID NO: 65) |
| D4 | 5' ctgaagcttcccgggggtaccgaat 3' (SEQ ID NO: 66) |
| D5 | 5' cggccgctgacgtcgaagttcctat 3' (SEQ ID NO: 67) |
| D6 | 5' tcactctcggcatggacgagctgta 3' (SEQ ID NO: 68) |

*These primers were provided by the manufacturer (Seegene).

FACS Analysis

FACS analysis of eGFP expression was performed on a FACSCalibur instrument (BD Biosciences) under the control of CellQuest™ acquisition software (BD Bioscience) acquisition software and analyzed statistically with FlowJo software (Feng et al., *Mol. Cell. Biol.* 21:298-309, 2001). A minimum of $4 \times 10^4$ cells was analyzed for each cell line at 487 nm.

Excision of Repeats Along with the YAC/BAC Cassette.

Excision was performed by transfection of 50 µg pCAGGS-FLPe vector (Gene Bridges) with approximately $5 \times 10^6$ cells of each clone. Forty-eight hours after transfection, cells were selected with 500 µg/ml puromycin for 7 days. After 7 days, cells were distributed into 96-well plates in 10 µM Gancyclovir. Selection of the excised clone was confirmed by measuring the eGFP gene expression level and by PCR (Table 6).

Chromatin Immunoprecipitation (ChIP) Assay.

ChIP assay was carried out using ChIP assay kit (Upstate) according to the manufacturer's instructions. Briefly, $6 \times 10^6$ cells were fixed with 1% formaldehyde for 10 minutes at 37° C. After serial washings, cells were resuspended to $1 \times 10^6$ cells per 200 µl of SDS Lysis Buffer and sonicated for 30 seconds with subsequent 30 second interval for 16 minutes at 4° C. using Bioruptor (Cosmo Bio, USA). Immunoprecipitated DNA with lysine 4-di- and tri-methylated histone H3 (H3K4me2 and H3K4me3), lysine 9-tri-methylated histone H3 (H3K9me3) (Upstate, N.Y.) and mixture of nine anti-CTCF mouse monoclonal antibodies (Pugacheva et al., *Hum. Mol. Genet.* 14: 953-965, 2005) was quantitated by real-time PCR using the iCycler IQ (Bio-Rad). The sequences of primers are listed in Table 7.

TABLE 7

Primers used for chromatin immunoprecipitation (ChIP) assay

| Name | Forward primer | Reverse primer |
| --- | --- | --- |
| C mBG 4 | 5' atggcctgaatcacttggac 3' (SEQ ID NO: 69) | 5' ttctcaggatccacatgcag 3' (SEQ ID NO: 80) |
| C mAmylase 2 | 5' ttctgctgctttccctcatt 3' (SEQ ID NO: 70) | 5' cgaacaggtggacaatagca 3' (SEQ ID NO: 81) |
| C RL5 Right 1 | 5' cagggagccaacagtctttc 3' (SEQ ID NO: 71) | 5' ccacacaaggagtccaaggt 3' (SEQ ID NO: 82) |
| C RL5 Right 2 | 5' tcgtgacgtctatggttactc 3' (SEQ ID NO: 72) | 5' ctctgctgaagccagttacctt 3' (SEQ ID NO: 83) |
| C YAC cassette 2 | 5' tcaccaatgcactcaacgat 3' (SEQ ID NO: 73) | 5' cagtagcagaacaggccaca 3' (SEQ ID NO: 84) |
| C BAC cassette 1 | 5' ctggggaagcatggttctaa 3' (SEQ ID NO: 74) | 5' caccagttgaagagcgttga 3' (SEQ ID NO: 85) |
| C eGFP 6 | 5' agaacggcatcaaggtgaac 3' (SEQ ID NO: 75) | 5' tgctcaggtagtggttgtcg 3' (SEQ ID NO: 86) |
| C RL5 Lefe (tel) | 5' ttatggcatggcgatttgta 3' (SEQ ID NO: 76) | 5' tgaccttcccagtcttgctt 3' (SEQ ID NO: 87) |
| Gamma 8 | 5' gtgctgtaatgcttcaggttttg 3' (SEQ ID NO: 77) | 5' caacctattccaaagcctggg 3' (SEQ ID NO: 88) |
| Gamma X | 5' ctgtggggacagacacacac 3' (SEQ ID NO: 78) | 5' tttcaggggtacgttgaagc 3' (SEQ ID NO: 89) |
| Gamma Y | 5' acctgacgtgctgtctcctt 3' (SEQ ID NO: 79) | 5' gaggcctacttgcgactttg 3' (SEQ ID NO: 90) |
| Mouse c-myc | 5' aagtaagtgtgccctctactgg 3' (SEQ ID NO: 37) | 5' aaggaagcatcttcccagaa 3' (SEQ ID NO: 154) |
| Human c-myc | 5' agaataacaaggaggtggctggaaacttg 3' (SEQ ID NO: 38) | 5' ttgcaaattactcctgcctccaggcctt 3' SEQ ID NO: 155) |
| Gamma FISH 8 | 5' gaattctgggagtgacccaa 3' (SEQ ID NO: 39) | 5' gaattccttgtgggctcgc 3' (SEQ ID NO: 156) |
| Gamma FISH 12 | 5' tcactccctgggcacgaacc 3' (SEQ ID NO: 40) | 5' gcagaggtcaccccaacga 3' (SEQ ID NO: 157) |
| Gamma FISH 21 | 5' gcccacgtaattcaattcact 3' (SEQ ID NO: 41) | 5' aaggagtgtgaccaaaactca 3' (SEQ ID NO: 158) |
| Gamma X Fiber | 5' ttcaacgtaccctgaaagcctgg 3' (SEQ ID NO: 153) | 5' ctattttgtcccaagcctgcc 3' (SEQ ID NO: 159) |

Luciferase Reporter Assays

The reporter-constructs to measure promoter and enhancer activity of gamma-satellite DNA were generated by cloning of a 1.9 kb gamma-satellite DNA fragment from chromosome 8 into pGL2. The constructs were transfected with Fugene 6 reagent according to the manufacturer's protocol (Roche, Indianapolis, Ind., USA) into the mouse MEL cells, NIH3T3 cells, or human embryonic kidney 293 cells grown to 30-50% confluence in a 12-well plate (Corning, N.Y., USA) using 1 μg of pGL2 reporter plasmids and 0.1 μg of the internal transfection efficiency control plasmid expressing *Renilla* luciferase according to the protocol (Promega, Madison, Wis., USA). Two days after the transfection cells were lysed and luciferase activity was measured in a luminometer using a Dual-Luciferase Reporter Assay System (Promega, Madison, Wis., USA) and normalized to *Renilla* expression. Control transfections were performed using the pGL2-basic parent plasmid with no promoter insert and the pGL2-control plasmid containing the SV40 promoter and enhance region. Experiments were repeated at least three times.

Enhancer Blocking Assay

Enhancer blocking assays were performed as previously described (Chung et al, *Cell* 74: 505-514, 1997). 2 μg of AatII linearized constructs were electroporated into K562 cells. After 1 day, cells were plated in soft tissue culture agar (Sigma) with 750 μg/ml geneticine (Invitrogen, Carlsbad, Calif., USA). Colonies were counted after 2-3 weeks of selection.

Nuclear Protein Extraction, Electrophoretic Mobility Shift Assays (EMSA), and Methylation Interference The luciferase control as well as 11 ZF DNA binding domain of CTCF protein were synthesized from the Luciferase T7 control DNA and pET16b-11ZF construct, respectively (Filippova et al., *Mol Cell Biol.* 16: 2802-2813; Awad et al., *J. Biol. Chem.*, 274:27092-27098, 1999), with the TnT reticulocyte lysate coupled in vitro transcription-translation system (Promega, Madison, Wis. USA). Overlapping approximately 250-bp fragments covering a 1.9 kb gamma-satellite 8 DNA unit or a 2.8 kb alphoid DNA unit from human chromosome 21 were $^{32}$P-labeled, gel purified, and used as DNA probes for gel mobility shift assays with equal amounts of in vitro translated luciferase and CTCF proteins as described (Filippova et al., 1996; Awad et al., 1999; ibid).

Gamma-satellite monomers from human chromosome X and Y were PCR amplified from genomic DNA, cloned into TA vector and sequenced before their analysis by electrophoretic mobility gel-shift assay (EMSA). Corresponding primer sequences are presented in Table 8. Binding reactions were carried out in buffer containing standard PBS with 5 μM $MgCl_2$, 0.1 μM $ZnSO4$, 1 μM DTT, 0.1% NP40, and 10% glycerol in the presence of poly(deoxyinosinic-deoxy-CMP) and salmon sperm DNA. Reaction mixtures of 20 μL final volume were incubated for 30 minutes at room temperature and then analyzed on 5% nondenaturing gel using polyacrylamide gel electrophoresis (PAGE) in 0.5×TBE buffer. For EMSA with in vitro methylated DNA probes, treatment with the SssI-methylase was done as previously described for CTCF-binding fragments DMD4 and DMD7 of the H19 ICR (Kanduri et al., *Curr. Biol.*, 10:853-856, 2000). The extent of methylation was verified by digestion overnight with Sau96I restriction endonuclease. Methylation interference analysis was carried out as described previously (Filippova et al., 1996; ibid).

TABLE 8

Primers used for amplification of gamma and alphoid satellite for electrophoretic mobility shift assay (EMSA)

| Name | Forward primer | | Reverse primer | |
|---|---|---|---|---|
| Gamma 8 gel 1 | 5' ctgggagtgacccaaagagg 3' | (SEQ ID NO: 91) | 5' gaatgggatgagaacgcaggg 3' | (SEQ ID NO: 113) |
| Gamma 8 gel 2 | 5' ctatgagcttctgtgatggg 3' | (SEQ ID NO: 92) | 5' ggggtcttctgagatagaag 3' | (SEQ ID NO: 114) |
| Gamma 8 gel 3 | 5' gggaagagtccagacggcag 3' | (SEQ ID NO: 93) | 5' tcccagcattccctgcggtc 3' | (SEQ ID NO: 115) |
| Gamma 8 gel 4 | 5' atggccaggccgcagggac 3' | (SEQ ID NO: 94) | 5' cttctcctctatgcttgcc 3' | (SEQ ID NO: 116) |
| Gamma 8 gel 5 | 5' ggctggatggcatgggccg 3' | (SEQ ID NO: 95) | 5' gcctcaacgtctccctgag 3' | (SEQ ID NO: 117) |
| Gamma 8 gel 6 | 5' caaaaacagtgccgcagt 3' | (SEQ ID NO: 96) | 5' ccagcccacgccaccctgcgg 3' | (SEQ ID NO: 118) |
| Gamma 8 gel 7 | 5' ccccaggctttggaacagcg 3' | (SEQ ID NO: 97) | 5' acagccctgggtgcttctggg 3' | (SEQ ID NO: 119) |
| Gamma 8 gel 8 | 5' ggcaggcagagatgagaag 3' | (SEQ ID NO: 98) | 5' ctcccagcattccatgtgg 3' | (SEQ ID NO: 120) |
| Gamma 8 gel 9 | 5' gggcagcagggactcacgg 3' | (SEQ ID NO: 99) | 5' ccccttttccgcttgtggg 3' | (SEQ ID NO: 121) |
| Gamma 8 gel 10 | 5' gtgctgtaatgcttcaggttttg 3' | (SEQ ID NO: 100) | 5' caacctattccaaagcctggg 3' | (SEQ ID NO: 122) |
| Gamma 8 gel 11 | 5' atgctgcgaccctcccaagg 3' | (SEQ ID NO: 101) | 5' gaattccttgtggggctcg 3' | (SEQ ID NO: 123) |

TABLE 8-continued

Primers used for amplification of gamma and alphoid satellite
for electrophoretic mobility shift assay (EMSA)

| Name | Forward primer | | Reverse primer | |
|---|---|---|---|---|
| alphoid gel 1 | 5' aattcaaataaaaggtagac 3' | (SEQ ID NO: 102) | 5' aaaggttccactctgttagc 3' | (SEQ ID NO: 124) |
| alphoid gel 2 | 5' aaaagtaaatatcttccata 3' | (SEQ ID NO: 103) | 5' tctgttagttgaggacacac 3' | (SEQ ID NO: 125) |
| alphoid gel 3 | 5' tatcgttggaaaagggaata 3' | (SEQ ID NO: 104) | 5' gaatgcagatatcaccaagt 3' | (SEQ ID NO: 126) |
| alphoid gel 4 | 5' aaacgggaatatcatcatct 3' | (SEQ ID NO: 105) | 5' cttttagttgagtacacaca 3' | (SEQ ID NO: 127) |
| alphoid gel 5 | 5' tgcctttgttgaaaaggaaa 3' | (SEQ ID NO: 106) | 5' ttgaatggaaatatccgaaa 3' | (SEQ ID NO: 128) |
| alphoid gel 6 | 5' gattgcntgaggatttcgt 3' | (SEQ ID NO: 107) | 5' tatcaccaacaagtttctga 3' | (SEQ ID NO: 129) |
| alphoid gel 7 | 5' cgcctacggtgaaaaggaa 3' | (SEQ ID NO: 108) | 5' tgaatgcagtcatcagaaag 3' | (SEQ ID NO: 130) |
| alphoid gel 8 | 5' ggatagcttggaggatttcg 3' | (SEQ ID NO: 109) | 5' tcacaaacttgtttctcaga 3' | (SEQ ID NO: 131) |
| alphoid gel 9 | 5' ggacatttggagcgcntga 3' | (SEQ ID NO: 110) | 5' tctgagagggcttctgtcta 3' | (SEQ ID NO: 132) |
| Gamma X gel 1* | 5' ctgtggggacagacacacac 3' | (SEQ ID NO: 111) | 5' tttcaggggtacgttgaagc 3' | (SEQ ID NO: 133) |
| Gamma Y gel 1* | 5' acctgacgtgctgtctcctt 3' | (SEQ ID NO: 112) | 5' gaggcctacttgcgactttg 3' | (SEQ ID NO: 134) |
| Major gel 1 | 5' tatggcgaggaaaactg 3' | (SEQ ID NO: 160) | 5' tttcacgtcctaaagtgtg 3' | (SEQ ID NO: 162) |
| Major gel 2 | 5' cagtggacatttctaaattt 3' | (SEQ ID NO: 161) | 5' ggaatatggtgagaaaactg 3' | (SEQ ID NO: 163) |

*The primers for PCR amplification of human gamma X and Y satellite DNA fragments were developed from genomic sequences GI: 1223742 and GI: 7687989.

Immunofluorescence (IF)-FISH

Extended chromatin fibers were generated as described in (Sullivan and Karpen, *Nat. Struct. Mol. Biol.,* 11: 1076-1083, 2004; Lam et al., *Proc. Natl. Acad. Sci. USA.,* 103: 4186-4191, 2006). Chromosome 8-specific gamma-satellite DNA was identified by using a 24 kb amplified array. Probes were labeled with biotin-16-dUTP (Roche), digoxygenin-11-dUTP (Roche), or AlexaFluor dUTPs (Molecular Probes). Antibodies were cross-linked to proteins/DNA using 8% formalin prior to FISH, which was performed according to published protocols (Blower et al, *Dev Cell* 3:1-1, 2002; Lam et al, 2006).

ChIP-PCR for Histone Modification Enrichment at Gamma Satellite DNA in Human Dermal Fibroblasts Native chromatin containing oligonucleosomes was isolated from cultured cells and prepared by micrococcal nuclease digestion as described (Lam et al, 2006). Immunoprecipitated DNA (IP DNA) was used for semi-quantitative PCR and/or quantitative PCR (QPCR). Primers that amplified gamma-satellite specific for human X chromosome were published previously (Spence et al, *EMBO J,* 21:5269-5280, 2002).

Targeting Expression Cassettes Containing Repetitive Centromeric and Pericentromeric DNA Elements into the Ectopic Sites of MEL Mouse Cells In order to develop a system that analyzes the effect of mammalian centromeric DNA repeats on expression of adjacent transgenes, a known phenomenon of epigenetic silencing of integrated transgenes by vector backbone sequences was exploited (Chen et al., *Gene Ther.,* 11:856-864, 2004; Suzuki et al., *J. Virol.,* 80: 3293-3300, 2006). In this system, different repetitive DNAs were integrated into the chromosome along with a transgene, the expression of which could be easily monitored.

Figure 7A:
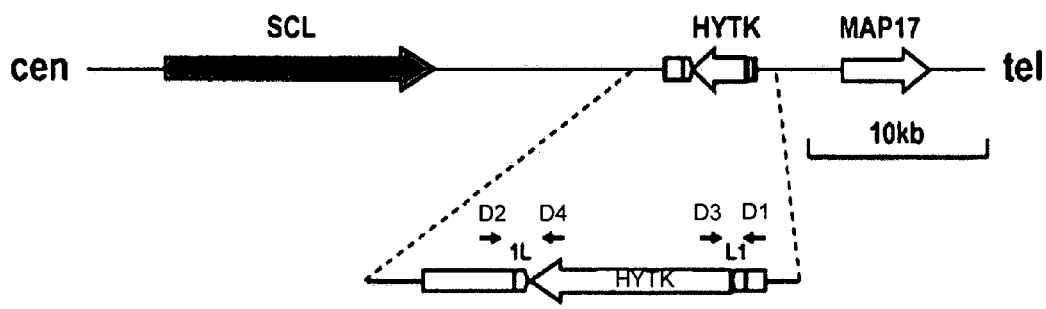
FIG. 7A is a schematic drawing of the cassette containing the CMV-HYTK selectable marker (grey arrow), which was previously integrated into the mouse chromosome 4 (GenBank Accession No. NT_039264.4). In addition, the cassette contains approximately 1 kb of the L1-HYTK-1L vector DNA fragment (pBR replication origin) at the 3' of the HYTK gene region (centromere direction) and approximately 100 bp at the 5' end of the HYTK gene region (telomere direction) (white boxes). Mouse chromosomal flanking DNA was isolated using DNA Walking SpeedUp Premix kit (Seegene) according to manufacturer's instructions. To determine the DNA flanking sequences (upstream and downstream of the HYTK gene), nested plasmid specific primers and universal primers were used in PCR reaction that targeted unknown mouse sequences (Table 6). The correct locus was confirmed by PCR with specific chromosome 4 and L1-HYTK-1L plasmid primers (Table 6). The HYTK gene in RL5 cells maps to between positions 15176155-15176171 of the mouse chromosome 4 in the cytogenetic band qD1 (NT_039264.4). The L1-HYTK-1L integrated fragment is located between the SCL gene (approximately 12.7 kb) and the Map17 gene (approximately 4.5 kb). The insertion resulted in very little alteration in the structure of DNA at the site of integration, i.e. deletion of 15 bp endogenous DNA and insertion of 15 bp of unknown sequence to centromere direction and 6 bp to telomere direction.
Figure 7B:
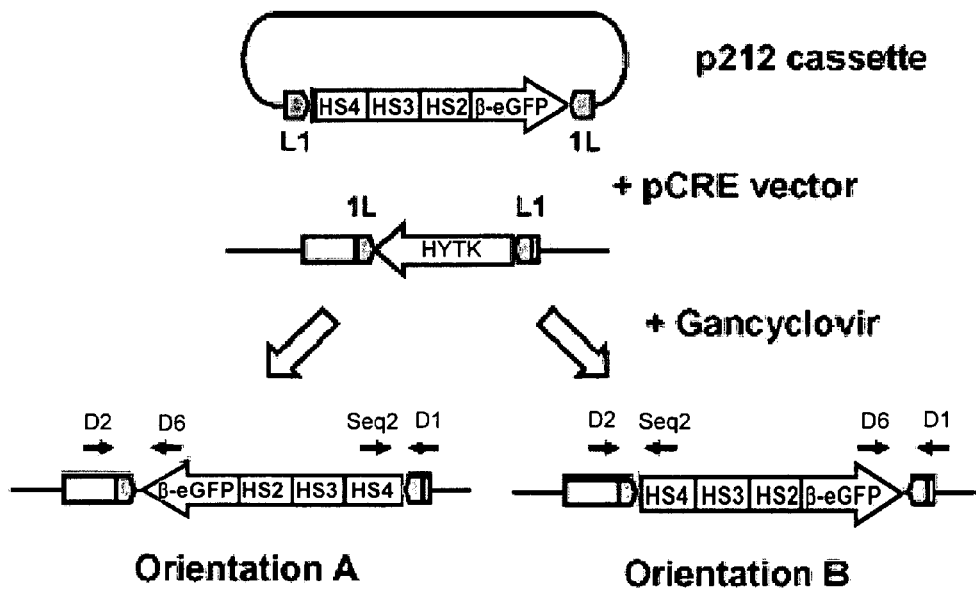
FIG. 7B is a schematic drawing of the Cre recombinase-mediated cassette exchange (RMCE) technique, which was used for the precise replacement of the L1-HYTK-1L cassette by the p212 cassette (the cassette LCR 234-β-eGFP only) at the RL5 locus. After replacement, the p212 vector produced two types of orientation: A and B.
Figure 7C:
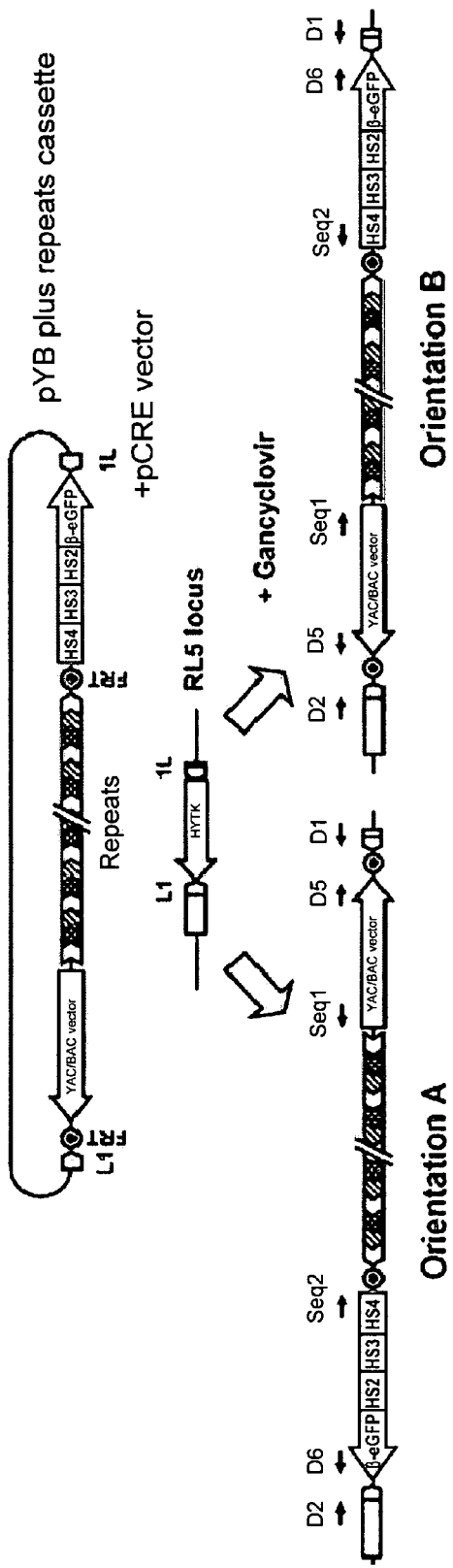
FIG. 7C is a schematic drawing of the cassette exchange of pYB plus repeats at RL5 locus. The integrity of the insert was confirmed using the appropriate pairs of primers D1, D2, D3, D4, D5, D6, Seq1 and Seq2 (Table 6).

Because the chromosomal and cellular environments affect gene silencing, it was necessary to create isogenic cell lines that varied only in the DNA sequence, not the location, of the repetitive DNA. For this purpose, the RL5 mouse erythroleukemia (MEL) cell lines (carrying a counter-selectable marker, HYTK, flanked by inverted lox-P sites in the predefined chromosomal sites) were used. The HYTK-containing cassette is on chromosome 4 (Feng et al., *Mol. Cell. Biol.,* 21:298-309, 2001). The cassette was physically mapped to the SCL/MAP17 locus (FIG. 7). The presence of the lox-P-containing cassette allows integration of transgenes into the predefined chromosomal sites at high efficiency using a recombinase-mediated cassette exchange (RMCE) system after induction of the Cre recombinase (Schubeler et al., *Mol Cell Biol.* 20:9103-9112, 2000; Feng et al., *Mol. Cell. Biol.,* 21:298-309, 2001; Eszterhas et al., *Mol Cell Biol.,* 22:469-479, 2002).

Figure 1B:
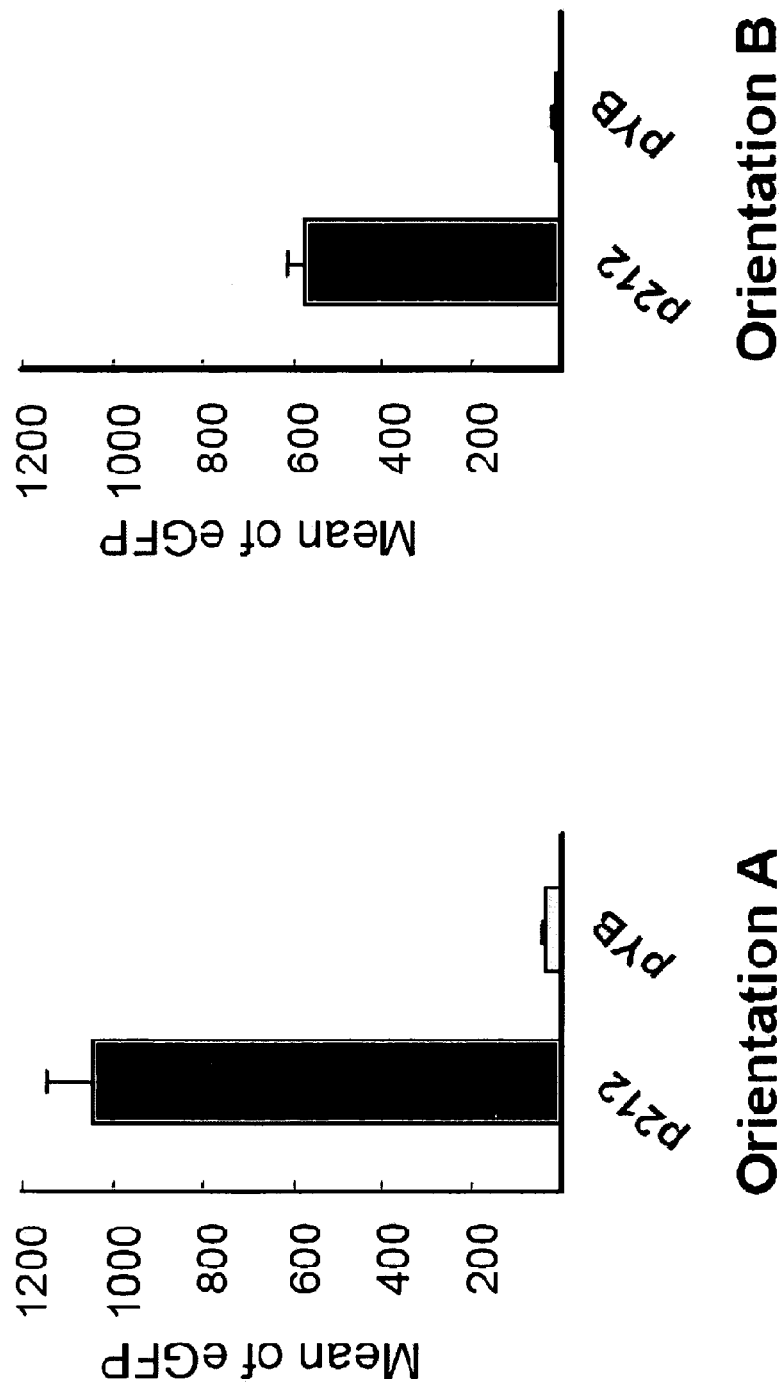
FIG. 1B is a series of graphs demonstrating the relative expression level of eGFP when p212 was in orientation A or orientation B. The pYB cassette showed the lowest eGFP expression level in both orientations. Each bar represents the data from 3-6 independent clones.

As originally developed, the RMCE system uses the p212 basic targeting cassette which carries the enhanced green fluorescent protein (eGFP) reporter gene under control of the human β-globin promoter and the human β-globin locus control region (Feng et al. *Mol. Cell. Biol.*, 21:298-309, 2001). When the eGFP transgene (p212 cassette) exchanges into the target locus in RL5 cells, the transgene is expressed at high level, with higher expression in orientation A than in orientation B (FIGS. 1A and 1B). Because the transgene contains a locus control region at the 5' end (that functions as a weak insulator), the level of the transgene expression may be different in orientation A versus orientation B once the transgenes are integrated into the ectopic site. This may be cause by the fact that the transgene is flanked with two different chromosomal regions with different potentials for heterochromatization. Alternatively, it may be caused by the fact that the transgene is flanked with two chromosomal regions with different transcriptional potentials. Because the transgene contains a transcribed unit, transcriptional interference may affect the level of transgene expression and heterochromatization of the entire region. For this cell line, the level of transgene expression was stable for at least six months without selection. Thus, the RL5 locus adopts a stable open chromatin structure.

Figure 8D:
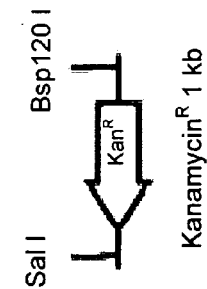
FIG. 8D is a schematic drawing of 1 kb SalI/Bsp120I fragment containing the kanamycin gene ($Kan^R$), which was inserted into the XhoI/NotI site of the vector from FIG. 8C.
Figure 8E:
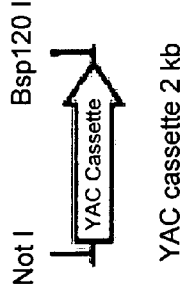
FIG. 8E is a schematic drawing of a 2 kb NotI/Bsp120I fragment containing a YAC cassette (ARS, HIS3 and CEN6) which was inserted into a NotI site downstream of the BAC cassette sequence.
Figure 8F:
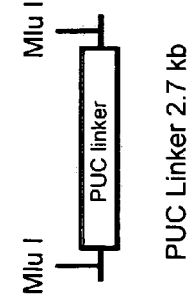
FIG. 8F is a schematic drawing of a 2.7 kb PUC linker from pBACe3.6 vector was inserted into the MluI site of the vector from FIG. 8E to confer a high-copy number to the plasmid. The appropriate primers used for pYB construction are described in Table 4. Large synthetic repeats of mouse major satellite, human gamma 8 satellites were generated by rolling-circle amplification (RCA) and recombinational cloning in yeast (Tables 2, 3 and 5) and cloned into pYB vector. pYB/PUC/cHS4 vector was constructed as follows. The chicken beta-globin locus LCR HS4 site insulator was cloned as two tandem copies of the 250 bp core into a FseI site of pYB/PUC vector between the alphoid hook and the start of the LCR region. A modified Cre expression plasmid was constructed using pBlue iCre (kindly provided by Dr. R. Sprengel), a mammalian codon optimized Cre variant. A NcoI/NheI iCre-containing PCR product was inserted into NcoI/NheI sites of pCpGvitro-hygro-LacZ vo3 vector (Invivogen) replacing LacZ. The pCpG-iCre expression plasmid with no CpG sites in the promoter and vector sequences and with MAR elements flanking the iCre gene generally gives an improved efficiency in recovering of the targeted recombinants in the mouse MEL RL5 cells.

For the analysis of centromeric repeats, a new targeting cassette, pYB, was constructed (FIG. 1A, FIG. 7, FIG. 8). Similar to the basic targeting cassette p212 (Feng et al., *Mol. Cell. Biol.*, 21:298-309, 2001), pYB carries the enhanced green fluorescent (eGFP) gene regulated by the human β-globin promoter and the human β-globin locus control region, LCR(HS2,3,4). When pYB undergoes Cre-mediated exchange into the target locus in RL5, the eGFP reporter gene and the flanking YAC/BAC vector sequence are co-inserted into the mouse chromosome that, as expected, results in reporter gene down-regulation due to epigenetic silencing of the transgene by vector backbone sequences (Chen et al., *Gene Ther.*, 11:856-864, 2004; Suzuki et al., *J. Virol.*, 80: 3293-3300, 2006). Indeed, when the pYB-based eGFP transgene exchanges into the target locus, no transgene expression was detected (FIG. 1B). Because the YAC/BAC vector sequence in pYB is also flanked by FRT sites, it can be excised from the expression cassette by FLP recombinase (FIG. 1C). FLP recombinase-mediated excision of the YAC/BAC vector sequence results in reactivation of transgene expression (FIG. 1D), proving that vector sequence is the cause of transgene silencing. This system was adapted to study the effect of mammalian centromeric repetitive DNA elements on expression of adjacent transgenes in mouse chromosomes in cultured cells.

Figure 2A:
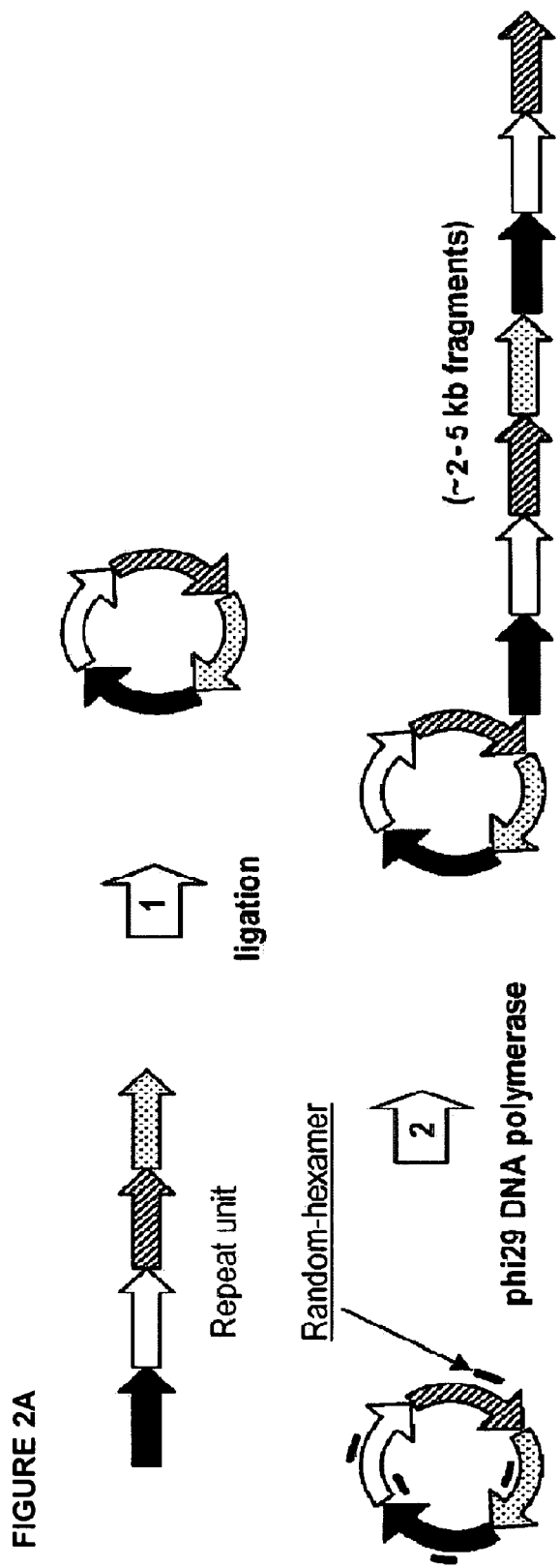
FIG. 2A is a representation of the amplification of different repeat units by Rolling Circle Amplification (RCA). Such amplification generates RCA products up to 2-10 kb in size.
Figure 2B:
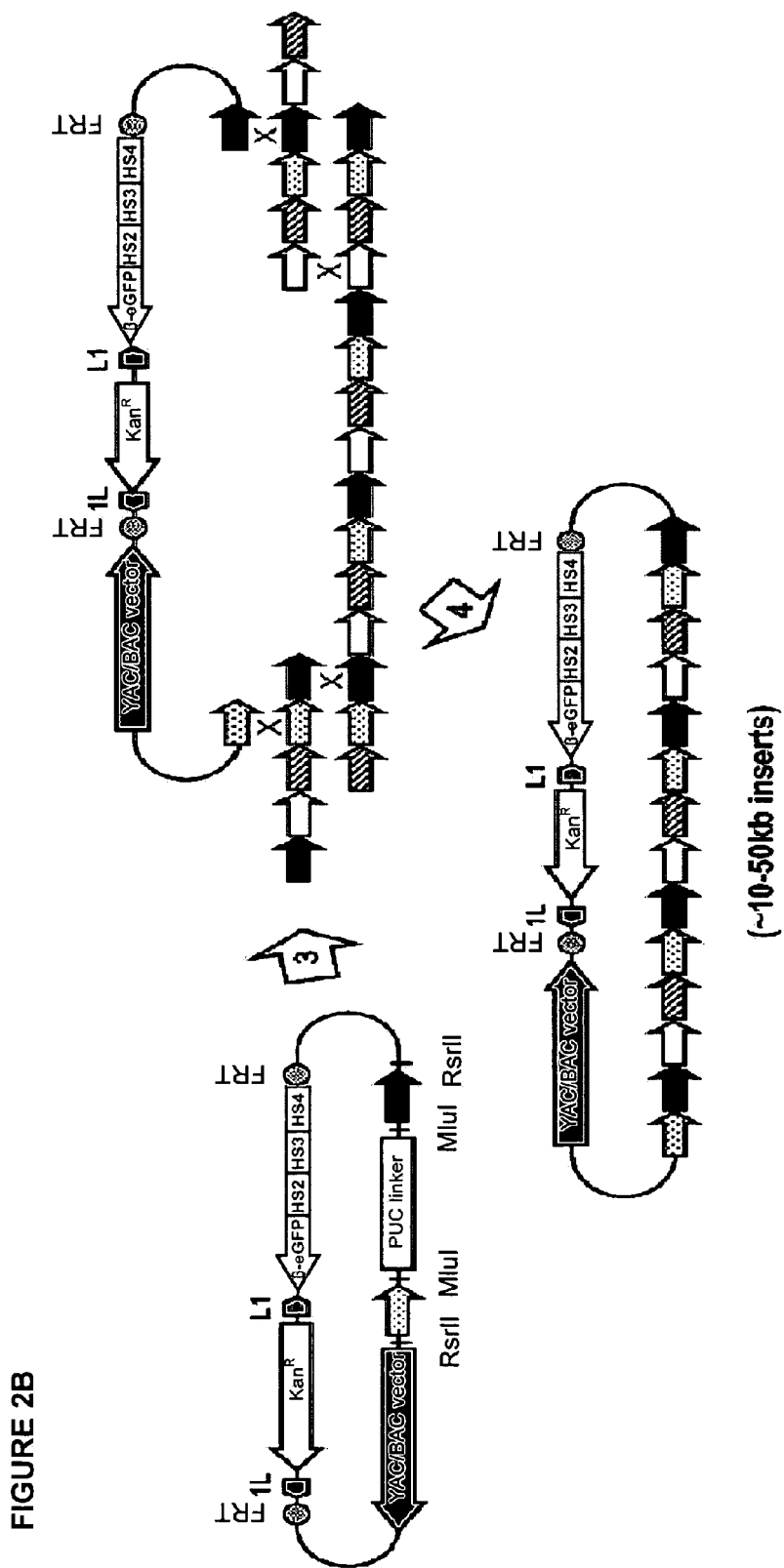
FIG. 2B is a schematic representation of RCA products assembled into long arrays in pYB using in vivo recombination in yeast. Repeat-specific hooks in pYB were released by MluI digestion removing the pUC linker. RCA-amplified repeats and linearized vector were co-transformed into VL6-48 yeast cells. End-to-end homologous recombination of RCA products followed by interaction of the recombined fragments with the vector, results in the rescue of large repeat arrays as circular YACs in yeast.

Different Centromeric DNA Arrays Targeted into the Same Ectopic Chromosomal Site Affect Transgene Expression Differently To analyze the effect of repetitive DNA on expression of adjacent genes, large synthetic centromeric and pericentromeric DNA arrays with a defined structure were generated as described by Ebersole et al. (*Nuc. Acids Res.*, 33, e130, 2005; PCT Application No. PCT/US2006/013362). Briefly, smaller arrays were generated by rolling circle amplification (RCA) and then assembled into longer arrays (up to 35 kb) by homologous recombination during transformation into yeast cells and cloned into pYB to create the reporter cassettes (FIGS. 2A and 2B).

Arrays containing 11-mer alpha-satellite 21-I DNA derived from the centromeric core of chromosome 21 (Masumoto et al., *Chromosome Res.* 12: 543-556, 2004) were constructed and incorporated into reporter cassettes (human alphoid; 10, 18, or 35 kb) (FIG. 2C). Human gamma-satellite DNA arrays (3, 9, or 24 kb) were generated from tandem repeats of eight 220 bp monomers from chromosome 8 (Lin et al., *Chromosoma*, 102:333-339, 1993). Mouse major satellite DNA arrays (10 or 20 kb) were generated from a trimer of diverged copies of a 234 bp monomer (Vissel and Choo, *Genomics*, 5:407-414, 1989). Lastly, a cassette was generated that contained two copies of the chicken β-globin HS4 insulator (cHS4) core, whose enhancer blocking activity requires binding of the CTCF transcription factor (Yusufzai and Felsenfeld, *Proc. Natl. Acad. Sci. USA* 101: 8620-8624, 2004; Gaszner and Felsenfeld, *Nat. Rev. Genet.* 7:703-713, 2006).

The cassettes were integrated at the reference locus in both orientations, A and B. Three to five independent clones were isolated for each cassette in each orientation. The efficiency of exchange, measured as the percentage of ganciclovir-resistant clones that have been correctly targeted, varied between 50 and 80%, indicating that targeting efficiency is not particularly sensitive to the size of DNA sequence of the cassette in the size range tested. Because no local deletions were observed in or near the integrated cassettes, it was concluded that insertion of repeat arrays into the reference site are relatively stable and are not mutagenic.

For each reporter cassette, the level of transgene expression (defined as the mean green fluorescence of the cell population) and the proportion of expressing cells (from which the rate of silencing can be evaluated) of at least six subclones (at least three for each orientation) were monitored regularly by flow cytometry. Comparison of expression levels of the reporter cassettes revealed up to 62-fold differences in the average GFP fluorescence (FIGS. 3A and 3B). At the same time, the expression levels of different subclones with the identical reporter cassette in the same orientation were remarkably similar. eGFP expression was lowest for cassettes carrying human alphoid DNA, indicating that transgene silencing persists in the presence of human alphoid DNA. For cassettes carrying mouse major satellite DNA, eGFP expression was approximately 6-(orientation A) or 14-fold (orientation B) higher than for the control pYB cassette, indicating a modest anti-silencing effect. A modest stimulation of eGFP expression was also observed for cassettes carrying chicken β-globin HS4 insulator DNA.

In contrast, targeting of gamma-satellite arrays resulted in a significant increase of the level of eGFP expression (up to approximately 18- and 62-fold increases for orientation A and B, respectively) compared to the pYB cassette alone. It is notable that this effect did not depend on the size of the arrays. The same level of expression was detected for the arrays containing 3 kb, 9 kb and 24 kb of gamma-satellite DNAs corresponding to 14, 40, and 109 copies of the 220 bp monomer (FIGS. 3A and 3B). eGFP expression was also analyzed after excision of YAC/BAC vector and repetitive DNA sequences. The results show that excision of the vector and the mouse major, human alphoid, or chicken insulator HS4 DNA arrays stimulated eGFP expression at or nearly to the level of the control cassette p212 (FIGS. 3C and 3D). These results suggest that cassettes carrying human gamma-satellite DNA are not subject to vector DNA-induced silencing of eGFP, while cassettes carrying human alphoid DNA, mouse major satellite or cHS4 insulator sequences are only slightly protected from vector DNA induced transgene silencing.

Figure 9A:
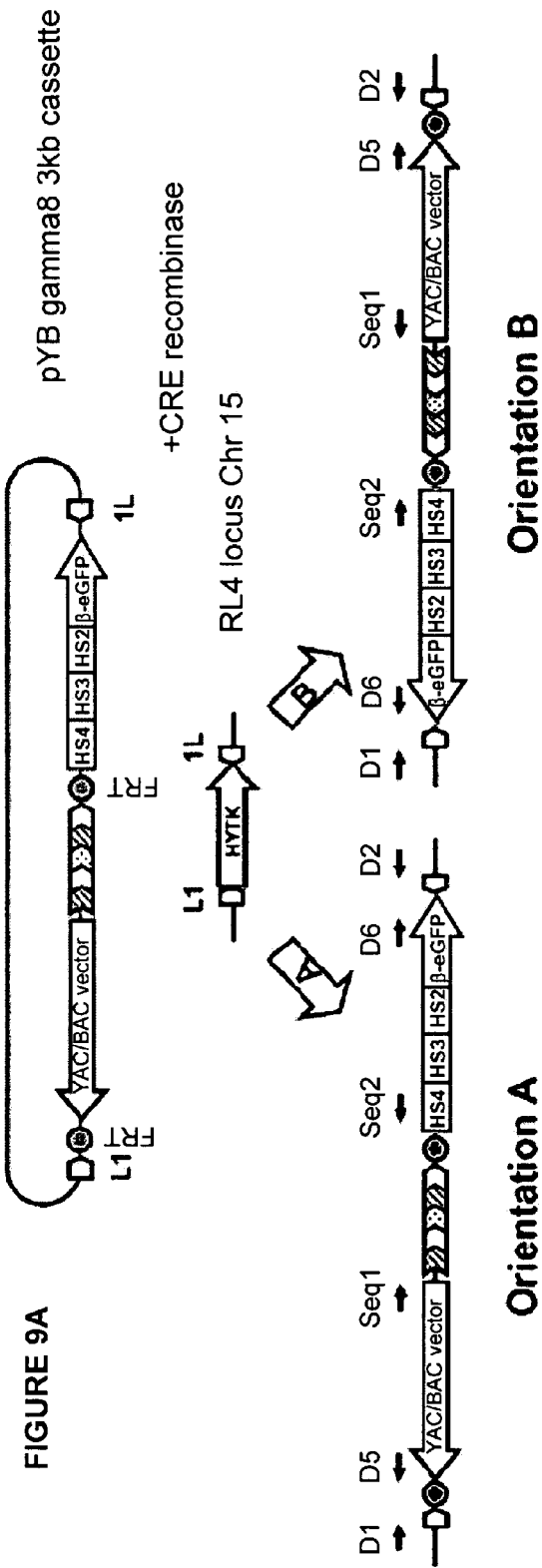
FIG. 9A is a schematic drawing of the RMCE technique which was used for the precise replacement of the L1-HYTK-1 L cassette by 3 kb gamma 8 pYB cassette at the RL4 locus (chromosome 15). After replacement, the vector produced two types of orientation, A and B.
Figure 9B:
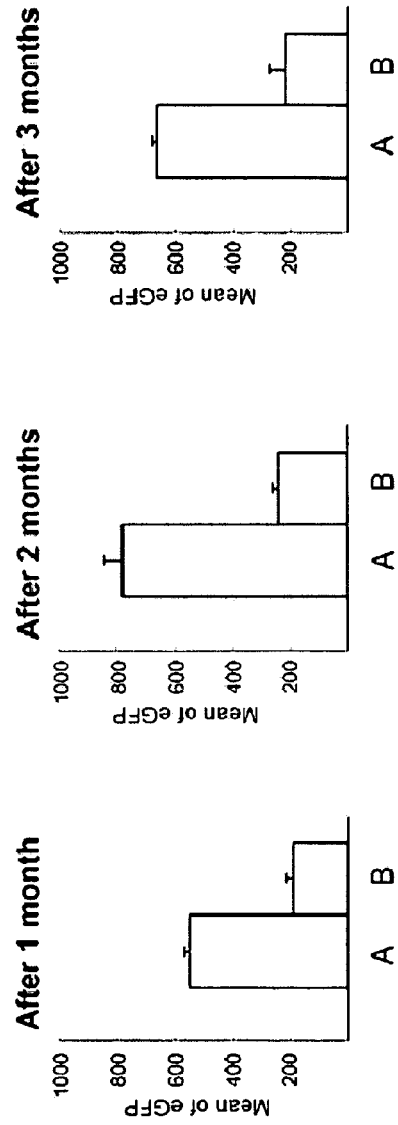
FIG. 9B is a series of graphs representing the level of eGFP in orientation A of the pYB gamma 8 3 kb was higher than in orientation B but the transgene cassette is stably expressed in both orientation during 3 months. Orientations A and B were distinguished by PCR (Table 6).

To determine whether gamma-satellite DNA can prevent gene silencing at other locations, a second set of transgene insertions was created at the random locus RL4, located on mouse chromosome 15. This locus is characterized by fast (about two months) gene silencing in non-permissive transgene orientation A (Feng et al., *Mol Cell Biol.*, 25:3864-3874, 2005). However, stable eGFP expression was observed for more than 3 months when the reporter cassette contained gamma-satellite DNA (FIG. 9). Moreover, stable expression was observed even after 6 months. This effect was observed with different gamma-satellite constructs.

The anti-silencing effect cannot be explained by up-regulation of transgene transcription in the gamma-satellite DNA array constructs. Luciferase reporter assays with a set of pGL2 plasmids did not reveal any significant promoter or enhancer activities of gamma-satellite DNA (FIG. 10). A lack of promoter activity was also suggested by Northern analysis (no transcripts initiated from gamma-satellite DNA were detected in RL5 cells targeted with the 9 kb gamma-satellite repeat cassette). Also, inversion of the gamma-satellite DNA array in the transgene cassette had no effect on transgene expression.

Gamma-Satellite Array Modulates Transgene Chromatin Structure

Figure 4A:
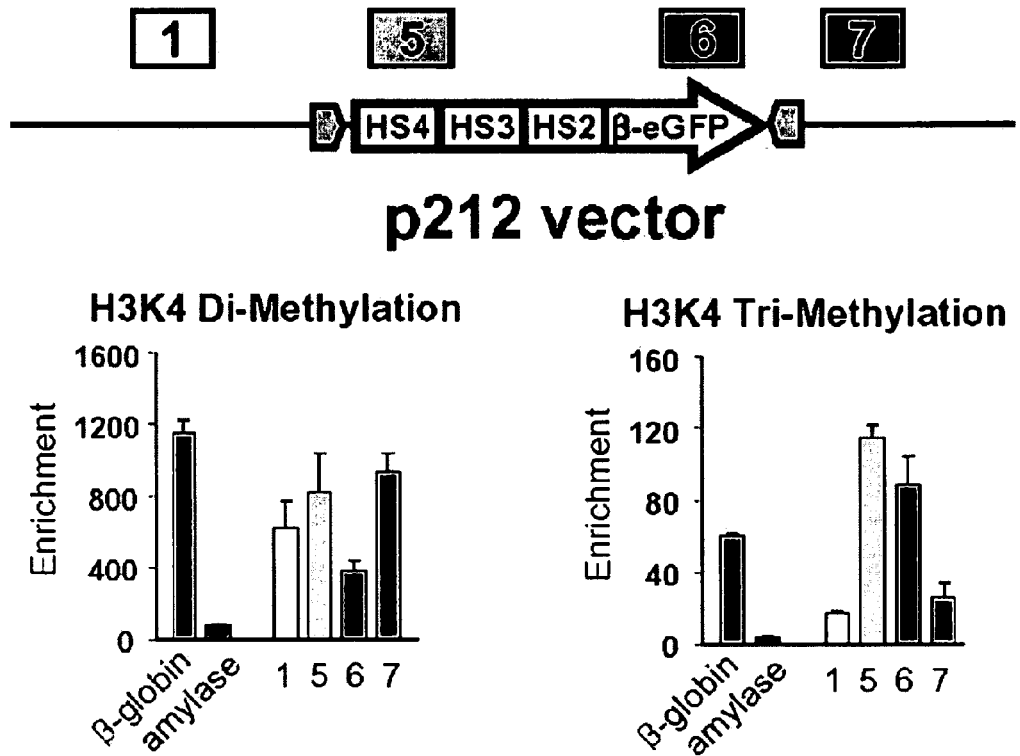
FIG. 4A demonstrates RL5 cells with a p212 cassette. Position of the primers: 1—centromeric side of RL5 locus; 5-5' end of the locus control region; 6—eGFP coding region; 7—telomeric side of RL5 locus.

To assess chromatin structure, a chromatin immunoprecipitation (ChIP) assay was used to measure the enrichment of lysine 5-di and tri-methylated histone H3 (HeK4me2 and H3K4me3) and lysine 9-tri-methylated histone H3 (HeK9me3) in the eGFP transgene. ChIP assays for H3K4me and H3K9me3 were performed for clones carrying cassettes with 9 kb gamma-satellite or 10 kb alphoid DNA arrays in orientation B at the RL5 locus (FIGS. 4A and 4B). Previous studies demonstrated that decondensed and transcriptionally-active chromatin has a higher level of HeK4me2 and H3K4me3 than condensed, transcriptionally-inactive chromatin. In contrast, condensed and transcriptionally inactive chromatin is enriched with HeK9me3 (Peters et al., *Mol. Cell*, 12:1577-1589, 2003).

ChIP assays showed that in both cassettes HeK9me3, a marker for silent chromatin, was associated with the vector DNA sequence (FIGS. 4A and 4B). This is in agreement with the proposed seeding of heterochromatin by the vector DNA. Enrichment of K4meH3 in the eGFP transgene correlated with the presence of gamma satellite DNA but not with the presence of alpha-satellite DNA (FIGS. 4A and 4B). Alphoid DNA was enriched with anti-H3K9me3 but not enriched with H3K4me2 or H3K4me3, suggesting that the inserted alphoid DNA formed heterochromatin. The level of H3K4me2 euchromatic modification was higher with gamma-satellite DNA. At the same time the level of H3K9me3 was significantly lower compared to that of alphoid DNA, suggesting a more open chromatin structure of the gamma-satellite array. The presence of gamma-satellite DNA did not change the predominant histone modifications on the vector sequence, which remained heterochromatic. Notably, we observed a progressive decrease of H3K9met3 from YAC/BAC vector to transgene (FIG. 5C; probes 2, 3, 4, 5) that is in accordance with an active spreading of heterochromatin from the vector sequence towards the transgene with its progressive trapping of heterochromatin within the gamma-satellite array.

Control experiments with RL5 cells containing the p212 basic targeting cassette or pYB targeting cassette were also performed. As predicted from the transgene expression data, the eGFP sequence in the p212 but not in the pYB cassette is enriched with K4meH3 specific for transcriptionally-active chromatin (FIG. 11). These results suggest that gamma-satellite arrays either induce a transcriptionally permissive chromatin conformation in adjacent transgene sequences or prevent spreading of transcriptionally-inactive chromatin from the vector backbone sequence.

Human Gamma-Satellite DNA Monomers Contain CTCF Binding Sites

To further characterize the centromeric repeats and clarify their structural difference resulting in difference in anti-silencing (insulating) activities, the presence of CTCF binding sequences in the repeats was examined. These experiments were inspired by the observed, though modest, anti-silencing activity of the chicken beta-globin HS4 insulator known to have CTCF-binding sites. Also, because strong anti-silencing activity of gamma-satellite DNA with regard to the transgene cassettes in RL5 cells may be due to insulator activity (Bell et al, *Cell* 98:387-396, 1999; Bell and Felsenfeld, *Nature* 405:482-485, 2000), the possibility that gamma-satellite sequences contain recognition sites for the insulator protein CTCF was explored.

CTCF is a highly conserved, ubiquitously expressed 11-zinc finger DNA-binding protein (Lobanenkov et al., *Oncogene*, 5:1743-1753, 1990; Filippova et al., *Mol Cell Biol.*, 16:2802-2813, 1996). Because of multiple zinc fingers DNA-binding domains, the binding specificity and functional roles of CTCF are complex, including enhancing blocking/silencing and promoting interchromosomal associations (Ohlsson et al., *Trends Genet.*, 17:520-527, 2001; Ling et al., *Science*, 312:269-272, 2006).

Electrophoretic mobility shift assays (EMSA) were performed. A set of overlapping fragments corresponding to an 1'-mer of the human gamma 8, were radiolabeled and incubated with the in vitro translated 11 ZF DNA binding domain of the CTCF protein. Recombinant luciferase protein prepared by the same in vitro translation reaction was used as a negative control. EMSA showed a specific interaction between CTCF and eleven gamma-satellite DNA fragments. However, not all fragments bound to CTCF with the same efficiency, indicating that divergence between gamma-satellite monomers may affect affinity of the CTCF-target sites (FIG. 5A). The strongest binding was observed with the fragments 5, 6, 8, 10, and 11, corresponding to gamma-satellite monomers 4, 5, 6, 7, and 8, respectively. The presence of CTCF-binding sites was also checked in the human alpha-satellite DNA array lacking anti-silencing (insulating) activity. None of 11 alpha-satellite monomers analyzed bound the CTCF protein in vitro.

Figure 5B:
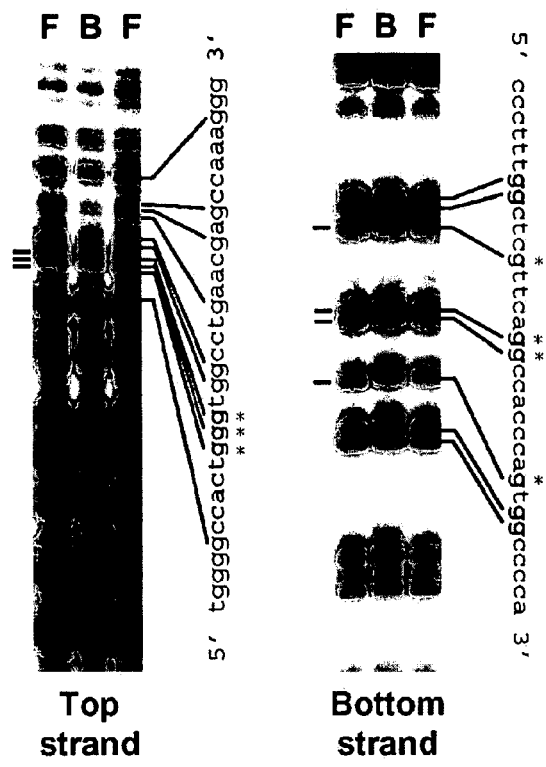
FIG. 5B shows methylation interference of the CTCF binding to the human gamma-satellite 8 DNA. Top and bottom strands of the gamma-satellite DNA fragment #11 are shown. The corresponding DNA sequences are shown on the right. Seven methylated contact guanine residues are marked with asterisks. Lane F, modified guanines of the free DNA probe. Lane B, methylated guanines of DNA molecules bound by CTCF.

To determine the contact guanine residues recognized by CTCF in gamma-satellite DNA, methylation interference assays (a method that identifies guanine residues in the CTCF binding site that make contact with CTCF zinc fingers) were conducted using a $^{32}$P-labeled fragment of the gamma-satellite monomer (fragment #11). A strong interference of guanine methylation with CTCF-DNA binding was found in three and four guanine residues on sense and anti-sense strands, respectively (FIG. 5B). These seven contact guanine bases allowed narrowing-down to a CTCF binding sequence, and nucleotides that were recognized by the CTCF protein in vitro were identified. A predicted core sequence, based on the comparison of eight monomers, is 5' CA/TGGGTGG CNTGGNC 3' (the contact nucleotides are bold and underlined; SEQ ID NO: 1). This consensus is different from all previously reported CTCF binding sequences (FIG. 12; Kim et al., *Cell* 128:1231-1245, 2007; Bell and Felsenfeld, *Nature*, 405:482-485, 2000). CTCF is known to be quite promiscuous in its binding to DNA due to the presence of 11 zinc-fingers, combinations of which result in recognition of very different targets (Ohlsson et al., *Trends Genet* 17:520-527, 2001; Mukhopadhyay et al., *Genome Res.*, 14:1594-15602, 2004). Thus gamma-satellite DNA is a novel target for CTCF.

To confirm in vitro mapping results, four guanine residues within the predicted core sequence were selectively mutated, as indicated in FIG. 12. EMSA showed that all the mutations knocked down CTCF binding (FIG. 5C). To determine if CTCF binding is methylation-dependent, gamma-satellite 8 PCR fragments were methylated with a SssI methyltransferase. EMSA revealed that methylation does not affect the binding of the in vitro-translated CTCF to gamma-satellite DNA fragments. It is worth noting that in most previously reported cases, methylation prevents CTCF binding (Ohlsson et al., *Trends Genet.*, 17:520-527, 2001).

Because gamma-satellite DNA from human chromosome 8 has a significant similarity to human gamma-satellite DNAs from chromosomes X and Y (Lin et al., *Chromosoma*, 102: 333-339, 1993; Lee et al., *Chromosoma*, 104:103-112, 1995; Lee et al., *Chromosoma*, 109:381-389, 2000), in vitro CTCF binding to other gamma-satellite DNA repeats was also analyzed. As seen in FIG. 5C, gamma-satellites X and Y contain functional CTCF binding sites.

To examine whether CTCF is recruited to gamma-satellite arrays in vivo, ChIP experiments were performed. A 4-5-fold enrichment for the gamma-satellite 8 DNA sequences was observed in dispersed, sheared chromatin of mouse RL5 cells carrying a 9 kb gamma-satellite array immunoprecipitated with a mixture of nine anti-CTCF mouse monoclonal antibodies (Pugacheva et al. *Hum. Mol. Genet.* 14:953-965, 2005), but not for alpha-satellite DNA (FIG. 5D). Control experiments were performed with RL5 cells carrying pYB cassette with alpha satellite DNA. Similar data for enrichments of endogenous gamma-satellite 8 sequences was obtained with human HT1080 cells (FIG. 5E). A modest but still significant enrichment was also observed for gamma-satellite arrays on chromosomes X and Y (FIG. 5E). These results suggest that CTCF may bind to human gamma-satellite DNA in vivo. Chromosomal fibers prepared from human HT1080 cells were also analyzed. Combination of FISH and immunostaining analysis confirmed that CTCF is co-localized with gamma-satellite 8 DNA (FIG. 5F). This possibility is consistent with immunostaining experiments demonstrating CTCF protein is enriched in the centromere regions of metaphase chromosomes (Burke et al., *EMBO J* 24:3291-3300, 2005).

Figure 16A:
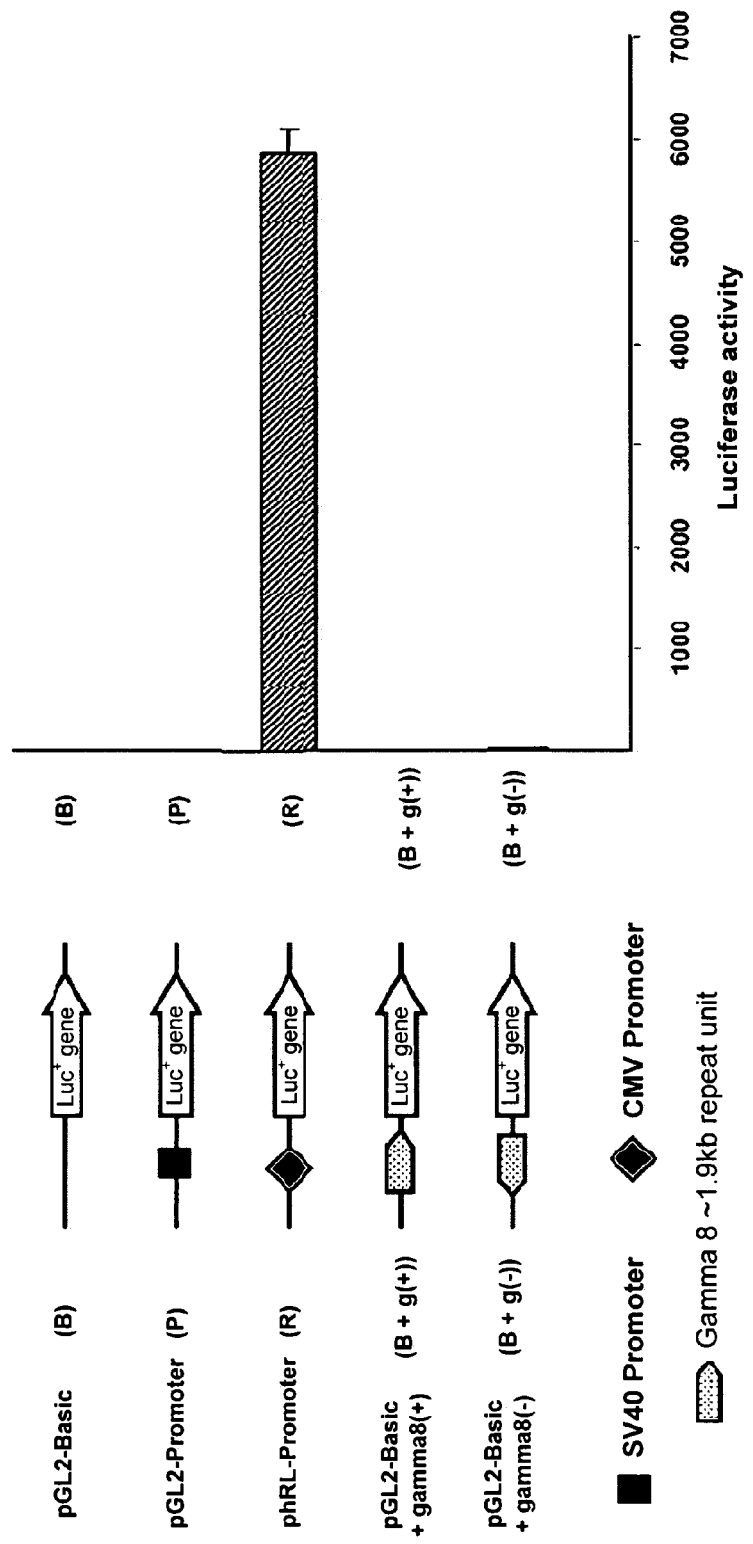
FIG. 16A demonstrates the promoter activity of gamma-satellite 8 DNA. The approximate 1.9 kb gamma-satellite 8 DNA fragment was linked to a firefly luciferase reporter gene in a pGL2-basic, or promoter vector, and transfected into mouse MEL cells with the *Renilla* luciferase gene in phRLCMV as an internal standard. The schematic structures of the vectors are shown in the left panel and the luciferase activity is shown in the right panel. Values are means±SD of three individual experiments in triplicates.
Figure 16B:
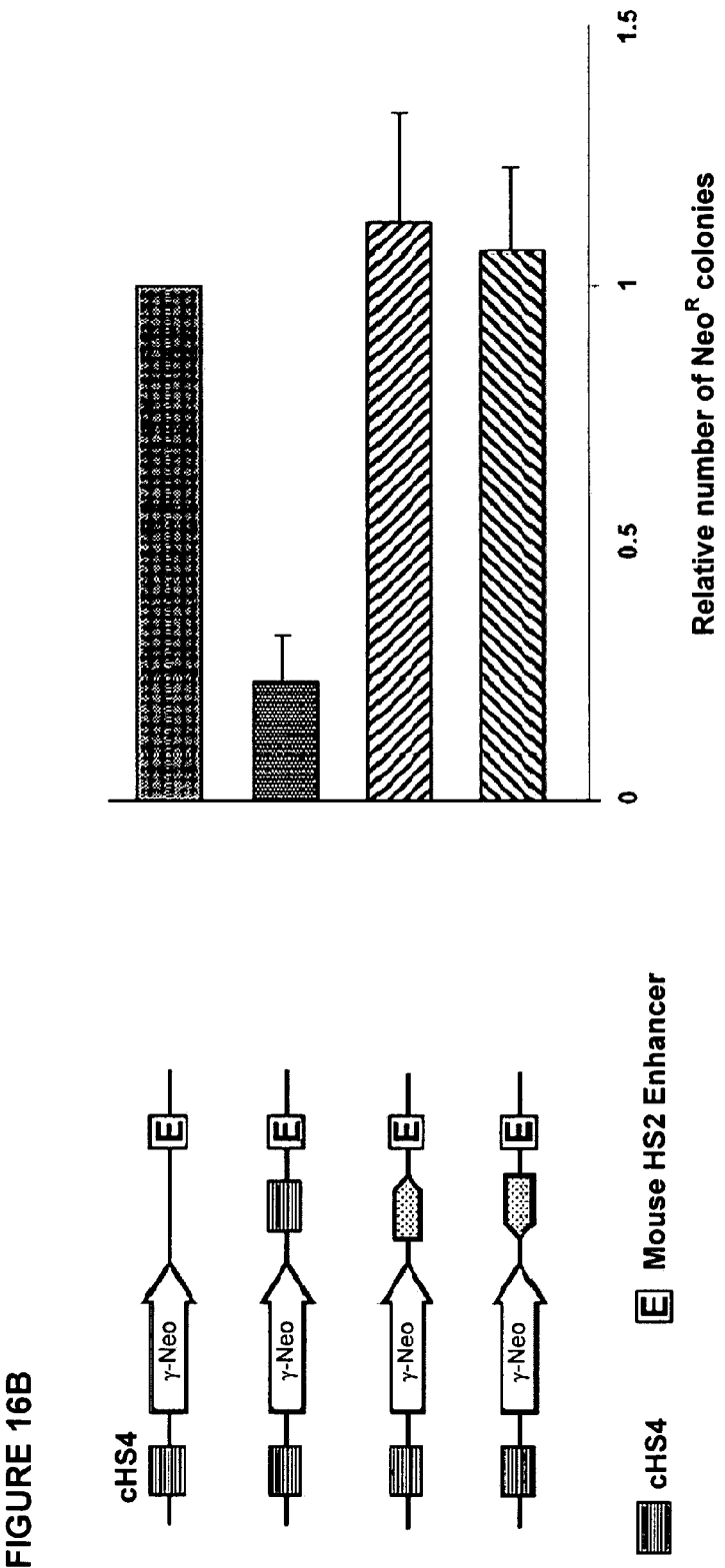
FIG. 16B is a schematic and graphic representation of an enhancer blocking assay. Enhancer blocking assays were performed as previously described (Chung et al., 1993; 1997). The approximately 1.9 kb human gamma 8 repeats were inserted into the SacI site between the mouse HS2 enhancer and human γ globin promoter neomycin gene. Before transfection, each construct was linearized by AatII endonuclease. The average colony number obtained is relative to constructs without cHS4 between the enhancer and γ-neomycin gene.
Figure 19:
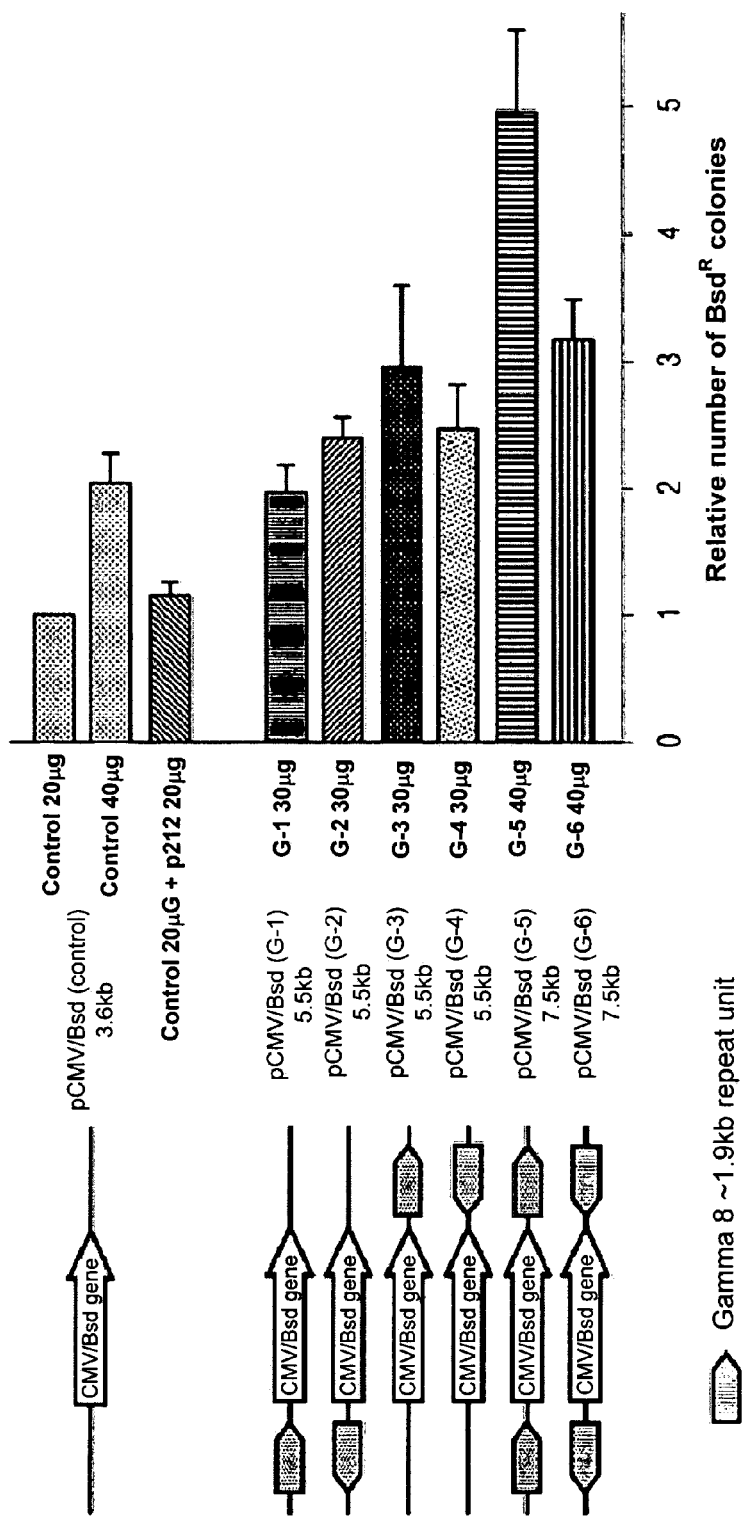
FIG. 19 is a graphical and schematic representation demonstrating that gamma-satellite DNA from human chromosome increases yield of stable transfectants. The left panel is a graphical representation of six vectors with human gamma-satellite DNA which were constructed using the pCMV/Bsd vector (CMV promoter/BlastocydinR gene) (Invitrogen). The approximately 1.9 kb gamma-satellite DNA fragment was cloned into either XhoI/BglII sites (upstream of CMV/Bsd gene) or into BamHI/XbaI sites (downstream of CMV/Bsd gene) producing G-1, G-2, G-3, and G-4 plasmids, respectively. Plasmids with the CMV/Bsd gene flanked by gamma-satellite fragments, G-5 and G-6, were also constructed. Before transfection, each vector was linearized by SspI digestion. The constructs were stably transfected into mouse MEL cells and Bsd-resistant colonies were counted. The right panel demonstrates the relative number of Bsd-resistant colonies. The number of colonies from the control construct pCMV/Bsd was arbitrarily set to 1.0. The construct containing two gamma-satellite DNA fragments flanking the Bsd gene exhibited a 3-5-fold increase in the number of Bsd-resistant colonies compared to the pCMV/Bsd vector alone. A different amount of the vector DNAs was used to equilibrate the vectors size.
Figure 20:
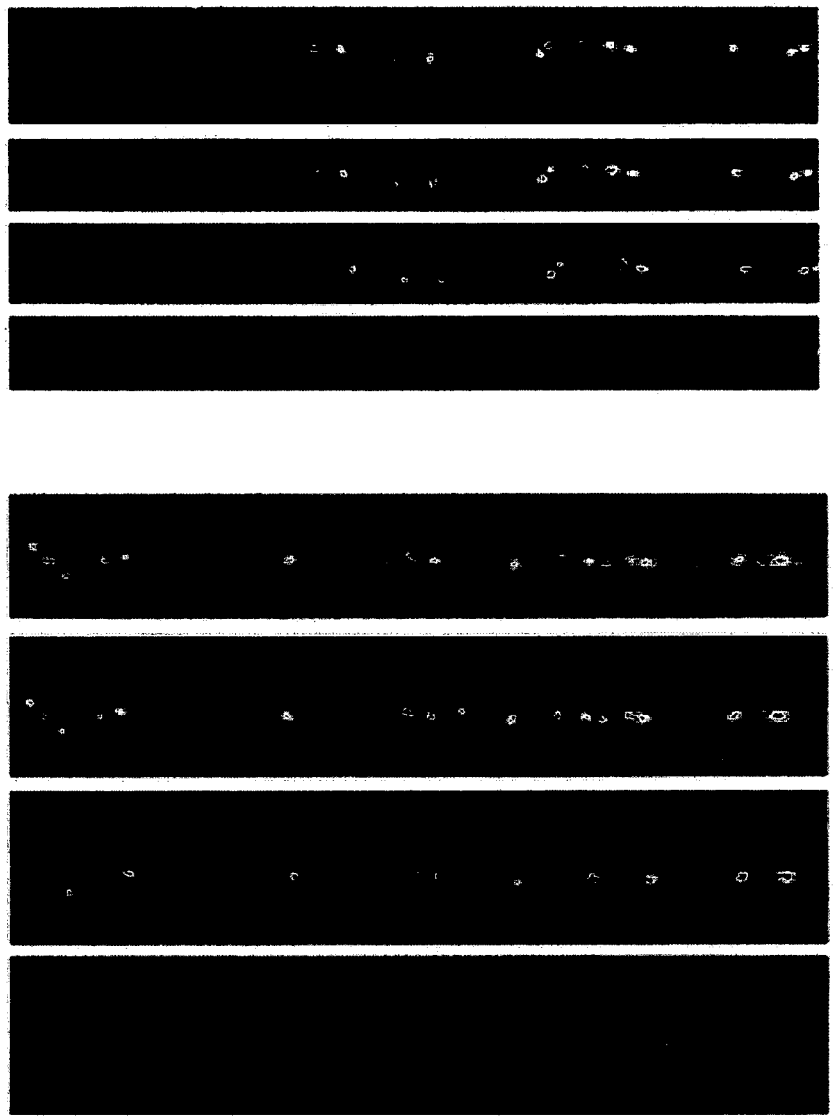
FIG. 20 is digital photo of Fiber FISH of human gamma-satellite 8. Optical mapping on extended chromatin fibers shows that CTCF occupies a fraction of the gamma-satellite 8 array. DNA is stained by DAPI.

Because gamma-satellite DNA contains CTCF sites, additional experiments were carried out to elucidate if gamma-satellite DNA functions as an enhancer-blocking insulator. An enhancer blocking activity of gamma-satellite DNA failed to be detected (FIG. 16B). At the same time, the inclusion of two copies of gamma-satellite DNA into the pCMV/Bsd vector increased the yield of transfectants (FIG. 19), suggesting that gamma-satellite DNA may help transgenes to escape from position variegation effects resembling a feature of barrier insulators (Chung et al. *Cell*, 74:505-514, 1993).

Based on both in vitro and in vivo observations and the conserved CTCF core sequence between gamma-satellite DNA from different chromosomes (FIG. 13A), it suggests that the CTCF protein has the target sites within pericentromeric regions of human chromosomes.

Gamma-Satellite Monomers are Functionally Diverged

In an attempt to determine if CTCF binding is needed for anti-silencing activity, a functional analysis of fragments derived from the 8-mer gamma-satellite DNA was carried out. The 8-mer (an amplified array which exhibited a strong anti-silencing activity, as described above) was sub-cloned as a set of overlapping fragments, the fragments were amplified into approximately 3 kb arrays, inserted into the ectopic RL5 site and then the eGFP transgene expression was measured (Table 14). All four overlapping 4-mers exhibited an activity similar to that for the original 8-mer. However, amplified 2-mers or monomers exhibited a significantly lower anti-silencing activity compared to 8- or 4-mer-based arrays. These results indicate that gamma-satellite monomers are not only structurally diverged (FIG. 12C) but also are likely functionally diverged and combination of more than two non-identical monomers is required for anti-silencing activity.

Therefore, the presence of a CTCF binding site alone is not sufficient for anti-silencing activity.

TABLE 14

Different Repeat Unit Composition of the pYB Gamma Vectors

| Repeat unit composition of the pYB Gamma vectors | Relative eGFP intensity |
| --- | --- |
| Amplified 8-mer (monomer 1-8) | 100% |
| Set of overlapping 4-mer (monomer 1-4, 3-6, 5-8, 7-2) | 93% |
| Set of overlapping 2-mer (monomer 3-4, 4-5, 5-6) | 46% |
| Monomer 8 CTCF WT (monomer 8 WT) | 35% |
| Monomer 8 CTCF MU (monomer 8 MU) | 51% |

Figure 6:
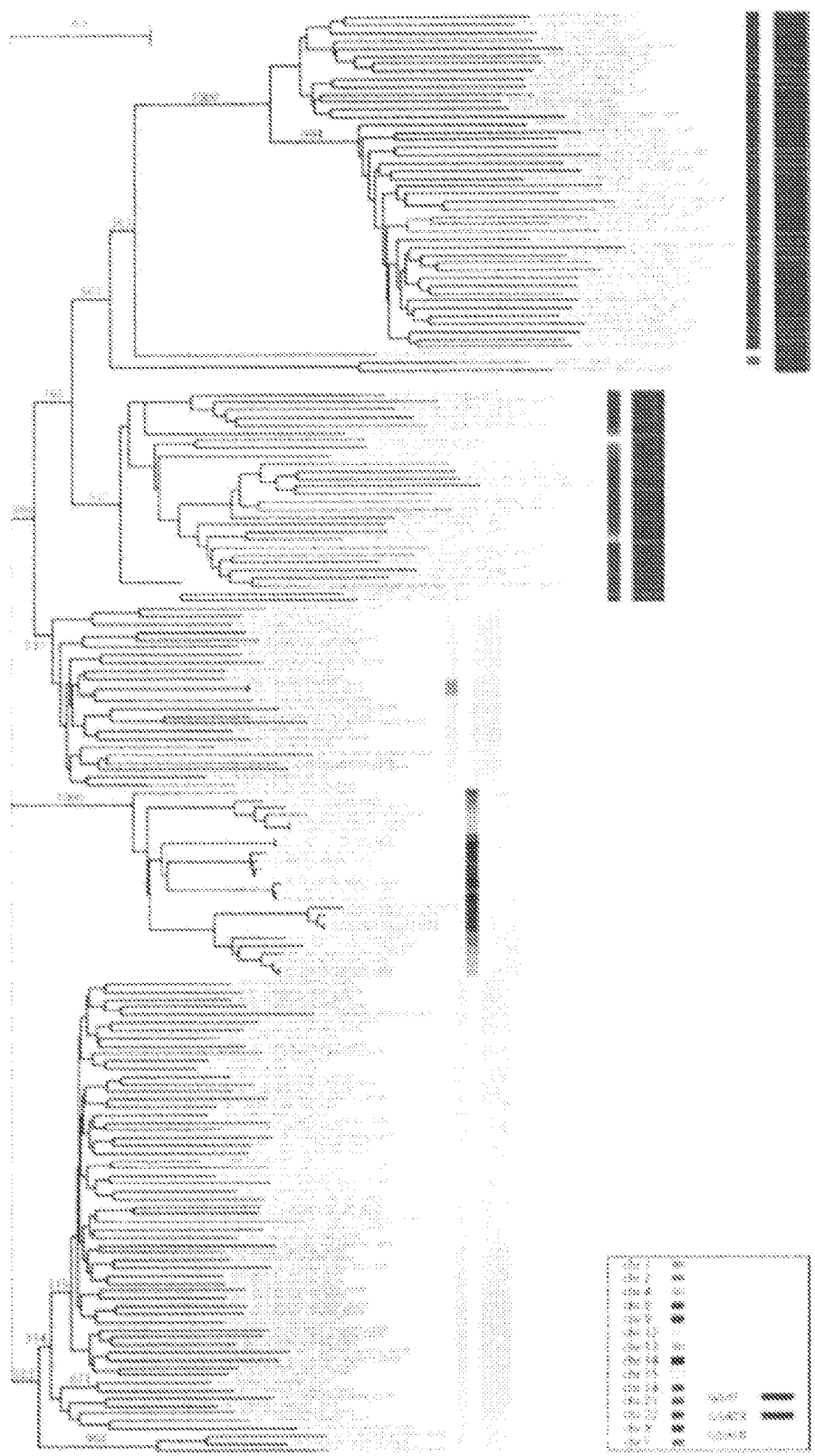
FIG. 6 is a schematic representation of the phylogenetic tree of human gamma-satellite repeats. GSAT, GSATII, and GSATX copies were extracted from the University of California at Santa Cruz human genome annotation. From each gamma-satellite array one monomer was selected and aligned in clustalw (Chema et al., *Nucl. Acids Res.* 31, 3497-500, 2003). Partial GSAT copies were excluded from the analysis.
Figure 17:
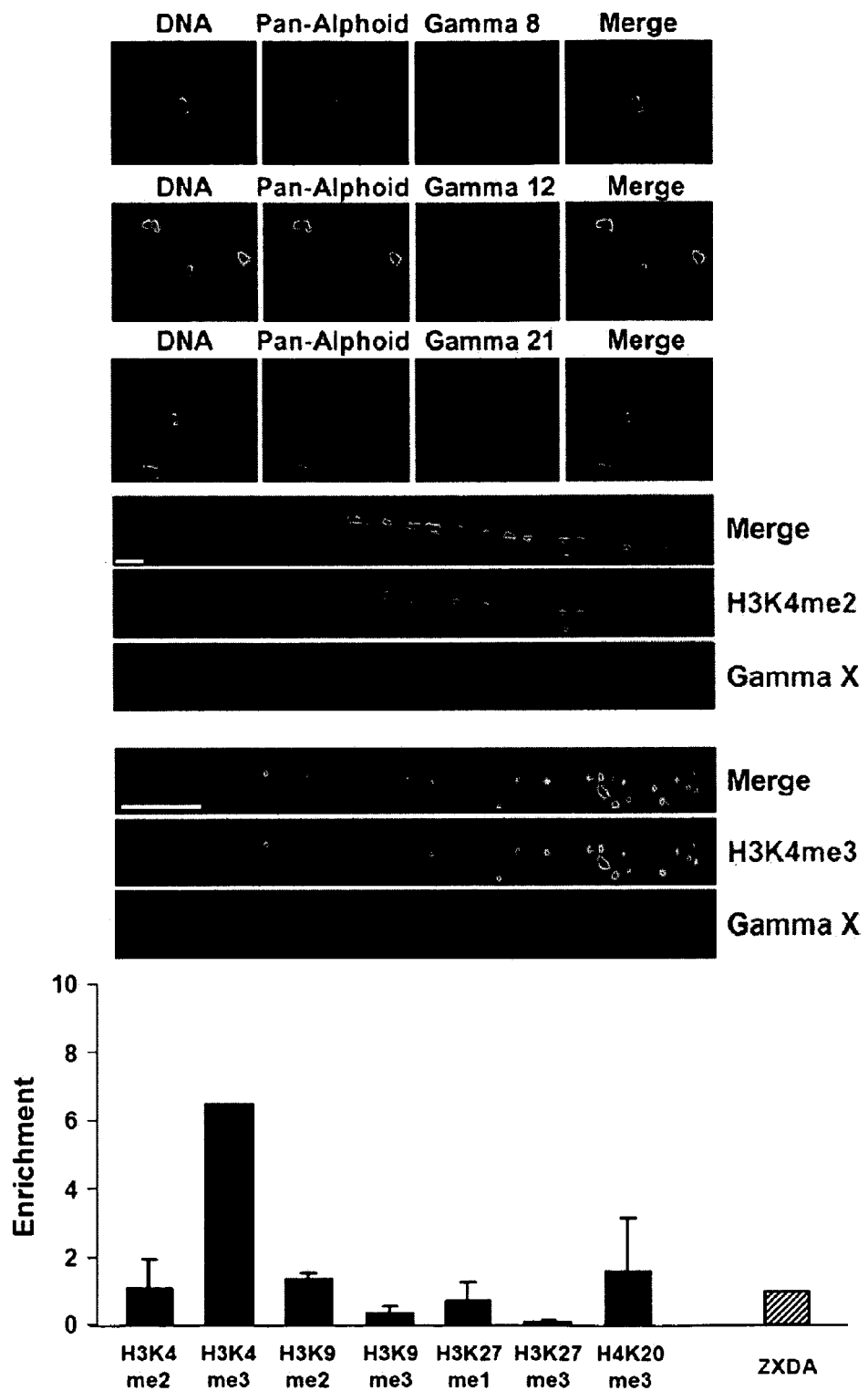
FIG. 17 is a series of digital photos and a graphical representation of an analysis of gamma-satellite DNA in human cells. The top three rows of digital images demonstrates the detection of gamma-satellite repeats localization by FISH analysis. Scale bar is 5 microns. A pan-alphoid probe is used to detect alpha-satellite repeats at the centromere. Gamma-satellite probes are specific for chromosomes 8, 12 or 21, respectively. DAPI stains DNA. The middle rows of digital images demonstrate that gamma satellite is incorporated into chromatin containing euchromatic histone modifications. Scale bar is 15 microns. IF-FISH on chromatin fibers was performed to spatially define the location of gamma satellite and histone markers of euchromatin on human chromosomes in human dermal fibroblasts. H3K4me2 antibody staining and H3K4me3 antibody staining co-localize with a DNA probe specific for the human X gamma satellite array. While chromatin containing H3K4 methylation is concentrated at the gamma satellite array, it also extends past the array, suggesting that nearby pericentromeric sequences are also incorporated into open chromatin. The graph (bottom panel) demonstrates ChIP analysis of gamma-satellite DNA arrays in human dermal fibroblasts. Enrichment was normalized to enrichment at a STS marker located near ZXDA, the most proximal human gene on Xp located in euchromatin just outside of the centromere region.
Figure 18:
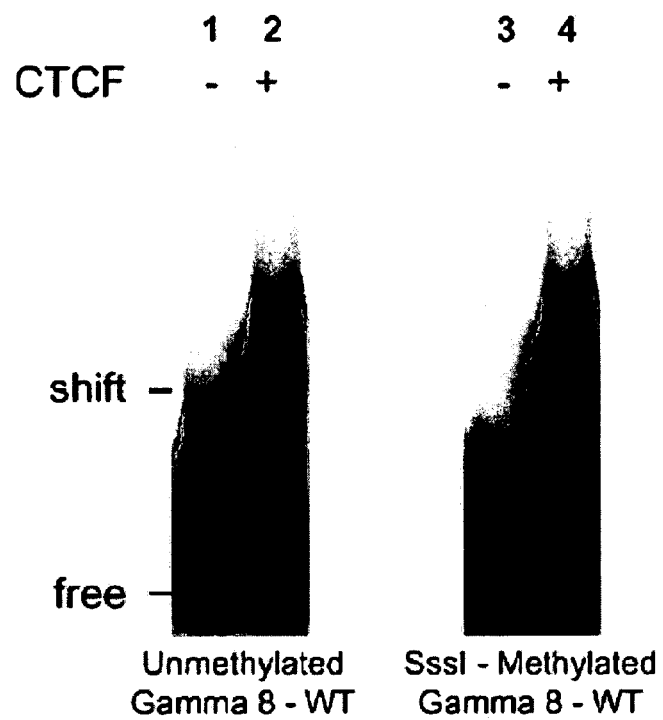
FIG. 18 is a digital image demonstrating that the binding of CTCF to gamma-satellite is independent of CpG methylation. Control unmethylated (lanes 1, 2) or SssI-methylated (lanes 3, 4) fragments were analyzed by gel-shift assay (EMSA). (−) free probe; (+) CTCF-bound probe. There are two CpG dinucleotides within a 55 bp CTCF core sequence (monomer 8th); one of them corresponds to the contact nucleotides identified by methylation interference (FIG. 12A).

Gamma-Satellite DNA is a Conserved Element of Pericentromeric Regions in Primates Given conservatism between gamma-satellite DNAs in chromosomes 8, X, and Y, a screen of gamma-satellite repeats in the human genome was performed. Unexpectedly, this analysis revealed the presence of gamma-satellite arrays in pericentromeric regions of 16 other human chromosomes (FIG. 6; Table 9). Using gamma-satellite DNA divergence, unique probes were designed for several human chromosomes, including chromosomes 12 and 21, for which the presence of gamma-satellite DNA was not previously reported. As seen from FIG. 17A, the probes position the repeats in the pericentromeric regions. Blocks of gamma-satellite DNA repeats were also detected in chimpanzee and rhesus macaque genomes. While the poor quality of assembled pericentromeric sequences did not allow positioning of all the repeats, in the cases where these repeats were mapped, they were localized in pericentromeric regions similar to that in humans. These data are summarized in Tables 10-13. Based on these results, it was concluded that gamma-satellite arrays are conserved elements of pericentromeric regions in primates.

TABLE 9

Location of Gamma-Satellite DNA Repeats in the Human Genome

| Chromosome | Number of repeats | Size of the genomic region harboring gamma-satellite monomers (in bp) |
| --- | --- | --- |
| 1 | 6 | 6241 |
| 2 | 2 | 3708 |
| 3 | 1 | 166 |
| 4 | 8 | 9356 |
| 5 | 2 | 181 |
| 6 | 1 | 96 |
| 8 | 68 | 269,539 |
| 9 | 8 | 21,040 |
| 10 | 1 | 148 |
| 12 | 151 | 121,456 |
| 13 | 1 | 1,935 |
| 14 | 3 | 5,495 |
| 15 | 3 | 642 |
| 17 | 1 | 155 |
| 18 | 1 | 461 |
| 21 | 1 | 2,955 |
| 22 | 3 | 2,779 |
| X | 16 | 39,099 |
| Y | 6 | 20,478 |

TABLE 10

Location of a Gamma-Satellite DNA Repeats in the Sequenced Part of the Chimpanzee Genome

| Chromosome | Number of repeats | Length in bp |
|---|---|---|
| 1 | 5 | 1,659 |
| 2a | 1 | 178 |
| 2b | 3 | 3,397 |
| 3 | 1 | 166 |
| 4 | 22 | 37,280 |
| 5 | 2 | 190 |
| 6 | 1 | 96 |
| 8 | 76 | 140,400 |
| 9 | 1 | 1,575 |
| 10 | 1 | 148 |
| 12 | 141 | 88,110 |
| 13 | 2 | 927 |
| 14 | 1 | 2,571 |
| 15 | 3 | 636 |
| 17 | 1 | 155 |
| 18 | 1 | 1,763 |
| 21 | 1 | 2,948 |
| 22 | 1 | 1,467 |
| X | 15 | 16,076 |
| Y | 14 | 20,978 |

TABLE 11

Gamma-Satellite DNA Repeats in the Sequenced Part of the Chimpanzee Genome by Families

| Chromosome | Family | Number of repeats | Length in bp |
|---|---|---|---|
| 1 | GSAT | 1 | 92 |
| 1 | GSATII | 2 | 1,371 |
| 1 | GSATX | 2 | 196 |
| 2a | GSAT | 1 | 178 |
| 2b | GSAII | 3 | 3,397 |
| 3 | GSATX | 1 | 166 |
| 4 | GSAT | 2 | 302 |
| 4 | GSATX | 20 | 36,978 |
| 5 | GSATX | 2 | 190 |
| 6 | GSATX | 1 | 96 |
| 8 | GSAT | 60 | 117,379 |
| 8 | GSATX | 16 | 23,021 |
| 9 | GSATII | 1 | 1,575 |
| 10 | GSAT | 1 | 148 |
| 12 | GSAT | 1 | 135 |
| 12 | GSATII | 120 | 75,553 |
| 12 | GSATX | 20 | 12,422 |
| 13 | GSAT | 1 | 176 |
| 13 | GSATX | 1 | 751 |
| 14 | GSATII | 1 | 2,571 |
| 15 | GSAT | 2 | 513 |
| 15 | GSATX | 1 | 123 |
| 17 | GSAT | 1 | 155 |
| 18 | GSATX | 1 | 1,763 |
| 21 | GSATX | 1 | 2,948 |
| 22 | GSATX | 1 | 1,467 |
| X | GSATX | 15 | 16,076 |
| Y | GSAT | 1 | 118 |
| Y | GSATX | 13 | 20,860 |

TABLE 12

Location of Gamma-Satellite DNA Repeats in the Sequenced Part of the Rhesus Macaque Genome

| Chromosome | Number of repeats | Length in bp |
|---|---|---|
| 2 | 1 | 170 |
| 3 | 15 | 27,512 |
| 4 | 1 | 97 |
| 5 | 27 | 53,361 |
| 6 | 1 | 81 |
| 7 | 4 | 1,262 |
| 8 | 14 | 51,275 |
| 9 | 7 | 2,598 |
| 12 | 2 | 226 |
| 13 | 2 | 290 |
| 16 | 1 | 164 |
| 17 | 1 | 151 |
| 18 | 1 | 911 |
| 19 | 1 | 2,376 |

TABLE 13

Gamma-Satellite DNA Repeats in the Sequenced Part of the Rhesus Macaque Genome by Families

| Chromosome | Family | Number of repeats | Length in bp |
|---|---|---|---|
| 2 | GSATX | 1 | 170 |
| 3 | GSATII | 15 | 27,512 |
| 4 | GSATX | 1 | 97 |
| 5 | GSAT | 3 | 448 |
| 5 | GSATII | 1 | 60 |
| 5 | GSATX | 23 | 52,853 |
| 6 | GSATX | 1 | 81 |
| 7 | GSAT | 2 | 560 |
| 7 | GSATX | 2 | 702 |
| 8 | GSAT | 12 | 48,854 |
| 8 | GSATII | 2 | 2,421 |
| 9 | GSAT | 2 | 331 |
| 9 | GSATII | 5 | 2,267 |
| 12 | GSATII | 2 | 226 |
| 13 | GSAT | 1 | 171 |
| 13 | GSATII | 1 | 119 |
| 16 | GSAT | 1 | 164 |
| 17 | GSAT | 1 | 151 |
| 18 | GSATX | 1 | 911 |
| 19 | GSATX | 1 | 2,376 |

Chromosome X Gamma-Satellite DNA is Incorporated into Chromatin Containing Euchromatic Histone Modifications.

To elucidate chromatin organization of gamma-satellite DNA in its natural location, gamma-satellite DNA in the human chromosome X was analyzed. Pericentromeric regions of this chromosome are the most characterized (Schueler et al., 2001; 2005). Chromosome X gamma-satellite DNA is not interspersed with other types of repeats, but rather is organized as a single array of approximately 30 kb on the short-arm side of the alphoid satellite domain. First, the distribution of H3K4me2, H3K4me3, H3K9me2, H3K9me3, H3K27me1, H3K27me3 and H4K20me3 at gamma-satellite DNA in human dermal fibroblasts was analyzed by ChIP and semi-quantitative PCR. Gamma-satellite DNA was enriched for H3K4me3 which defines euchromatin.

Discussion

Despite great progress in structural genomics, function of most of multiple repetitive DNA elements in the mammalian centromeres remains obscure. In an attempt to shed light on their role in organization and maintenance of centromere, a novel approach comparing the influence of different repetitive centromeric and pericentromeric DNA elements on neighboring genomic sequences in a controlled manner was developed. The analysis used a combination of recombinase-mediated cassette exchange system (RMCE; a tool for exchanging selectable DNA cassettes at a specific target site in chromosomal DNA), allowing to target the desired DNAs into the same genomic site (Feng et al., *Mol. Cell. Biol.*, 21:298-309, 2001), and an in vivo recombination technique, allowing construction of long synthetic DNA arrays (Ebersole et al., *Nuc. Acids Res.,* 33, e1302005). The results demonstrated that the presence of human and mouse pericentromeric DNA repeats blocks vector DNA-induced epigenetic silencing of the transgene cassette.

In this study, the strongest anti-silencing effect was observed with GC-rich gamma-satellite DNA from human chromosome 8. By comparison, a weaker anti-silencing activity was detected for the arrays containing mouse major satellite DNA or chicken HS4 insulator DNA. In contrast, long arrays of human alpha-satellite DNA did not exhibit a detectable effect on the transgene expression. The anti-silencing effect cannot be explained by up-regulation of the transgene transcription in the gamma-satellite DNA constructs. No promoter activity was detected within gamma-satellite DNA. Enhancer hypothesis cannot explain open chromatin structure of gamma-satellite DNA at its natural position, as well as a dependence of the anti-silencing effect on multiple copies of repeat units.

ChIP experiments show that the presence of arrays of gamma-satellite DNA induces a transcriptionally permissive chromatin conformation in the transgene cassette, but does not affect the condense chromatin structure of the vector DNA. Thus, gamma-satellite DNA protects the transgene from the spreading of heterochromatin from vector backbone DNA sequences. This hypothesis is supported by a specific pattern of H3K9me3 modification of the transgene cassette carrying gamma-satellite DNA in the RL5 locus. A progressive decrease of H3K9me3 from the YAC/BAC vector to the transgene is in accordance with a mechanism of an active spreading of heterochromatin from the vector sequence towards the transgene and its progressive trapping within gamma-satellite arrays.

Finding of recognition sites for the transcriptional factor CTCF in gamma-satellite monomers and demonstration of in vivo occupancy of gamma-satellite DNA by this protein explains the observed anti-silencing effect. CTCF is a highly conserved eleven zinc-finger (ZF) transcription factor with complex DNA-binding sequence specificity. CTCF target sites have been characterized in the promoters, silencers, and other regulatory regions of several genes (Ohlsson et al., *Trends Genet.,* 17:520-527, 2001). Because CTCF has multiple functions, the anti-silencing effect of gamma-satellite arrays in the mouse MEL cells discovered herein reflects a novel function of CTCF, i.e. silencer blocking or capability to shelter the transgene from the effect of silencers. In addition, this analysis identified a protein, CTCF, which recognizes centromeric repeats in human genome. Until now, CENP-B was the only known protein to specifically bind centromeric DNA (Earnshaw and Rothfield, *Chromosoma,* 91:313-321, 1985; Masumoto et al., *Chromosome Res.,* 12:543-556, 2004). Depending on the promoter context and cell background, CTCF may repress or activate transcription, though its repression function was reported more frequently. Ling et al. (*Science,* 312:269-272, 2006) also demonstrated that CTCF is capable of mediating an interchromosomal association. Notably, CTCF is the only mammalian protein identified so far that exhibits enhancer blocking activity via binding to the insulator elements which are located between enhancer and promoter elements (Bell et al., *Cell,* 98: 387-396, 1999; Bell and Felsenfeld, *Nature,* 405:482-485, 2000; Lutz et al., *EMBO J.,* 22:1579-1587, 1998).

In the human genome, gamma-satellite arrays represent a significant fraction of potential CTCF targets. A search of the UCSC human genome annotation database identified gamma-satellite DNA blocks in pericentromeric regions of most human chromosomes except chromosomes 7, 11, 16, 19, and 20. Gamma-satellite DNA is organized in arrays up to 270 kb interspersed with highly divergent or non-gamma satellite DNAs. Monomers within each array have average pairwise sequence identities of approximately 85% and are related to one of three subfamilies: GSAT, GSATX, and GSATII (FIG. 6; FIG. 13B). Homology between the gamma-satellite subfamilies is approximately 60%. If 10% of gamma-satellite monomers contain a CTCF consensus sequence, several hundred potential CTCF binding sites may exist in gamma-satellite DNA on pericentromeric regions of human chromosomes. This is consistent with immunostaining experiments, demonstrating that CTCF protein is enriched in the centromere regions of all metaphase chromosomes (Burke et al. *EMBO J.,* 24:3291-3300, 2005). Therefore, CTCF binding sites may be a prerequisite of all pericentromeric regions, and thus may contribute to a mosaic chromatin structure in the mammalian centromere.

While it was demonstrated that each gamma-satellite monomer contains the CTCF recognition site, not all monomers are functionally identical. A strong anti-silencing activity was observed only for amplified 8- and 4-mers of gamma-satellite DNA. Arrays generated from a 2-mer or a monomer failed to prevent the transgene silencing, indicating a functional divergence of monomers. This suggests that a sequence divergence between monomers (FIG. 12C) may create alternative binding sites that are recognized by different combinations of the CTCF zinc-fingers and a certain combination of these sites determines a specific "code" for anti-silencing activity of gamma-satellite arrays. Future analysis will elucidate a role of CTCF in anti-silencing activity within gamma-satellite DNA and whether other DNA-binding proteins also contribute this activity.

Whatever the role of CTCF binding in the prevention of the transgene silencing in mouse MEL cells, the presence of gamma-satellite DNA in pericentromeric regions of most human chromosomes suggests a functional significance. Failure to detect gamma-satellite DNA in four chromosomes may be due to the poor characterization and/or annotation of pericentromeric regions. Gamma-satellite DNA is organized in arrays of up to 270 kb interspersed with highly divergent or non-gamma satellite DNA. Monomers within each array have average pairwise sequence identities of approximately 85% and are related to one of three subfamilies, GSAT, GSATX, and GSATII. Homology between the gamma-satellite subfamilies is approximately 60% (FIG. 13B). Based on our results and those presented elsewhere (Lee et al, 1999; Schueler et al, 2005), organization of gamma-satellite DNA seems to be conserved in primates.

So far very few elements with a similar anti-silencing activity (designated as insulator elements) have been described in mammalian genomes (Chung et al, *Proc Natl Acad Sci USA* 94:575-58, 1997; West et al, *Genes Dev* 16:271-288, 2002; Gaszner and Felsenfeld, *Nat Rev Genet* 7: 703-713, 2006). By definition, insulators are DNA sequence elements that prevent inappropriate interactions between adjacent chromatin domains. One type of insulator establishes domains that separate enhancer and promoters to block their interaction, whereas a second type creates a barrier against the spread of heterochromatin. Gamma-satellite DNA does not fit exactly either of these types. First of all, the analysis did not reveal an enhancer blocking activity of gamma satellite DNA. Secondly, a barrier insulator must flank both 5' and 3' ends of the transgene to prevent epigenetic silencing. Therefore, the term "a heterochromatin arresting repeat element" is used to describe the behavior of gamma-satellite DNA.

The results presented here strongly indicate that at least some gamma-satellite DNA arrays in their natural location in human cells exist in a transcriptionally-permissive state. This is the first observation when large segments of pericentromeric repeated DNA in human chromosomes may escape heterochromatinization. Such blocks of open chromatin may have implications for chromosome function. For example, gamma-satellite DNA may prevent pericentric heterochromatin from spreading into chromosomal arms and suppressing expression of essential genes located close to the pericentromere. Another function of gamma-satellite arrays may be separation of specific domains of chromatin/heterochromatin to create a fully functional centromere. These results may also indicate that active genes exist within pericentromeric regions or that pericentromeric repeats themselves generate functional transcripts. Such transcripts may play a role in maintaining heterochromatin by RNA interference, as has been shown in fission yeast (Martienssen et al., *Trends Genet.*, 21450-456, 2005), and/or that arrays of gamma-satellite DNA prevent pericentric heterochromatin from spreading into chromosomal arms and suppressing expression of essential genes located close to the pericentromere.

This study provides insight into a possible functional role of pericentromeric repetitive DNA elements. Further elucidation of the function of gamma-satellite DNA arrays may benefit from the use of human artificial chromosomes (HACs) (Harrington et al, 1997; Ikeno et al, 1998; Willard, 2000; Basu and Willard, 2005), at least in part because distinct chromatin structures assemble on mitotically stable HACs in human cells. For example, CENP-A chromatin clusters assemble preferentially on HAC associated alphoid DNA, whereas heterochromatin clusters assemble preferentially on HAC-associated vector DNA (Ikeno et al, 1998; Grimes et al, 2004; Nakashima et al, 2005). Future analysis of HAC constructs carrying gamma-satellite and other DNA arrays may provide insight into how different chromatin domains are established and maintained in the human centromere and into the dynamics between heterochromatic and euchromatic domains in the mammalian chromosome.

Figure 14B:
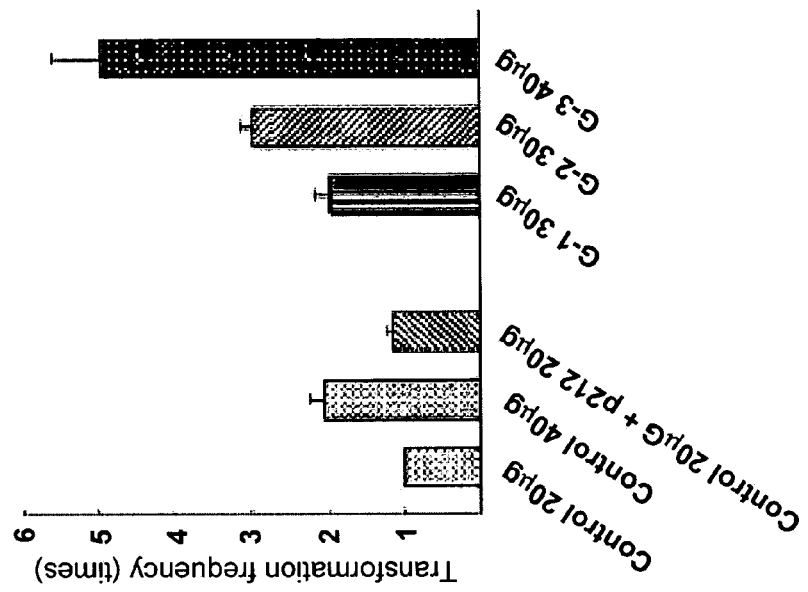
FIG. 14B demonstrates the relative number of Bsd-resistant colonies. The number of colonies from the control construct pCMV/Bsd was arbitrarily set to 1.0. The construct containing two gamma 8 repeats flanking the Bsd gene revealed a 5-fold increase in the number of Bsd-resistant colonies compared to the pCMV/Bsd vector alone. A different amount of the vector DNAs was used to equilibrate the vectors size.
Figure 14A:
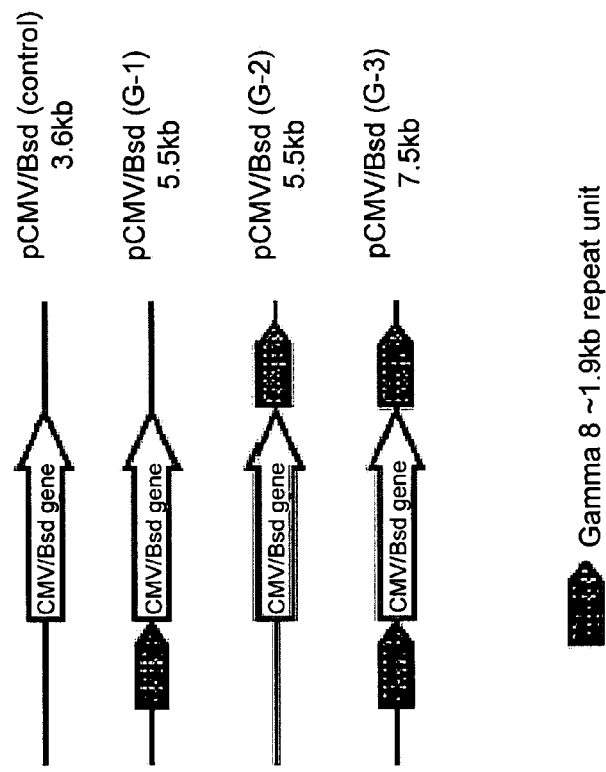
FIG. 14A is a schematic drawing of three different vectors with an approximately 1.9 kb human gamma 8 repeat (solid arrows) which were constructed using the pCMV/Bsd vector (CMV promoter/Blastocydin$^R$ gene) (Invitrogen). The approximate 1.9 kb gamma 8 fragment was cloned into 5' region (XhoI/BglII) or 3' region of CMV/Bsd gene (BamHI/XbaI) of the pCMV/Bsd vector producing pCMV/Bsd (G-1), pCMV/Bsd (G-2) and pCMV/Bsd (G-3) plasmids, correspondingly. Before transfection, each vector was linearized by SspI enzyme. The constructs were stably transfected into mouse MEL cells and Bsd-resistant colonies were counted.

Discovery of the anti-silencing (insulating) activity of gamma-satellite arrays will have an important impact on developing successful systems for continued transgene expression in gene therapy procedures. Thus, a promising approach to overcome the limitations experienced with current gene therapy procedures is the protection of transgene expression using insulators. It is provided herein that gamma-satellite repeats exhibit a strong anti-silencing (insulating) effect. Moreover, it is also provided herein that flanking of the Neo cassette with gamma-satellite DNA resulted in a significant increase of yield of G418 colonies (FIG. 14). Thus, gamma-satellite DNA exhibits insulating activity.

Example 2

In vitro Prevention of Gene Silencing

This example describes a non-limiting method for preventing gene silencing in vitro. Though the example is given in the context of expressing transgenes, such as α-globin, β-globin, Vascular Endothelial Growth Factor (VEGF), adenosine deaminase, or HIV-related transgenes in human CD34+ cells, it will be understood by one of ordinary skill in the art that the method could also be practiced in other cell types and for the expression of other transgenes.

Plasmids

Plasmid construction and transfections are performed using standard molecular biology techniques (Ausubel et al. *Current Protocols in Molecular Biology* (2006), John Wiley & Sons, Inc.). Insulator (for example, human gamma satellite DNA, or a consensus sequence of the human gamma satellite DNA containing a CTCF-binding sequence or an Ikaros protein-binding sequence) and transgene sequences, such as α-globin, β-globin, Vascular Endothelial Growth Factor (VEGF), adenosine deaminase, or HIV-related transgenes, under control of a promoter, for example the human β-globin promoter, are inserted into a vector (transgene construct), for instance, the pYB targeting cassette using standard methodology; an example of such methodology is described above in Example 1.

Cell Culture and Transformation

Human CD34+ cells carrying a counter-selectable marker, HYTK, flanked by inverted lox-P sites in the predefined chromosomal sites are maintained in growth medium, e.g. DMEM (Invitrogen 11965) with 10% FBS (Hyclone) at 37° C. in 7.5% $CO_2$. The cells are maintained in 700 μg/ml Hygromycin B (Invitrogen). The presence of the lox-P-containing cassette allows integration of transgenes and insulator sequences into the predefined chromosomal sites at high efficiency using a recombinase-mediated cassette exchange (RMCE) system after induction of the Cre recombinase (Schubeler et al., *Mol Cell Biol.* 20:9103-9112, 2000; Feng et al., *Mol. Cell. Biol.*, 21:298-309, 2001; Eszterhas et al., *Mol Cell Biol.*, 22:469-479, 2002).

The transgene construct is transfected into the target cell (human CD34+ cells in this example), for instance using electroporation, as described in Example 1. Selection for loss of the HYTK gene with 10 μM Gancyclovir begins approximately 48 hours post electroporation. Gancyclovir resistant clones are expanded and tested for targeted recombination by PCR. Clones are the subject of FACS analysis and southern blotting for further analysis of genomic organization, as appropriate.

FACS Analysis

FACS analysis of transgene expression is performed on a FACSCalibur instrument (BD Biosciences) under the control of CellQuest™ acquisition software (BD Bioscience) acquisition software and analyzed statistically with FlowJo software (Feng et al., *Mol. Cell. Biol.* 21:298-309, 2001). A minimum of $4 \times 10^4$ cells are analyzed for each cell line at 487 nm. When the transgene construct (insulator and transgene sequences) exchanges into the target locus in CD34+ cells, the transgene is expressed at high levels, compared to cells which include a construct without insulator sequences. For cells with both insulator and transgene sequences, the level of transgene expression is stable for many months.

Example 3

Ex vivo Prevention of Gene Silencing by Transduction of Human CD34+ Cells Using Adenoviral Vectors Ex vivo methods can be used to introduce a transgene construct of interest into autologous or heterologous cells, which can be subsequently introduced into a subject to treat a disease. For example, ex vivo methods for introducing an adenoviral vector containing the β-globin transgene in a subject having sickle cell anemia involve transducing $CD34^+$ cells ex vivo, and then introducing the transduced $CD34^+$ cells into the subject.

Human gamma satellite DNA sequences prevents silencing of the β-globin gene in the transduced $CD34^+$ cells, thereby maintaining expression of the gene. Adenovirus particles having adenoviral vectors including a human gamma satellite DNA sequence, or a consensus sequence of the human gamma satellite DNA sequence containing a CTCF-binding sequence or an Ikaros protein-binding sequence, are used to transduce autologous cells isolated from a subject having sickle cell anemia. Alternatively, the cells are heterologous cells, such as CD34+ cells stored in an umbilical cord blood bank or a bone marrow bank. Transduced CD34+ cells are delivered to the subject by standard methods.

This example describes a non-limiting method of preventing gene silencing in a subject, using cells that have had a transgene construct introduced ex vivo with an adenoviral vector. Though the example is given in the context of expressing β-globin in human CD34+ cells, it will be understood by one of ordinary skill in the art that the method could also be practiced in other cell types and for the expression of other transgenes.

CD34+ Cell Purification:

By way of example, 15-20 mL bone marrow aspirates are obtained from a subject having sickle cell anemia after informed consent. Cells are diluted 1:3 in phosphate buffered saline (PBS, Gibco-BRL), 30 mL are layered over 15 mL Histopaque-1077 (Sigma) and centrifuged for 30 minutes at 300 RCF. The mononuclear interface layer is collected and washed in PBS. CD34+ cells are enriched from the mononuclear cell preparation using an affinity column per manufacturers' instructions (CellPro, Inc, Bothel, Wash.). After enrichment, the purity of CD34+ cells is expected to be 70% on average, as determined by flow cytometric analysis using anti CD34 monoclonal antibody conjugated to fluorescein (Becton Dickinson, San Jose, Calif.).

Cells are resuspended at 40,000 cells/mL in X-Vivo 10 media (Bio-Whittaker, Walkersville, Md.) and 1 mL is plated in 12-well tissue culture plates (Costar). The growth factor IL-3 is added at 100 ng/mL to the cells. Cells are incubated at 37° C. for 8-14 days at 5% $CO_2$ in a 37° C. humidified incubator. At the end of the culture period a total cell count is obtained.

Transduction and Administration of CD34+ Cells

CD34+ cells are plated at a concentration of $5 \times 10^4$ cells per well of 24-well plates, and maintained in culture for 24 hours. CD34+ cells are subsequently exposed to 1000 adenovirus particles having adenoviral vectors including the insulator and transgene sequences. Forty-eight hours after virus addition, cells are harvested and tested for integration of the transgene cassette into the CD34+ cell genome using standard PCR techniques and for human β-globin expression using standard immunocytochemistry and Northern blot techniques. Transduced CD34+ cells expressing β-globin are administered intravenously into the subject having sickle cell anemia using standard protocols.

Example 4

Transduction of Human CD34+ Cells Using Adeno-Associated Virus ("AAV") Vectors

This example describes a non-limiting method of preventing or delaying gene silencing in a subject, using cells that have had a transgene construct introduced ex vivo with an adeno-associated virus (AAV) vector. Though the example is given in the context of expressing transgenes, such as α-globin, β-globin, Vascular Endothelial Growth Factor (VEGF), adenosine deaminase, or HIV-related transgenes in human CD34+ cells, it will be understood by one of ordinary skill in the art that the method could also be practiced in other cell types and for the expression of other transgenes.

Recombinant viral vectors containing the transgene construct (including an insulator sequence, such as human gamma satellite DNA or a consensus sequence of the human gamma satellite DNA containing a CTCF-binding sequence or an Ikaros protein-binding sequence, and a transgene sequence of interest) are encapsidated using a helper virus. Briefly, semi-confluent cultured 293T cells are infected with helper virus and transfected 1 hour post-infection with 20 µg of the vector plasmids by calcium phosphate co-precipitation (CellPhect; Pharmacia Biotech, Uppsala, Sweden). AAV-encoded rep (DNA replication) and cap (capsid proteins) gene functions are provided in trans. Cells are harvested 72 hours post-transfection and are lysed by three cycles of freeze-thawing and sonication. Vector stocks are treated to digest residual plasmid and cellular DNA and particle titers are determined by dot blot analysis. Functional titers are determined by quantitation of specific alkaline phosphatase expressing cells and neomycin resistant (NeoR) colonies after serial dilutions on cultured cells. All helper virus stocks and cell lines are screened for wild-type AAV contamination.

CD34+ cells are purified and isolated from a subject, as described in Example 3, and transduced immediately upon isolation. Transductions are performed by the direct addition of vector to cells and left undisturbed for 24 to 48 hours, after which cells are washed and replated. Cells are then harvested and tested for integration of the insulator/transgene cassette into the CD34+ cell genome using standard PCR techniques and for transgene expression using standard immunocytochemistry and Northern blot techniques. Transduced CD34+ cells expressing the transgene are administered into the subject using standard protocols.

Example 5

Transduction of Mammalian Stem Cells Using Lentiviral Vectors

This example describes a non-limiting method of preventing gene silencing in a subject, using stem cells that have had a transgene construct introduced ex vivo with a lentiviral vector.

Lentiviral vector stocks are produced by transient co-transfection into 293T cells. Briefly, a total of $5 \times 10^6$ 293T cells are seeded in 10-cm-diameter dishes 24 hours prior to transfection in appropriate medium (e.g., Iscove modified Dulbecco culture medium (JRH Biosciences) with 10% fetal bovine serum, penicillin (100 IU/ml), and streptomycin (100 µg/ml)) in a 5% $CO_2$ incubator, and the culture medium is changed 2 hours prior to transfection. A total of 20 µg of plasmid DNA is used for the transfection of one dish: 3.5 µg of envelope plasmid, 6.5 µg of packaging plasmid, and 10 µg of transfer vector plasmid (including an insulator sequence, such as a human gamma satellite DNA sequence or a consensus sequence of the human gamma satellite DNA sequence containing a CTCF-binding sequence or an Ikaros protein-binding sequence, and a transgene sequence of interest). A precipitate is formed and is immediately added to the cultures. The medium is replaced after 14 to 16 hours; the virus containing medium is collected after another 24 hours, cleared by low-speed centrifugation, and filtered through 0.22-µm-pore-size cellulose acetate filters. Vector batches are tested for the absence of replication-competent virus using known techniques. Viral titers may be determined, for instance by infecting mouse erythroleukemia (MEL) cells, using serial dilution of concentrated virus, differentiating them, and analyzing them for transgene expression by fluorescence-activated cell-sorter scanner (FACS) and a semi-quantitative PCR.

Filtered vector-containing medium can then be used for introducing a transgene of interest into cells. By way of example, filtered vector-containing medium, at a multiplicity of infection (MOI) ranging from 1 to 14 and at a viral concentration of $3\times10^7$ to $2\times10^8$ IU/mL, is added to seeded mammalian stem cells, such as hematopoietic CD34$^+$ cells or embryonic stem cells, and is left until cells are analyzed 48 to 60 hours later. Cells are then harvested and tested for integration of the insulator/transgene cassette into the genome using standard PCR techniques, and for transgene expression using standard immunocytochemistry and/or Northern blot techniques.

By way of examples, cells are fixed for 60 minutes at room temperature, washed once with phosphate-buffered saline (PBS), and resuspended in 50 μL 100% methanol for 5 minutes. The fixed cells are then washed with PBS, and nonspecific antibody binding is blocked (e.g., using 75 μL 5% nonfat milk for 10 minutes at room temperature). Subsequently, cells are washed in PBS, pelleted, and permeabilized. The cells are stained with either a negative control antibody or an antibody against the transgene product, and unbound antibodies are removed by a final wash with PBS before they are analyzed by FACS. Transduced stem cells expressing the transgene are administered into the subject using standard protocols.

This disclosure provides novel strong insulator sequences, which can be used to inhibit gene silencing. It will be apparent that the precise details of the methods and compositions described may be varied or modified without departing from the spirit of the described invention. We claim all such modifications and variations that fall within the scope and spirit of the claims below.

---

We claim:

1. A method of inhibiting silencing of a coding nucleic acid sequence to be expressed in a recipient cell, comprising: introducing into a chromosomal site in the recipient cell a transgene construct comprising a coding nucleic acid sequence to be expressed in the recipient cell, wherein the coding nucleic acid sequence is flanked on each of its 5' and 3' ends by at least six repeats of a human gamma-satellite DNA monomer that is heterologous to the coding nucleic acid sequence, and wherein the at least six repeats of a human gamma-satellite DNA monomer inhibits silencing of expression of the coding nucleic acid sequence, thereby inhibiting silencing of the coding nucleic acid sequence to be expressed in the recipient cell.

2. The method of claim 1, wherein the recipient cell is a mammalian cell.

3. The method of claim 2, wherein the mammalian cell is an isolated human cell.

4. The method of claim 3, wherein the transgene construct is introduced into the recipient cell by homologous recombination, recombinase-mediated cassette exchange, microinjection, or a combination of two or more thereof.

5. The method of claim 1, wherein the at least six repeats of a human gamma-satellite DNA monomer acts as a barrier against spread of heterochromatin.

6. The method of claim 5, wherein the at least six repeats of a human gamma-satellite DNA monomer comprises an Ikaros protein binding sequence.

7. The method of claim 1, further comprising detecting expression of the coding nucleic acid sequence at least one month after introducing the transgene construct into the recipient cell, when compared to a control cell, wherein the control cell comprises the transgene construct comprising the coding nucleic acid sequence but lacking the at least six repeats of the human gamma-satellite DNA monomer.

8. The method of claim 1, wherein the coding nucleic acid sequence encodes a therapeutic product.

9. The method of claim 1, wherein the transgene construct comprises an adenoviral or a retroviral sequence.

10. The method of claim 1, wherein the at least six human gamma-satellite DNA monomers are from human chromosome 1, chromosome 8, chromosome 12, chromosome 13, chromosome 21, chromosome 22, chromosome X, or chromosome Y.

11. The method of claim 1, wherein the at least six human gamma-satellite DNA monomers comprise an insulator protein-binding sequence.

12. The method of claim 1, wherein the at least six repeats of a human gamma-satellite DNA monomer comprises one or more of SEQ ID NOS:164-171.

13. A method of inhibiting silencing of a coding nucleic acid sequence to be expressed in a recipient cell, comprising: introducing into a chromosomal site in the recipient cell a transgene construct comprising from 5' to 3', a first human gamma-satellite DNA sequence, a coding nucleic acid sequence to be expressed the recipient cell, and a second human gamma-satellite DNA sequence, wherein the first and second human gamma-satellite DNA sequences are heterologous to the coding nucleic acid sequence, and wherein the human gamma-satellite DNA sequences inhibit silencing of expression of the coding nucleic acid sequence, thereby inhibiting silencing of the coding nucleic acid sequence to be expressed in the recipient cell.

14. The method of claim 13, wherein the first human gamma-satellite DNA sequence and the second human gamma-satellite DNA sequence are the same or substantially the same.

* * * * *

SEQUENCE LISTING

```
<160> NUMBER OF SEQ ID NOS: 171

<210> SEQ ID NO 1
<211> LENGTH: 15
<212> TYPE: DNA
<213> ORGANISM: Artificial sequence
<220> FEATURE:
<223> OTHER INFORMATION: Consenus sequence
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 1
cwgggtggcn tggnc                                                    15

<210> SEQ ID NO 2
<211> LENGTH: 34
<212> TYPE: DNA
<213> ORGANISM: Artificial sequence
<220> FEATURE:
<223> OTHER INFORMATION: Synthetic Oligonucleotide

<400> SEQUENCE: 2
acgtgaattc tggcgaggaa aactgaaaaa ggtg                                34

<210> SEQ ID NO 3
<211> LENGTH: 34
<212> TYPE: DNA
<213> ORGANISM: Artificial sequence
<220> FEATURE:
<223> OTHER INFORMATION: Synthetic Oligonucleotide

<400> SEQUENCE: 3
gccagaattc acgtcctaaa gtgtgtattt ctca                                34

<210> SEQ ID NO 4
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 4
cgatgaaggc ctctccgatc ct                                             22
```

```
<210> SEQ ID NO 5
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 5
gaaagtcctg ggggcttctg ga                                              22

<210> SEQ ID NO 6
<211> LENGTH: 28
<212> TYPE: DNA
<213> ORGANISM: Artificial sequence
<220> FEATURE:
<223> OTHER INFORMATION: Synthetic Oligonucleotide

<400> SEQUENCE: 6
gatcactagt gagctcacgg ggacagcc                                        28

<210> SEQ ID NO 7
<211> LENGTH: 30
<212> TYPE: DNA
<213> ORGANISM: Artificial sequence
<220> FEATURE:
<223> OTHER INFORMATION: Synthetic Oligonucleotide

<400> SEQUENCE: 7
gatctctaga ctctctttca gcctaaagct                                      30

<210> SEQ ID NO 8
<211> LENGTH: 32
<212> TYPE: DNA
<213> ORGANISM: Artificial sequence
<220> FEATURE:
<223> OTHER INFORMATION: Synthetic Oligonucleotide

<400> SEQUENCE: 8
gatcggccgg ccagtgtgct ggaattcgcc ct                                   32

<210> SEQ ID NO 9
<211> LENGTH: 33
<212> TYPE: DNA
<213> ORGANISM: Artificial sequence
<220> FEATURE:
<223> OTHER INFORMATION: Synthetic Oligonucleotide

<400> SEQUENCE: 9
gatcggccgg cctgtgatgg atatctgcag aat                                  33

<210> SEQ ID NO 10
<211> LENGTH: 9
<212> TYPE: DNA
<213> ORGANISM: Artificial sequence
<220> FEATURE:
<223> OTHER INFORMATION: Synthetic Oligonucleotide

<400> SEQUENCE: 10 acttgacga                                                              9

<210> SEQ ID NO 11
<211> LENGTH: 10
<212> TYPE: DNA
<213> ORGANISM: Artificial sequence
<220> FEATURE:
<223> OTHER INFORMATION: Synthetic Oligonucleotide
```

```
<400> SEQUENCE: 11
tgcacactga                                                              10

<210> SEQ ID NO 12
<211> LENGTH: 10
<212> TYPE: DNA
<213> ORGANISM: Artificial sequence
<220> FEATURE:
<223> OTHER INFORMATION: Synthetic Oligonucleotide

<400> SEQUENCE: 12
cgccatattc                                                              10

<210> SEQ ID NO 13
<211> LENGTH: 9
<212> TYPE: DNA
<213> ORGANISM: Artificial sequence
<220> FEATURE:
<223> OTHER INFORMATION: Synthetic Oligonucleotide

<400> SEQUENCE: 13 aattctggg                                                                9

<210> SEQ ID NO 14
<211> LENGTH: 9
<212> TYPE: DNA
<213> ORGANISM: Artificial sequence
<220> FEATURE:
<223> OTHER INFORMATION: Synthetic Oligonucleotide

<400> SEQUENCE: 14 ttaagaccc                                                                9

<210> SEQ ID NO 15
<211> LENGTH: 9
<212> TYPE: DNA
<213> ORGANISM: Artificial sequence
<220> FEATURE:
<223> OTHER INFORMATION: Synthetic Oligonucleotide

<400> SEQUENCE: 15 cctccacag                                                                9

<210> SEQ ID NO 16
<211> LENGTH: 49
<212> TYPE: DNA
<213> ORGANISM: Artificial sequence
<220> FEATURE:
<223> OTHER INFORMATION: Synthetic Oligonucleotide

<400> SEQUENCE: 16
gttacctatc gatatcggac cgtctagaca gaagcattct cagaaactt                   49

<210> SEQ ID NO 17
<211> LENGTH: 39
<212> TYPE: DNA
<213> ORGANISM: Artificial sequence
<220> FEATURE:
<223> OTHER INFORMATION: Synthetic Oligonucleotide

<400> SEQUENCE: 17
atgactacgc gtaaacactc tttttgtaga atctgcaag                              39

<210> SEQ ID NO 18
```

```
<211> LENGTH: 45
<212> TYPE: DNA
<213> ORGANISM: Artificial sequence
<220> FEATURE:
<223> OTHER INFORMATION: Synthetic Oligonucleotide

<400> SEQUENCE: 18
cctatacttt ctagagaata ggaacttctg gccggccccg gaccg            45

<210> SEQ ID NO 19
<211> LENGTH: 48
<212> TYPE: DNA
<213> ORGANISM: Artificial sequence
<220> FEATURE:
<223> OTHER INFORMATION: Synthetic Oligonucleotide

<400> SEQUENCE: 19
gttactatcg atagaagttc ctatactttc tagagaatag gaacttcg         48

<210> SEQ ID NO 20
<211> LENGTH: 35
<212> TYPE: DNA
<213> ORGANISM: Artificial sequence
<220> FEATURE:
<223> OTHER INFORMATION: Synthetic Oligonucleotide

<400> SEQUENCE: 20
cgcagcggcc gcatctgtgc ggtatttcac accgc                       35

<210> SEQ ID NO 21
<211> LENGTH: 29
<212> TYPE: DNA
<213> ORGANISM: Artificial sequence
<220> FEATURE:
<223> OTHER INFORMATION: Synthetic Oligonucleotide

<400> SEQUENCE: 21
tatgtcgaca tcggatgcag cccggttaa                              29

<210> SEQ ID NO 22
<211> LENGTH: 30
<212> TYPE: DNA
<213> ORGANISM: Artificial sequence
<220> FEATURE:
<223> OTHER INFORMATION: Synthetic Oligonucleotide

<400> SEQUENCE: 22
gatcgtcgac tgaaagccac gttgtgtctc                             30

<210> SEQ ID NO 23
<211> LENGTH: 30
<212> TYPE: DNA
<213> ORGANISM: Artificial sequence
<220> FEATURE:
<223> OTHER INFORMATION: Synthetic Oligonucleotide

<400> SEQUENCE: 23
gatcacgcgt actgatgcat gatccgggtt                             30

<210> SEQ ID NO 24
<211> LENGTH: 46
<212> TYPE: DNA
<213> ORGANISM: Artificial sequence
<220> FEATURE:
<223> OTHER INFORMATION: Synthetic Oligonucleotide

<400> SEQUENCE: 24
```
tgtcggatcg attacggacc gatgtgaaga tattcccgtt tccaac         46

<210> SEQ ID NO 25
<211> LENGTH: 40
<212> TYPE: DNA
<213> ORGANISM: Artificial sequence
<220> FEATURE:
<223> OTHER INFORMATION: Synthetic Oligonucleotide

<400> SEQUENCE: 25
catggtaacg cgtctgctct atcaaaagga aggttcaact         40

<210> SEQ ID NO 26
<211> LENGTH: 73
<212> TYPE: DNA
<213> ORGANISM: Artificial sequence
<220> FEATURE:
<223> OTHER INFORMATION: Synthetic Oligonucleotide

<400> SEQUENCE: 26
attctctaga aagtatagga acttcgacgt cagcggccgc acggaccgat gtgaagatat         60
tcccgtttcc aac         73

<210> SEQ ID NO 27
<211> LENGTH: 63
<212> TYPE: DNA
<213> ORGANISM: Artificial sequence
<220> FEATURE:
<223> OTHER INFORMATION: Synthetic Oligonucleotide

<400> SEQUENCE: 27
tgtcggatcg atagctagca accgcggtga agttcctatt ctctagaaag tataggaact         60
tcg         63

<210> SEQ ID NO 28
<211> LENGTH: 33
<212> TYPE: DNA
<213> ORGANISM: Artificial sequence
<220> FEATURE:
<223> OTHER INFORMATION: Synthetic Oligonucleotide

<400> SEQUENCE: 28
atgcgcggcc gccgaaaagt gccacctggg tcc         33

<210> SEQ ID NO 29
<211> LENGTH: 26
<212> TYPE: DNA
<213> ORGANISM: Artificial sequence
<220> FEATURE:
<223> OTHER INFORMATION: Synthetic Oligonucleotide

<400> SEQUENCE: 29
ttgtggtttg tccaaactca tcaatg         26

<210> SEQ ID NO 30
<211> LENGTH: 30
<212> TYPE: DNA
<213> ORGANISM: Artificial sequence
<220> FEATURE:
<223> OTHER INFORMATION: Synthetic Oligonucleotide

<400> SEQUENCE: 30
gatcgggccc tcccgtcaag tcagcgtaat         30

<210> SEQ ID NO 31
<211> LENGTH: 30
<212> TYPE: DNA
<213> ORGANISM: Artificial sequence
<220> FEATURE:
<223> OTHER INFORMATION: Synthetic Oligonucleotide

<400> SEQUENCE: 31
gatcacgcgt actgatgcat gatccgggtt                              30

<210> SEQ ID NO 32
<211> LENGTH: 131
<212> TYPE: DNA
<213> ORGANISM: Artificial sequence
<220> FEATURE:
<223> OTHER INFORMATION: Synthetic Oligonucleotide

<400> SEQUENCE: 32
gatccggacc gatggcgagg aaaactgaaa aaggtggaaa atttagaaat gtccactgta    60
ggacgtggaa tatggcaaga aaactgaaaa tcatggaaaa tgagaaacat ccacttgacg   120
aacgcgtgat c                                                       131

<210> SEQ ID NO 33
<211> LENGTH: 138
<212> TYPE: DNA
<213> ORGANISM: Artificial sequence
<220> FEATURE:
<223> OTHER INFORMATION: Synthetic Oligonucleotide

<400> SEQUENCE: 33
gatcacgcgt tgaaaaatga cgaaatcact aaaaacgtga aaaatgagaa atgcacactg    60
aaggacctgg aatatggcga gaaaactgaa atcacggaa atgagaaat acacacttta    120 ggacgtgcgg accggatc                                                138

<210> SEQ ID NO 34
<211> LENGTH: 163
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (116)..(116)
<223> OTHER INFORMATION: n is a, c, g, or t

<400> SEQUENCE: 34
gatccggacc gactatggtg gacattgtgg tcaggcagag gtgagaagac agtgagaccg    60
cagggaatgc tgggagcctc ctagggatgt ctctcccacc ccagaagctt accatngttg   120
tttcggatgg gctgtaatac cccatgcttt ggtacgcgtg atc                    163

<210> SEQ ID NO 35
<211> LENGTH: 128
<212> TYPE: DNA
<213> ORGANISM: Artificial sequence
<220> FEATURE:
<223> OTHER INFORMATION: Synthetic Oligonucleotide

<400> SEQUENCE: 35
gatcacgcgt gtagagggaa gaattggcaa gactgcaggg taatgctgcg accctcccaa    60
ggagagcctc tcccatccta gaagcccccc aggtctgtca cggataggct gtagtgtcgg   120
accggatc                                                           128

<210> SEQ ID NO 36
<211> LENGTH: 108
<212> TYPE: DNA
<213> ORGANISM: Artificial sequence
<220> FEATURE:
<223> OTHER INFORMATION: Synthetic Oligonucleotide

<400> SEQUENCE: 36
atgcatcgat aagagtgttt caaaactgct ctatcaaaag gaatgttcaa cgcgtgagtt          60
gaatgcaaac ttcacaaaga agtttctgag aatgctcgag gcatgcat                     108

<210> SEQ ID NO 37
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 37
aagtaagtgt gccctctact gg                                                  22

<210> SEQ ID NO 38
<211> LENGTH: 29
<212> TYPE: DNA
<213> ORGANISM: Artificial sequence
<220> FEATURE:
<223> OTHER INFORMATION: Synthetic Oligonucleotide

<400> SEQUENCE: 38
agaataacaa ggaggtggct ggaaacttg                                           29

<210> SEQ ID NO 39
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 39
gaattctggg agtgacccaa                                                     20

<210> SEQ ID NO 40
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 40
tcactccctg ggcacgaacc                                                     20

<210> SEQ ID NO 41
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 41
gcccacgtaa ttcaattcac t                                                   21

<210> SEQ ID NO 42
<211> LENGTH: 21
<212> TYPE: DNA

<213> ORGANISM: Artificial sequence
<220> FEATURE:
<223> OTHER INFORMATION: Synthetic Oligonucleotide

<400> SEQUENCE: 42
tcacagaagt atgccaagcg a                                         21

<210> SEQ ID NO 43
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 43
gggtaccgag ctcgaattca ct                                        22

<210> SEQ ID NO 44
<211> LENGTH: 24
<212> TYPE: DNA
<213> ORGANISM: Artificial sequence
<220> FEATURE:
<223> OTHER INFORMATION: Synthetic Oligonucleotide

<400> SEQUENCE: 44
gccgtcgttt tacaacgtcg tgac                                      24

<210> SEQ ID NO 45
<211> LENGTH: 25
<212> TYPE: DNA
<213> ORGANISM: Artificial sequence
<220> FEATURE:
<223> OTHER INFORMATION: Synthetic Oligonucleotide

<400> SEQUENCE: 45
gggaaaaccc tggcgttacc caact                                     25

<210> SEQ ID NO 46
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 46
gttatccgct cacaattcca ca                                        22

<210> SEQ ID NO 47
<211> LENGTH: 24
<212> TYPE: DNA
<213> ORGANISM: Artificial sequence
<220> FEATURE:
<223> OTHER INFORMATION: Synthetic Oligonucleotide

<400> SEQUENCE: 47
ccacacaaca tacgagccgg aagc                                      24

<210> SEQ ID NO 48
<211> LENGTH: 23
<212> TYPE: DNA
<213> ORGANISM: Artificial sequence
<220> FEATURE:
<223> OTHER INFORMATION: Synthetic Oligonucleotide

<400> SEQUENCE: 48
cctggggtgc ctaatgagtg agc                                       23

```
<210> SEQ ID NO 49
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 49
cgttttccca taggctccgc c                                         21

<210> SEQ ID NO 50
<211> LENGTH: 23
<212> TYPE: DNA
<213> ORGANISM: Artificial sequence
<220> FEATURE:
<223> OTHER INFORMATION: Synthetic Oligonucleotide

<400> SEQUENCE: 50
cggtaagaca cgacttatcg cca                                       23

<210> SEQ ID NO 51
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 51
cacagcagta aaaccctaac ta                                        22

<210> SEQ ID NO 52
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 52
tggaggcccc tctccactca                                           20

<210> SEQ ID NO 53
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 53
gtgaagacca ggcatggagg ct                                        22

<210> SEQ ID NO 54
<211> LENGTH: 23
<212> TYPE: DNA
<213> ORGANISM: Artificial sequence
<220> FEATURE:
<223> OTHER INFORMATION: Synthetic Oligonucleotide

<400> SEQUENCE: 54
aagctctccc cactggtttg ctc                                       23

<210> SEQ ID NO 55
<211> LENGTH: 23
<212> TYPE: DNA
<213> ORGANISM: Artificial sequence
<220> FEATURE:
```

<223> OTHER INFORMATION: Synthetic Oligonucleotide

<400> SEQUENCE: 55
catgagcctg tggggagatg tcc                                            23

<210> SEQ ID NO 56
<211> LENGTH: 23
<212> TYPE: DNA
<213> ORGANISM: Artificial sequence
<220> FEATURE:
<223> OTHER INFORMATION: Synthetic Oligonucleotide

<400> SEQUENCE: 56
gtctcactct gtagtgcaga aca                                            23

<210> SEQ ID NO 57
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 57
catggtcata ctttccctag ct                                             22

<210> SEQ ID NO 58
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 58
cacagcagta aaaccctaac ta                                             22

<210> SEQ ID NO 59
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 59
aacggagtaa cctcggtgtg                                                20

<210> SEQ ID NO 60
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 60
gctgctgagt gggagagag                                                 19

<210> SEQ ID NO 61
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 61
gctgtacaag taaagcggcc                                                20

```
<210> SEQ ID NO 62
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 62
caagacgttt cccgttgaat                                               20

<210> SEQ ID NO 63
<211> LENGTH: 24
<212> TYPE: DNA
<213> ORGANISM: Artificial sequence
<220> FEATURE:
<223> OTHER INFORMATION: Synthetic Oligonucleotide

<400> SEQUENCE: 63
aacgccaggg ttttcccagt cacg                                          24

<210> SEQ ID NO 64
<211> LENGTH: 23
<212> TYPE: DNA
<213> ORGANISM: Artificial sequence
<220> FEATURE:
<223> OTHER INFORMATION: Synthetic Oligonucleotide

<400> SEQUENCE: 64
gggcagtgag cgcaacgcaa tta                                           23

<210> SEQ ID NO 65
<211> LENGTH: 26
<212> TYPE: DNA
<213> ORGANISM: Artificial sequence
<220> FEATURE:
<223> OTHER INFORMATION: Synthetic Oligonucleotide

<400> SEQUENCE: 65
ggcggtaatg ttggacatga gcgaat                                        26

<210> SEQ ID NO 66
<211> LENGTH: 25
<212> TYPE: DNA
<213> ORGANISM: Artificial sequence
<220> FEATURE:
<223> OTHER INFORMATION: Synthetic Oligonucleotide

<400> SEQUENCE: 66
ctgaagcttc ccgggggtac cgaat                                         25

<210> SEQ ID NO 67
<211> LENGTH: 25
<212> TYPE: DNA
<213> ORGANISM: Artificial sequence
<220> FEATURE:
<223> OTHER INFORMATION: Synthetic Oligonucleotide

<400> SEQUENCE: 67
cggccgctga cgtcgaagtt cctat                                         25

<210> SEQ ID NO 68
<211> LENGTH: 25
<212> TYPE: DNA
<213> ORGANISM: Artificial sequence
<220> FEATURE:
<223> OTHER INFORMATION: Synthetic Oligonucleotide
```

<400> SEQUENCE: 68
tcactctcgg catggacgag ctgta                                    25

<210> SEQ ID NO 69
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 69
atggcctgaa tcacttggac                                          20

<210> SEQ ID NO 70
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 70
ttctgctgct ttccctcatt                                          20

<210> SEQ ID NO 71
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 71
cagggagcca acagtctttc                                          20

<210> SEQ ID NO 72
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 72
tcgtgacgtc tatggttact c                                        21

<210> SEQ ID NO 73
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 73
tcaccaatgc actcaacgat                                          20

<210> SEQ ID NO 74
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 74
ctggggaagc atggttctaa                                          20

<210> SEQ ID NO 75
<211> LENGTH: 20

<212> TYPE: DNA
<213> ORGANISM: Artificial sequence
<220> FEATURE:
<223> OTHER INFORMATION: Synthetic Oligonucleotide

<400> SEQUENCE: 75
agaacggcat caaggtgaac                                              20

<210> SEQ ID NO 76
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 76
ttatggcatg gcgatttgta                                              20

<210> SEQ ID NO 77
<211> LENGTH: 23
<212> TYPE: DNA
<213> ORGANISM: Artificial sequence
<220> FEATURE:
<223> OTHER INFORMATION: Synthetic Oligonucleotide

<400> SEQUENCE: 77
gtgctgtaat gcttcaggtt ttg                                          23

<210> SEQ ID NO 78
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 78
ctgtggggac agacacacac                                              20

<210> SEQ ID NO 79
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 79
acctgacgtg ctgtctcctt                                              20

<210> SEQ ID NO 80
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 80
ttctcaggat ccacatgcag                                              20

<210> SEQ ID NO 81
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 81

-continued cgaacaggtg gacaatagca                    20

<210> SEQ ID NO 82
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 82
ccacacaagg agtccaaggt                    20

<210> SEQ ID NO 83
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 83
ctctgctgaa gccagttacc tt                 22

<210> SEQ ID NO 84
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 84
cagtagcaga acaggccaca                    20

<210> SEQ ID NO 85
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 85
caccagttga agagcgttga                    20

<210> SEQ ID NO 86
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 86
tgctcaggta gtggttgtcg                    20

<210> SEQ ID NO 87
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 87
tgaccttccc agtcttgctt                    20

<210> SEQ ID NO 88
<211> LENGTH: 21
<212> TYPE: DNA
<213> ORGANISM: Artificial sequence

```
<220> FEATURE:
<223> OTHER INFORMATION: Synthetic Oligonucleotide

<400> SEQUENCE: 88
caacctattc caaagcctgg g                                              21

<210> SEQ ID NO 89
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 89
tttcaggggt acgttgaagc                                                20

<210> SEQ ID NO 90
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 90
gaggcctact tgcgactttg                                                20

<210> SEQ ID NO 91
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 91
ctgggagtga cccaaagagg                                                20

<210> SEQ ID NO 92
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 92
ctatgagctt ctgtgatggg                                                20

<210> SEQ ID NO 93
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 93
gggaagagtc cagacggcag                                                20

<210> SEQ ID NO 94
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 94
atggccaggc cgcagggac                                                 19
```

```
<210> SEQ ID NO 95
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 95
ggctggatgg catgggccg                                                  19

<210> SEQ ID NO 96
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 96
caaaaacagt gccgcagt                                                   18

<210> SEQ ID NO 97
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 97
ccccaggctt tggaacagcg                                                 20

<210> SEQ ID NO 98
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 98
ggcaggcaga gatgagaag                                                  19

<210> SEQ ID NO 99
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 99
gggcagcagg gactcacgg                                                  19

<210> SEQ ID NO 100
<211> LENGTH: 23
<212> TYPE: DNA
<213> ORGANISM: Artificial sequence
<220> FEATURE:
<223> OTHER INFORMATION: Synthetic Oligonucleotide

<400> SEQUENCE: 100
gtgctgtaat gcttcaggtt ttg                                             23

<210> SEQ ID NO 101
<211> LENGTH: 20
<212> TYPE: DNA
<213> ORGANISM: Artificial sequence
<220> FEATURE:
<223> OTHER INFORMATION: Synthetic Oligonucleotide
```

```
<400> SEQUENCE: 101
atgctgcgac cctcccaagg                                               20

<210> SEQ ID NO 102
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 102
aattcaaata aaaggtagac                                               20

<210> SEQ ID NO 103
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 103
aaaagtaaat atcttccata                                               20

<210> SEQ ID NO 104
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 104
tatcgttgga aaagggaata                                               20

<210> SEQ ID NO 105
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 105
aaacgggaat atcatcatct                                               20

<210> SEQ ID NO 106
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 106
tgcctttgtt gaaaaggaaa                                               20

<210> SEQ ID NO 107
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 107
gattgctttg aggatttcgt                                               20

<210> SEQ ID NO 108
```

```
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 108
cgcctacggt gaaaaaggaa                                                 20

<210> SEQ ID NO 109
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 109
ggatagcttg gaggatttcg                                                 20

<210> SEQ ID NO 110
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 110
ggacatttgg agcgctttga                                                 20

<210> SEQ ID NO 111
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 111
ctgtggggac agacacacac                                                 20

<210> SEQ ID NO 112
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 112
acctgacgtg ctgtctcctt                                                 20

<210> SEQ ID NO 113
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 113
gaatgggatg agaacgcagg g                                               21

<210> SEQ ID NO 114
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 114
``` gggtcttct gagatagaag                                                  20

<210> SEQ ID NO 115
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 115
tcccagcatt ccctgcggtc                                                 20

<210> SEQ ID NO 116
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 116
cttctcctct atgcttgcc                                                  19

<210> SEQ ID NO 117
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 117
gcctcaacgt ctccctgag                                                  19

<210> SEQ ID NO 118
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 118
ccagcccacg ccaccctgcg g                                               21

<210> SEQ ID NO 119
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 119
acagccctgg gtgcttctgg g                                               21

<210> SEQ ID NO 120
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 120
ctcccagcat tccatgtgg                                                  19

<210> SEQ ID NO 121
<211> LENGTH: 19
<212> TYPE: DNA

<213> ORGANISM: Artificial sequence
<220> FEATURE:
<223> OTHER INFORMATION: Synthetic Oligonucleotide

<400> SEQUENCE: 121 cccctttttcc gcttgtggg                              19

<210> SEQ ID NO 122
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 122
caacctattc caaagcctgg g                            21

<210> SEQ ID NO 123
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 123
gaattccttg tggggctcg                               19

<210> SEQ ID NO 124
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 124
aaaggttcca ctctgttagc                              20

<210> SEQ ID NO 125
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 125
tctgttagtt gaggacacac                              20

<210> SEQ ID NO 126
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 126
gaatgcagat atcaccaagt                              20

<210> SEQ ID NO 127
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 127
cttttagttg agtacacaca                              20

<210> SEQ ID NO 128
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 128
ttgaatggaa atatccgaaa                                                    20

<210> SEQ ID NO 129
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 129
tatcaccaac aagtttctga                                                    20

<210> SEQ ID NO 130
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 130
tgaatgcagt catcagaaag                                                    20

<210> SEQ ID NO 131
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 131
tcacaaactt gtttctcaga                                                    20

<210> SEQ ID NO 132
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 132
tctgagaggg cttctgtcta                                                    20

<210> SEQ ID NO 133
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 133
tttcaggggt acgttgaagc                                                    20

<210> SEQ ID NO 134
<211> LENGTH: 20
<212> TYPE: DNA
<213> ORGANISM: Artificial sequence
<220> FEATURE:

<223> OTHER INFORMATION: Synthetic Oligonucleotide

<400> SEQUENCE: 134
gaggcctact tgcgactttg                                        20

<210> SEQ ID NO 135
<211> LENGTH: 59
<212> TYPE: DNA
<213> ORGANISM: Homo sapiens

<400> SEQUENCE: 135
cgaaaatggg gccacatggt ggcttgggtg ggcggcaaag acccagggtg accttgagg    59

<210> SEQ ID NO 136
<211> LENGTH: 59
<212> TYPE: DNA
<213> ORGANISM: Homo sapiens

<400> SEQUENCE: 136
cggaaaaggg gctgcagtgt ggcgtcgaca ggccacaggg actcaggggg aagttgaaa    59

<210> SEQ ID NO 137
<211> LENGTH: 59
<212> TYPE: DNA
<213> ORGANISM: Homo sapiens

<400> SEQUENCE: 137
agagaatgag gtggcagggt ggcgtgcatg ggcagcaggg actcacggac actttgagg    59

<210> SEQ ID NO 138
<211> LENGTH: 59
<212> TYPE: DNA
<213> ORGANISM: Homo sapiens

<400> SEQUENCE: 138
caaaaacaag gccgcagggt ggcgtgggcg ggccgcaggg actcaggtgg aaattgtgg    59

<210> SEQ ID NO 139
<211> LENGTH: 59
<212> TYPE: DNA
<213> ORGANISM: Homo sapiens

<400> SEQUENCE: 139
caaaaacagt gccgcagtgt ggcctgggcg ggccacaggg actcagggag acgttgagg    59

<210> SEQ ID NO 140
<211> LENGTH: 59
<212> TYPE: DNA
<213> ORGANISM: Homo sapiens

<400> SEQUENCE: 140
agacaacagg gcggctggat ggcatgggcc gatcgtagga acccagggag acattgagg    59

<210> SEQ ID NO 141
<211> LENGTH: 59
<212> TYPE: DNA
<213> ORGANISM: Homo sapiens

<400> SEQUENCE: 141
tgaaaacagg gaggcagggt ggcatggcca ggccgcaggg actatggtgg acattgtgg    59

<210> SEQ ID NO 142
<211> LENGTH: 59

<212> TYPE: DNA
<213> ORGANISM: Homo sapiens

<400> SEQUENCE: 142
cgaaaatggg gccactgggt ggcctgaacg agccaaaggg actcaggtg acactgagg        59

<210> SEQ ID NO 143
<211> LENGTH: 55
<212> TYPE: DNA
<213> ORGANISM: Artificial
<220> FEATURE:
<223> OTHER INFORMATION: Consensus sequence

<400> SEQUENCE: 143
cgaaaatggg gccactgggt ggcctgaacg agccaaaggg actcaggtg acact            55

<210> SEQ ID NO 144
<211> LENGTH: 55
<212> TYPE: DNA
<213> ORGANISM: Artificial sequence
<220> FEATURE:
<223> OTHER INFORMATION: Consensus sequence

<400> SEQUENCE: 144
cgaaaatggg gccactaaat ggtctgaacg agccaaaggg actcaggtg acact            55

<210> SEQ ID NO 145
<211> LENGTH: 55
<212> TYPE: DNA
<213> ORGANISM: Artificial sequence
<220> FEATURE:
<223> OTHER INFORMATION: Consensus sequence

<400> SEQUENCE: 145
cgaaaatggg gccactgagt ggtttgaatg agccaaaggg actcaggtg acact            55

<210> SEQ ID NO 146
<211> LENGTH: 55
<212> TYPE: DNA
<213> ORGANISM: Artificial sequence
<220> FEATURE:
<223> OTHER INFORMATION: Consensus sequence

<400> SEQUENCE: 146
cgaaaatggg gtcattaggt ggtctgaatg agccaaaggg actcaggtg acact            55

<210> SEQ ID NO 147
<211> LENGTH: 189
<212> TYPE: DNA
<213> ORGANISM: Artificial sequence
<220> FEATURE:
<223> OTHER INFORMATION: Consensus sequence

<400> SEQUENCE: 147
catgcgtggg gcccagggga ccctgggcat ccctggttca tgcccacgga gtgcctcggg       60
cccacggggg ccagcccaag gcggcaggaa ggcttgaaag gggaggtcga ggcacctgtg      120
ttgtggaagg aaaacacaaa cggcgaggca gaggtccccc cccacgggcg aaagtgcctc      180
cccaccgcg                                                             189

<210> SEQ ID NO 148
<211> LENGTH: 218
<212> TYPE: DNA
<213> ORGANISM: Artificial sequence
<220> FEATURE:

<223> OTHER INFORMATION: Consensus sequence

<400> SEQUENCE: 148

| cctgcgccgg acccgggggg gtcgtggagt ccctggcttt cacccagggt gcgtgtctct | 60 |
| cccactgggg gcaccccaaa gcggcaagaa gtccccagg ggacagggac aggacgccag | 120 |
| gctttcaggg ggacgttgag gcaggccggg gaaaaaagcg gcgaggccaa agaggaggct | 180 |
| ggggtcctcc cccggaggtc agtgccttcc cggcagcc | 218 |

<210> SEQ ID NO 149
<211> LENGTH: 216
<212> TYPE: DNA
<213> ORGANISM: Artificial sequence
<220> FEATURE:
<223> OTHER INFORMATION: Consensus sequence

<400> SEQUENCE: 149

| ccagggctgt cccgggcggg ctgtaaagcc ccaggctttg gagcagggtg cctgtgtctc | 60 |
| tcgcggaagg cccccacaag cgaaaacggg gccgcagggt ggcgtgtgcg ggccgcagaa | 120 |
| actcaggggg acattgaggc aggcagaggg gagaagcggc gagacctcag ggaatgctgg | 180 |
| gagcctccca aggaggcctc tcccatccca gaagcc | 216 |

<210> SEQ ID NO 150
<211> LENGTH: 236
<212> TYPE: DNA
<213> ORGANISM: Mus musculus

<400> SEQUENCE: 150

| attcacgtcc taaagtgtgt atttctcatt ttccgtaatt ttcagttttc tcaccatatt | 60 |
| ccaggtcctt cagtgggcat ttctcatttt tcacgttttt tagtgatttc gtcattttc | 120 |
| aagtcgtcaa gtggatgttt ctcattttcc atgattttca gttttcttgc catattccac | 180 |
| gtcctacagt ggacatttct aaattttcca cctttttcag ttttcctttc tccata | 236 |

<210> SEQ ID NO 151
<211> LENGTH: 234
<212> TYPE: DNA
<213> ORGANISM: Mus musculus

<400> SEQUENCE: 151

| tttcacgtcc taaagtgtgt atttctcatt ttccgtgatt ttcagttttc tcaccatatt | 60 |
| ccaggtcctt cggtgtgcat ttctcatttt tcacgtttat tagtgatttc gtcattttc | 120 |
| aagtcgtcaa gtggatgttt ctcattttcc atgattttcg gttttcttgc catattccac | 180 |
| gtcctacagt ggacatttct aaattttcca cctttttcag ttttcctcgc cata | 234 |

<210> SEQ ID NO 152
<211> LENGTH: 234
<212> TYPE: DNA
<213> ORGANISM: Mus musculus

<400> SEQUENCE: 152

| tttcacgtcc taaagtgtgt atttctcatt ttccgtgatt ttcagttttc tcgccatatt | 60 |
| ccaggtcctt cagtgtgcat ttctcatttt tcacgttttt tagtgatttc gtcattttc | 120 |
| aagtcgtcca gtggatgttt ctcatttttcc atgattttca gttttcttgc catattccac | 180 |
| gtcctacagt ggacatttct aaattttcca cctttttcag ttttcctcgc caga | 234 |

```
<210> SEQ ID NO 153
<211> LENGTH: 24
<212> TYPE: DNA
<213> ORGANISM: Artificial sequence
<220> FEATURE:
<223> OTHER INFORMATION: Synthetic Oligonucleotide

<400> SEQUENCE: 153
ttcaacgtac ccctgaaagc ctgg                                               24

<210> SEQ ID NO 154
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 154
aaggaagcat cttcccagaa                                                    20

<210> SEQ ID NO 155
<211> LENGTH: 28
<212> TYPE: DNA
<213> ORGANISM: Artificial sequence
<220> FEATURE:
<223> OTHER INFORMATION: Synthetic Oligonucleotide

<400> SEQUENCE: 155
ttgcaaatta ctcctgcctc caggcctt                                           28

<210> SEQ ID NO 156
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 156
gaattccttg tgggctcgc                                                     19

<210> SEQ ID NO 157
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 157
gcagaggtca ccccaacga                                                     20

<210> SEQ ID NO 158
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 158
aaggagtgtg accaaaactc a                                                  21

<210> SEQ ID NO 159
<211> LENGTH: 21
<212> TYPE: DNA
<213> ORGANISM: Artificial sequence
<220> FEATURE:
<223> OTHER INFORMATION: Synthetic Oligonucleotide
```

```
<400> SEQUENCE: 159
ctattttgtc ccaagcctgc c                                              21

<210> SEQ ID NO 160
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 160
tatggcgagg aaaactg                                                   17

<210> SEQ ID NO 161
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 161
cagtggacat ttctaaattt                                                20

<210> SEQ ID NO 162
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 162
tttcacgtcc taaagtgtg                                                 19

<210> SEQ ID NO 163
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 163
ggaatatggt gagaaaactg                                                20

<210> SEQ ID NO 164
<211> LENGTH: 185
<212> TYPE: DNA
<213> ORGANISM: Homo Sapiens

<400> SEQUENCE: 164
ggagcctccc aacattccct gcgttctcat ccattctccc ctctccctgc ctcaacggac     60
ccctgaaggc ctcatacaag cgaaaatggg gccacatggt gatggtggct tgggtgggcg    120
gcaaagaccc agggtgacct tgaggcaggc agaggggga agagtccaga cggcagggaa    180
tgctg                                                               185

<210> SEQ ID NO 165
<211> LENGTH: 217
<212> TYPE: DNA
<213> ORGANISM: Homo Sapiens

<400> SEQUENCE: 165
ggagcctcct aaggatgaat cttctatctc agaagacccc aggattgttc ctggagggat     60
gtaaagcccg aggcttcaaa gcaggatgcc tgtgtttctc gtaaatggcc cccacaagtg    120
```

```
aaaacaggga ggcagggtgg catggccagg ccgcagggac tatggtggac attgtggcag    180
gcagaggtga gaagcagtga gaccgcaggg aatgctg                              217
```

<210> SEQ ID NO 166
<211> LENGTH: 217
<212> TYPE: DNA
<213> ORGANISM: Homo Sapiens

<400> SEQUENCE: 166

```
ggagcctcct agggatgtct ctcccacccc agaagcttcc atggttgttt cggatgggct    60 gtaataccccc atgctttggt gcaggacgac tgtgtctcta gcagaagatc cccaacagag   120
acaacagggc ggctggatgg catgggccga tcgtaggaac ccaggagac attgaggcaa     180 gcatagagga gaagcaacga gaccgtaggg aatgctg                             217
```

<210> SEQ ID NO 167
<211> LENGTH: 217
<212> TYPE: DNA
<213> ORGANISM: Homo Sapiens

<400> SEQUENCE: 167

```
agagccttcc aaggaggtgt ctcccatccc agaagctcct aggactgtcc tggacaggct    60
gtaaggccca agactttgga gcagagtgtc tgtgtctctc ttggaagacc ccctcaagca   120
aaaacagtgc cgcagtgtgg cctgggcggg ccacaggac tcagggagac gttgaggcag    180
gcagaggaaa gaagcggcga gaccgcaggg aatgctg                             217
```

<210> SEQ ID NO 168
<211> LENGTH: 238
<212> TYPE: DNA
<213> ORGANISM: Homo Sapiens

<400> SEQUENCE: 168

```
ggagccttcc taaaagacct atcccatccc agaagctccc caaactatcc tgggtgggct    60
ataaagcccc aggctttgga acagcgtgct tgtgtctctc gcaaaatact cccacaagca   120 aaacaaggc cgcagggtgg cgtgggctgg ctgcaggtg gcgtgggagg gccgcaggga    180
ctcaggtgga aattgtggca ggcagagatg agaagcagca agacctcaga gaatgctg    238
```

<210> SEQ ID NO 169
<211> LENGTH: 214
<212> TYPE: DNA
<213> ORGANISM: Homo Sapiens

<400> SEQUENCE: 169

```
gaagcctcac aaggacatct ctcatcccag aagcacccag ggctgtcccg gcaagctttt   60
atgtcccagt ctttagagca gggagcctgt gtctctcgca gaagacatac aaaagagaga   120
atgaggtggc agggtggcgt gcatgggcag caggggactca cggacacttt gaggcaggca   180
gatgagagaa gcagcaggac cacatggaat gctg                                214
```

<210> SEQ ID NO 170
<211> LENGTH: 217
<212> TYPE: DNA
<213> ORGANISM: Homo Sapiens

<400> SEQUENCE: 170

```
ggagcctccc aaggaggcct ctttcatctc agaagccccc aggactgtcc cgggcgtgct    60
```

```
gtaatgcttc aggttttgaa gcagagtgcc tgtgtctcta gcggaaggct cccacaagcg    120 gaaaagggc tgcagtgtgg cgtcgacagg ccacagggac tcagggggaa gttgaaacca    180
gtagagggga gaattggcaa gactgcaggg aatgctg                            217

<210> SEQ ID NO 171
<211> LENGTH: 212
<212> TYPE: DNA
<213> ORGANISM: Homo Sapiens

<400> SEQUENCE: 171
cgaccctccc aaggaggcct ctcccatcct agaagccccc aggtctgtca cggataggct     60
gtagtgtccc aggctttgga ataggttgcc tgtgtctgtg gcaggtttcc acaggcgaaa    120
atggggccac tgggtggcct gaacgagcca aagggactca gggtgacact gaggcaggga    180
gaagggacaa gcagcgagcc cacaaggaat tc                                 212
```